US009777076B2

(12) United States Patent
Donald et al.

(10) Patent No.: US 9,777,076 B2
(45) Date of Patent: Oct. 3, 2017

(54) SACCHARIDES AND USES THEREOF

(71) Applicant: Pfizer Inc., New York, NY (US)

(72) Inventors: Robert G. K. Donald, South Orange, NJ (US); Srinivas Kodali, Hillsborough, NJ (US); Evguenii Vinogradov, Ottawa (CA)

(73) Assignee: Pfizer Inc., New York, NY (US)

( * ) Notice: Subject to any disclaimer, the term of this patent is extended or adjusted under 35 U.S.C. 154(b) by 371 days.

(21) Appl. No.: 14/412,646

(22) PCT Filed: Jul. 3, 2013

(86) PCT No.: PCT/IB2013/055452
§ 371 (c)(1),
(2) Date: Jan. 2, 2015

(87) PCT Pub. No.: WO2014/013375
PCT Pub. Date: Jan. 23, 2014

(65) Prior Publication Data
US 2016/0002361 A1    Jan. 7, 2016

Related U.S. Application Data

(60) Provisional application No. 61/672,221, filed on Jul. 16, 2012.

(51) Int. Cl.
A61K 31/715    (2006.01)
A61K 47/48     (2006.01)
C08B 37/00     (2006.01)
C08H 1/00      (2006.01)

(52) U.S. Cl.
CPC .......... *C08B 37/006* (2013.01); *A61K 31/715* (2013.01); *A61K 47/48246* (2013.01); *C08H 1/00* (2013.01)

(58) Field of Classification Search
None
See application file for complete search history.

(56) References Cited

U.S. PATENT DOCUMENTS

| | | | |
|---|---|---|---|
| 4,356,170 A | 10/1982 | Jennings et al. | |
| 4,606,919 A | 8/1986 | Stojkovic et al. | |
| 4,619,828 A | 10/1986 | Gordon | |
| 4,663,160 A | 5/1987 | Tsay et al. | |
| 5,124,153 A | 6/1992 | Beachey et al. | |
| 5,162,226 A | 11/1992 | Beachey et al. | |
| 5,614,382 A | 3/1997 | Metcalf | |
| 5,989,542 A | 11/1999 | Pier et al. | |
| 6,291,431 B1 | 9/2001 | Balaban et al. | |
| 6,448,043 B1 | 9/2002 | Choi et al. | |
| 6,544,516 B1 | 4/2003 | Burnie et al. | |
| 6,583,275 B1 | 6/2003 | Doucette-Stamm | |
| 6,610,293 B1 | 8/2003 | Fischer et al. | |
| 6,617,156 B1 | 9/2003 | Doucette-Stamm et al. | |
| 6,722,062 B2 | 4/2004 | Pier et al. | |
| 6,756,361 B1 | 6/2004 | Fattom et al. | |
| 6,790,448 B2 | 9/2004 | Xu et al. | |
| 6,815,172 B1 | 11/2004 | Martinez et al. | |
| 6,818,761 B2 | 11/2004 | Giori et al. | |
| 6,881,410 B2 | 4/2005 | Burnie et al. | |
| 6,908,994 B1 | 6/2005 | Rich et al. | |
| 6,913,907 B2 | 7/2005 | Choi et al. | |
| 6,939,543 B2 | 9/2005 | Fischer et al. | |
| 7,067,135 B2 | 6/2006 | Balaban | |
| 7,166,708 B2 | 1/2007 | Lees et al. | |
| 7,169,903 B2 | 1/2007 | Schuman et al. | |
| 7,195,763 B2 | 3/2007 | Xu et al. | |
| 7,250,494 B2 | 7/2007 | Stinson et al. | |
| 7,291,343 B2 | 11/2007 | Fattom et al. | |
| 7,323,179 B2 | 1/2008 | Balaban | |
| 7,410,647 B2 | 8/2008 | Foster et al. | |
| 7,449,189 B2 | 11/2008 | Fattom et al. | |
| 7,452,533 B2 | 11/2008 | Walsh et al. | |
| 7,534,857 B2 | 5/2009 | Balaban | |
| 7,615,616 B2 | 11/2009 | Hook et al. | |
| 2002/0122809 A1 | 9/2002 | Pier et al. | |
| 2003/0113350 A1 | 6/2003 | Fattom et al. | |
| 2003/0119101 A1 | 6/2003 | Burnie et al. | |

(Continued)

FOREIGN PATENT DOCUMENTS

| | | |
|---|---|---|
| DE | 102006053385 A1 | 5/2008 |
| EP | 0305279 B1 | 3/1995 |
| WO | 98/01154 | 1/1998 |
| WO | 98/50554 | 11/1998 |
| WO | 99/08705 | 2/1999 |
| WO | 99/18996 | 4/1999 |
| WO | 99/32133 | 7/1999 |
| WO | 00/68242 | 11/2000 |
| WO | 01/98499 A1 | 12/2001 |
| WO | 02/090502 A2 | 11/2002 |

(Continued)

OTHER PUBLICATIONS

Cipolla, Carbohydrate Chemistry: State of the Art and Challenges for Drug Development, World Scientific, Jul. 23, 2015, pp. 321-322.*

(Continued)

*Primary Examiner* — Layla Berry
(74) *Attorney, Agent, or Firm* — Anna C. Chau

(57) ABSTRACT

The invention relates to novel saccharides and uses thereof. In one aspect, the invention relates to a saccharide having a legionaminic acid moiety, a N-acetylgalactosamine moiety, a galactose moiety, and a glucose moiety. In another aspect, the invention relates to a saccharide having an altruronic acid moiety, a fucose moiety, and a glucose moiety. In yet another aspect, the invention relates to a saccharide having a repeating unit of a glycerol phosphate moiety and a glucose moiety, wherein the saccharide is from *Enterococcus faecium*. In a further aspect, the invention relates to a saccharide having a repeating unit of -6-β-D-Fruf-2, wherein Fru is a fructose moiety, wherein the saccharide is from *Enterococcus faecium*. In another aspect, the invention relates to an isolated antibody or fragment thereof that specifically binds to a saccharide described herein and uses thereof.

14 Claims, 15 Drawing Sheets

(56) References Cited

U.S. PATENT DOCUMENTS

| | | |
|---|---|---|
| 2003/0186275 A1 | 10/2003 | Foster et al. |
| 2003/0190320 A1 | 10/2003 | Speziale et al. |
| 2003/0224000 A1 | 12/2003 | Kokai-Kun et al. |
| 2003/0228322 A1 | 12/2003 | Schuman et al. |
| 2004/0009937 A1 | 1/2004 | Chen et al. |
| 2004/0043003 A1 | 3/2004 | Chen et al. |
| 2004/0101919 A1 | 5/2004 | Hook et al. |
| 2005/0075298 A1 | 4/2005 | Chen et al. |
| 2005/0123511 A1 | 6/2005 | McCreavy et al. |
| 2005/0180986 A1 | 8/2005 | Rich et al. |
| 2005/0256299 A1 | 11/2005 | Foster et al. |
| 2006/0140979 A1 | 6/2006 | Foster et al. |
| 2006/0165690 A1 | 7/2006 | Heath et al. |
| 2006/0165716 A1 | 7/2006 | Telford et al. |
| 2006/0252691 A1 | 11/2006 | Balaban |
| 2007/0009569 A1 | 1/2007 | Balaban |
| 2007/0021600 A1 | 1/2007 | Doucette-Stamm |
| 2007/0053920 A1 | 3/2007 | Heath et al. |
| 2008/0014202 A1 | 1/2008 | Schuman et al. |
| 2008/0019976 A1 | 1/2008 | Stinson et al. |
| 2008/0057065 A1 | 3/2008 | Foster |
| 2008/0152701 A1 | 6/2008 | Balaban |
| 2008/0175856 A1 | 7/2008 | Meinke et al. |
| 2008/0219960 A1 | 9/2008 | Groot et al. |
| 2008/0219976 A1 | 9/2008 | Balaban |
| 2008/0260773 A1 | 10/2008 | Del Giudice |
| 2008/0311108 A1 | 12/2008 | Foster et al. |
| 2009/0117135 A1 | 5/2009 | Heath et al. |
| 2010/0055112 A1 | 3/2010 | Hubner et al. |
| 2010/0330125 A1 | 12/2010 | Monteiro et al. |
| 2011/0212125 A1 | 9/2011 | Robbins et al. |

FOREIGN PATENT DOCUMENTS

| | | |
|---|---|---|
| WO | 03/011899 A2 | 2/2003 |
| WO | 03/048371 A2 | 6/2003 |
| WO | 03/059259 A2 | 7/2003 |
| WO | 03/063772 A2 | 8/2003 |
| WO | 03/063785 A2 | 8/2003 |
| WO | 03/063786 A2 | 8/2003 |
| WO | 03/064607 A2 | 8/2003 |
| WO | 03/072607 A1 | 9/2003 |
| WO | 2004/052396 A1 | 6/2004 |
| WO | 2004/064864 A1 | 8/2004 |
| WO | 2004/106367 A2 | 12/2004 |
| WO | 2005/009396 A2 | 2/2005 |
| WO | 2005/105845 A2 | 11/2005 |
| WO | 2006/065137 A2 | 6/2006 |
| WO | 2006/067632 A2 | 6/2006 |
| WO | 2006/078318 A2 | 7/2006 |
| WO | 2006/100430 A2 | 9/2006 |
| WO | 2008/058706 A2 | 5/2008 |
| WO | 2009/010877 A2 | 1/2009 |
| WO | 2009/013443 A1 | 1/2009 |
| WO | 2010/089340 A2 | 8/2010 |
| WO | 2011/062615 A1 | 5/2011 |
| WO | 2011/088843 A1 | 7/2011 |
| WO | 2011/133227 A2 | 10/2011 |
| WO | 2011/138361 A1 | 11/2011 |

OTHER PUBLICATIONS

Sawardeker, J.S., et al., "Quantitative Determination of Monosaccharides as Their Alditol Acetates by Gas Liquid Chromatography", Analytical Chemistry, 37(12):1602-1604 (1965).

Weigel et al, "Genetic Analysis of a High-Level Vancomycin-Resistant Isolate of Staphylococcus aureus", Science 302:1569-1571 (2003).

Werner et al, "Emergence and Spread of Vancomycin Resistance Among Enterococci in Europe", Eurosurveillance 13(47):1-11 (2008).

Willems et al, "Global Spread of Vancomycin-resistant Enterococcus faecium from Distinct Nosocomial Genetic Complex", Emerging Infectious Diseases 11(6):821-828 (2005).

Xia et al, "The wall teichoic and lipoteichoic acid polymers of Staphylococcus aureus", International Journal of Medical Microbiology 300:148-154 (2010).

Anderson et al, "Staphylococcal Surgical Site Infections", Infectious Disease Clinics of North America 23(1):53-72 (2009).

Arduino et al, "Resistance of Enterococcus faecium to Neutrophil-Mediated Phagocytosis", Infection and Immunity 62(12):5587-5594 (1994).

Batta et al, "Conformational stabilization of the altruronic acid residue in the O-specific polysaccharide of Shigella sonnei/Plesiomonas shigelloides", Carbohydrate Research 305:93-99 (1998).

Bejuk et al, "Evaluation of phenotypic characteristics for differentiation of enterococcal species using an example based algorithm", Diagnostic Microbiology and Infectious Disease 38:201-205 (2000).

Black, et al., "ADP-Ribosyltransferase Activity of Pertussis Toxin and Immunomodulation by Bordetella pertussis", Science, 240:656-659 (1988).

Bourgogne et al, "EbpR Is Important for Biofilm Formation by Activating Expression of the Endocarditis and Biofilm-Associated Pilus Operon (ebpABC) of Enterococcus faecalis OG1RF", Journal of Bacteriology 189(17):6490-6493 (2007).

Ciucanu et al, "A Simple and Rapid Method for the Permethylation of Carbohydrates", Carbohydrate Research 131:209-217 (1984.

Dische et al, "A Specific Color Reaction of Methylpentoses and a Spectrophotometric Micromethod for Their Determination", Journal of Biological Chemistry 175(2):595-603 (1948).

Fabretti et al, "Alanine Esters of Enterococcal Lipoteichoic Acid Play a Role in Biofilm Formation and Resistance to Antimicrobial Peptides", Infection and Immunity 74(7):4164-4171 (2006).

Glaze et al, "Biosynthesis of CMP-N,N'-Diacetyllegionaminic Acid from UDP-N,N'-Diacetylbacillosamine in Legionella pneumophila" Biochemistry 47:3272-3282 (2008).

Hall et al, "Monoclonal antibodies recognizing the Enterococcus faecalis collagen-binding MSCRAMM Ace: Conditional expression and binding analysis", Microbial Pathogenesis 43:55-66 (2007).

Hancock et al, "The capsular polysaccharide of Enterococcus faecalis and its relationship to other polysaccharides in the cell wall", PNAS 99(3):1574-1579 (2002).

Hendrickx et al, "Five Genes Encoding Surface-Exposed LPXTG Proteins Are Enriched in Hospital-Adapted Enterococcus faecium Clonal Complex 17 Isolates", Journal of Bacteriology 189(22):8321-8332 (2007).

Hendrickx et al, "SgrA, a Nidogen-Binding LPXTG Surface Adhesin Implicated in Biofilm Formation, and EcbA, a Collagen Binding MSCRAMM, Are Two Novel Adhesins of Hospital-Acquired Enterococcus faecium", Infection and Immunity 77(11):5097-5106 (2009).

Hermansson et al, "Structural studies of the capsular polysaccharide from Aerococcus viridans var. homari.", Carbohydrate Research 208:145-152 (1990).

Hestrin, "The Reaction of Acetylcholine and Other Carboxylic Acid Derivatives With Hydroxylamine, and its Analytical Application", Journal of Biological Chemistry 180(1):249-261 (1949).

Holst et al, "Microbial Polysaccharide Structures" Comprehensive Glycoscience: From Chemistry and Systems Biology, vol. 1: Introduction to Glycoscience. Synthesis of Carbohydrates; Kamerling, Johannis P. (Ed.), Amsterdam: Elsevier; pp. 123-179 (2007).

Hsu et al, "Immunochemical characterization of polysaccharide antigens from six clinical strains of Enterococci", BMC Microbiology 6(62):1-9 (2006).

Hufnagel et al, "Opsonophagocytic assay as a potentially useful tool for assessing safety of enterococcal preparations", International Journal of Food Microbiology 88:263-267 (2003).

Hufnagel et al, "Serological and Genetic Diversity of Capsular Polysaccharides in Enterococcus faecalis", Journal of Clinical Microbiology 42(6):2548-2557 (2004).

(56) References Cited

OTHER PUBLICATIONS

Knirel et al, "5,7-Diamino-3,5,7,9-Tetradeoxynon-2-Ulosonic Acids in Bacterial Glycopolymers: Chemistry and Biochemistry", Advances in Carbohydrate Chemistry and Biochemistry 58:371-417 (2003).
Koch et al, "Enterococcal infections: host response, therapeutic, and prophylactic possibilities", Vaccine 22:822-830 (2004).
Kooistra et al, "Epitope mapping of the O-chain polysaccharide of Legionella pneumophila serogroup 1 lipopolysaccharide by saturation-transfer-difference NMR spectroscopy", European Journal of Biochemistry 269(2):573-582 (2002).
Leavis et al, "Insertion Sequence-Driven Diversification Creates a Globally Dispersed Emerging Multiresistant Subspecies of *E faecium*", PLoS Pathogens 3(1):75-96 (2007).
Leendertse et al, "Neutrophils Are Essential for Rapid Clearance of Enterococcus faecium in Mice", Infection and Immunity 77(1):485-491 (2009).
Leendertse et al, "The Complement System Facilitates Clearance of Enterococcus faecium during Murine Peritonitis", The Journal of Infectious Diseases 201(4):544-552 (2010).
Lees et al, "Activation of soluble polysaccharides with 1-cyano-4-dimethylaminopyridinium tetrafluoroborate for use in protein-polysaccharide conjugate vaccines and immunological reagents", Vaccine 14(3):190-198 (1996).
Leung et al, "Efficient synthesis and protein conjugation of β-(1→6)-D-N-acetylglucosamine oligosaccharides from the polysaccharide intercellular adhesin", Carbohydrate Research 344(5):570-575 (2009).
Li et al, "Structural and genetic characterization of the O-antigen of *Escherichia coli* O161 containing a derivative of a higher acidic domino sugar, legionaminic acid", Carbohydrate Research 345(11):1581-1587 (2010).
Maclean et al, "Characterization of the lipopolysaccharide O-antigen of Cronobacter turicensis HPB3287 as a polysaccharide containing a 5,7-diacetamido-3,5,7,9-tetradeoxy-D-glycero-D-galacto-non-2-ulosonic acid (legionaminic acid) residue", Carbohydrate Research 346(16):2589-2594 (2011).
Matulova et al, "NMR structural study of fructans produced by *Bacillus* sp. 3B6, bacterium isolated in cloud water", Carbohydrate Research 346(4):501-507 (2011).
Mazmanian et al, "The love-hate relationship between bacterial polysaccharides and the host immune system", Nature Reviews—Immunology 6(11):849-858 (2006).
McDonald et al, "Co-Infection or Co-Colonization With Vancomycin-Resistant Enterococci and Methicillin-Resistant *Staphylococcus aureus* in a Network of Community Hospitals", Infection Control and Hospital Epidemiology 25(8):622 (2004).
Nallapareddy et al, "Diversity of ace, a Gene Encoding a Microbial Surface Component Recognizing Adhesive Matrix Molecules, from Different Strains of Enterococcus faecalis and Evidence for Production of Ace during Human Infections", Infection and Immunity 68(9):5210-5217 (2000).
Nallapareddy et al, "Endocarditis and biofilm-associated pili of Enterococcus faecalis", The Journal of Clinical Investigation 116(10):2799-2807 (2006).
Navarre et al, "Surface proteins of Gram-Positive Bacteria and Mechanisms of Their Targeting to the Cell Wall Envelope", Microbiology and Molecular Biology Reviews 63(1):174-229 (1999).
Palmer et al, "High-Quality Draft Genome Sequences of 28 *Enterococcus* sp. Isolates", Journal of Bacteriology 192(9):2469-2470 (2010).
Pappenheimer, et al., "An Immunological Study of the Diphtheria Toxin Molecule", Immunochemistry, 9:891-906 (1972).
PCT International Search Report and Written Opinion for PCT/IB2013/055452 dated Oct. 31, 2013.
Rakita et al, "Specific antibody promotes opsonization and PMN-mediated killing of phagocytosis-resistant Enterococcus faecium", FEMS Immunology and Medical Microbiology 28(4):291-299 (2000).
Rice, "Antimicrobial Resistance in Gram-Positive Bacteria", The American Journal of Medicine 119(6A):S11-S19 (2006).
Roberts, "The Biochemistry and Genetics of Capsular Polysaccharide Production in Bacteria", Annual Review of Microbiology 50:285-315 (1996).
Sava et al, "Pathogenesis and immunity in enterococcal infections", Clinical Microbiology and Infection 16(6):533-540 (2010).
van Schaik et al, "Pyrosequencing-based comparative genome analysis of the nosocomial pathogen Enterococcus faecium and identification of a large transferable pathogenicity island", BMC Genomics 11(239):1-18 (2010).
St. Swierzko et al, "Structural and serological studies of the O-specific polysaccharide of the bacterium Proteus mirabilis O10 containing L-altruronic acid, a new component of O-antigens", FEBS Letters 398(2-3):297-302 (1996).
Teng et al, "An Enterococcus faecium Secreted Antigen, SagA, Exhibits Broad-Spectrum Binding to Extracellular Matrix Proteins and Appears Essential for E. faecium Growth", Infection and Immunity 71(9):5033-5041 (2003).
Theilacker et al, "Rationale for the development of immunotherapy regimens against enterococcal infections", Vaccine 22(Suppl 1):S31-S38 (2004).
Theilacker et al, "Opsonic Antibodies to Enterococcus faecalis Strain 12030 are Directed against Lipoteichoic Acid", Infection and Immunity 74(10):5703-5712 (2006).
Trevelyan et al, "Determination of Yeast Carbohydrates with the Anthrone Reagent", Nature 170(4328):626-627 (1952).
Weidenmaier et al, "Teichoic acids and related cell-wall glycopolymers in Gram-positive physiology and host interactions", Nature Reviews. Microbiology 6(4):276-287 (2008).

\* cited by examiner

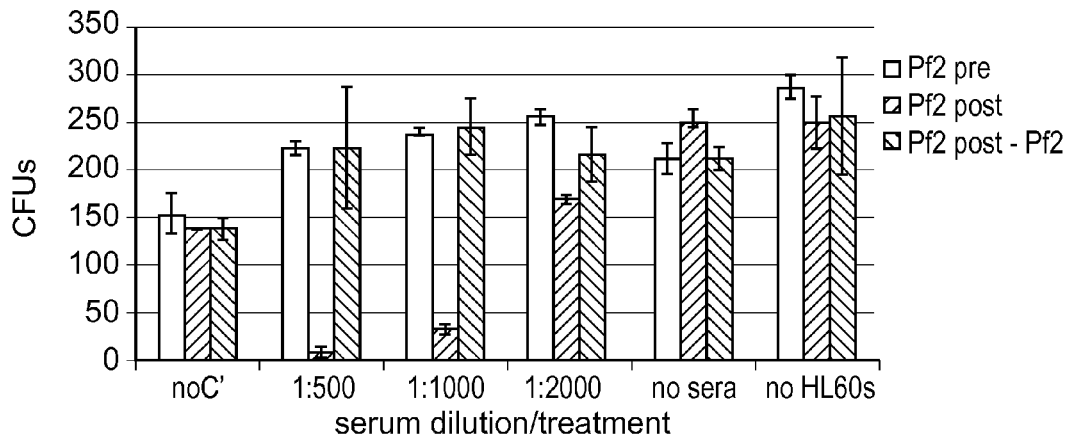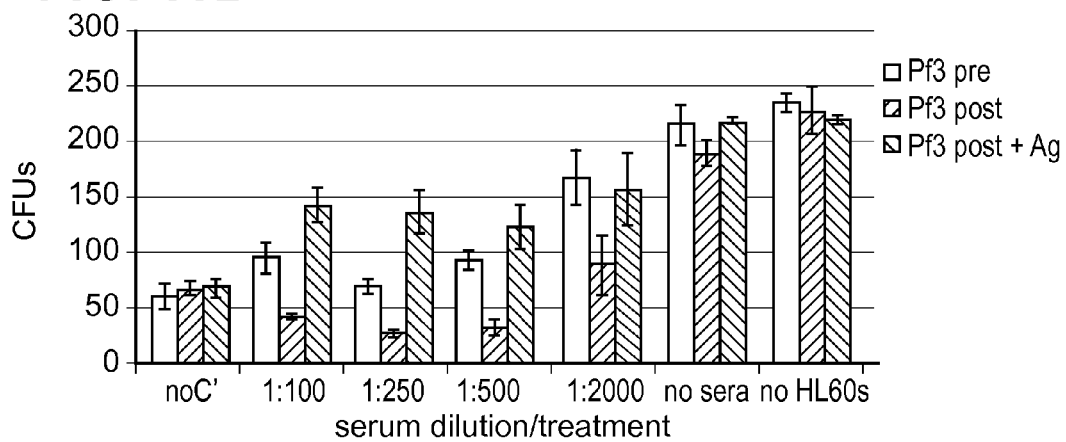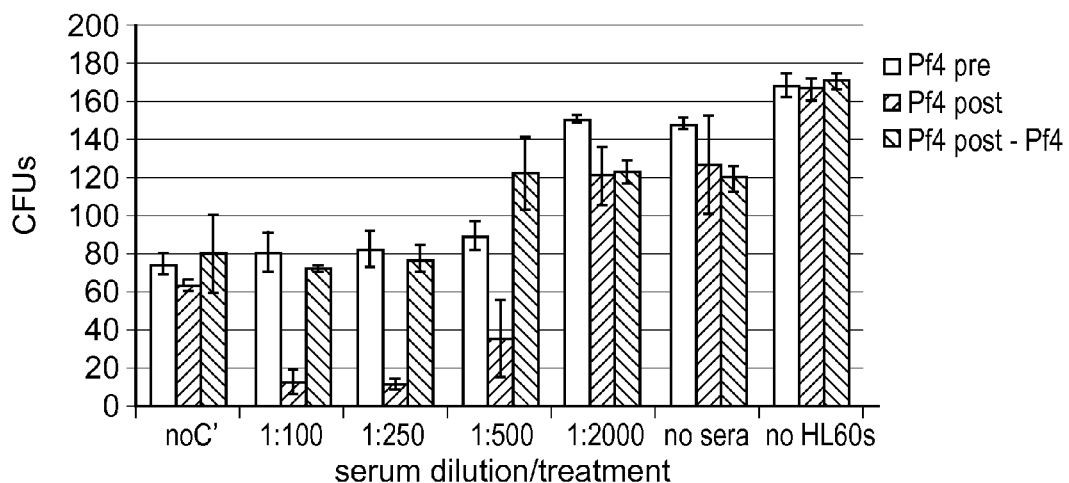

FIG. 15A  Pf4 - Formula (I)
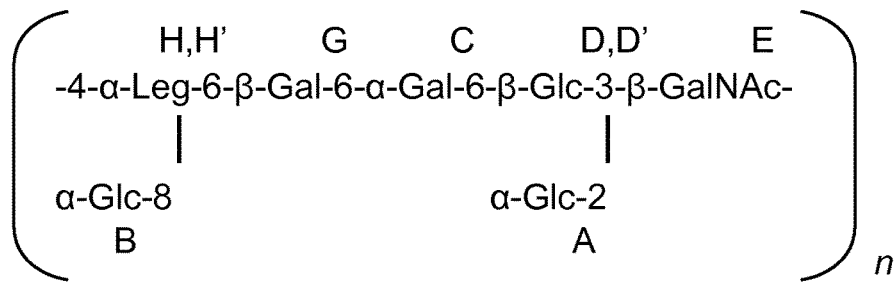
FIG. 15B  Pf2 - Formula (II)
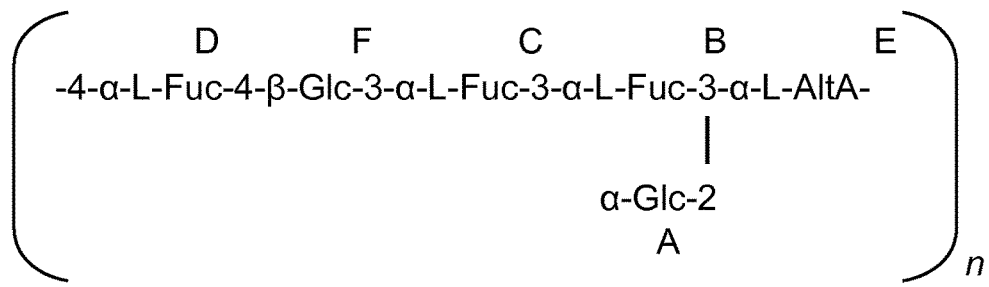
FIG. 15C
Pf3 - Formula (III)
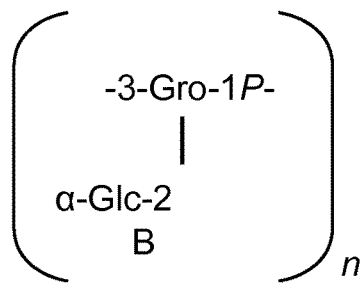
FIG. 15D
Pf3 - Formula (IV)
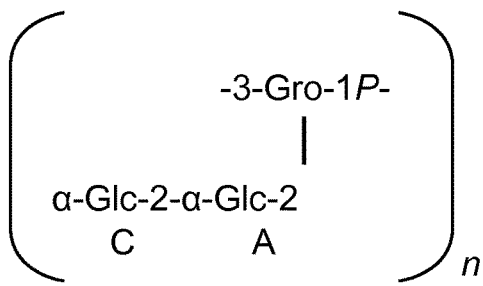
FIG. 15E
Pf1
((2→6)-beta-D-fructofuranan or 6-β-D-Fru*f*-2)

SACCHARIDES AND USES THEREOF

CROSS-REFERENCE TO RELATED APPLICATIONS

The present application is a national phase application under 35 U.S.C. §371 of International Application No. PCT/IB2013/055452, filed Jul. 3, 2013, which claims the benefit of U.S. Provisional Patent Application 61/672,221, filed Jul. 16, 2012. All of the foregoing applications are hereby incorporated by reference in their entireties.

FIELD OF THE INVENTION

The present invention relates to saccharides and uses thereof.

BACKGROUND OF THE INVENTION

Infections by Gram-positive bacteria have been of growing medical concern due to an increased incidence of infection observed in health care institutions world-wide. Among the most problematic Gram-positive bacteria with regard to human pathology are Staphylococcal species, Enterococcal species, and Streptococcal species, among others. Even more troubling is the increasing trend toward antibiotic resistance shown by these and other Gram-positive bacteria, such as, for example, methicillin-resistant *Staphylococcus aureus* (MRSA) and vancomycin-resistant enterococci (VRE). Accordingly, there remains a need for compositions and methods to prevent and treat Gram-positive bacterial infections.

SUMMARY OF THE INVENTION

To meet these and other needs, the present invention relates to novel saccharides, antibodies thereto, and uses thereof. The following clauses describe some aspects and embodiments of the invention.

In one aspect, the invention relates to a polysaccharide including a legionaminic acid moiety, a N-acetylgalactosamine moiety, a galactose moiety, and a glucose moiety. In one embodiment, the legionaminic acid moiety is linked to the glucose moiety. In another embodiment, the legionaminic acid moiety is linked to the galactose moiety. In yet another embodiment, the legionaminic acid moiety is linked to the N-acetylgalactosamine moiety. In one embodiment, the legionaminic acid moiety, N-acetylgalactosamine moiety, galactose moiety, and glucose moiety are in a molar ratio of 1:1:2:3. In one embodiment, the polysaccharide includes a repeating unit of a structure represented by:

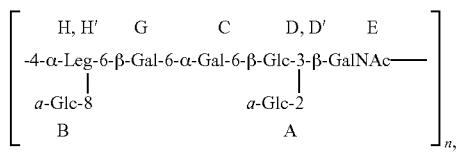

wherein Leg is a legionaminic acid moiety, Gal is a galactose moiety, Glc is a glucose moiety, and GalNAc is a N-acetylgalactosamine moiety, and wherein n is an integer from 1 to 1000. In one embodiment, n is between about 40 and about 60. In one embodiment, the molecular weight of the polysaccharide is between about 60 kDa and about 100 kDa. In one embodiment, the polysaccharide has an NMR spectrum as shown in FIG. 7.

In one aspect, the invention relates to a polysaccharide including an altruronic acid moiety, a fucose moiety, and a glucose moiety. In one embodiment, the altruronic acid moiety is linked to the fucose moiety. In another embodiment, the fucose moiety is linked to a glucose moiety. In yet another embodiment, the altruronic acid moiety, fucose moiety, and glucose moiety are in a molar ratio of 1:4:2. In a further embodiment, the polysaccharide includes a repeating unit of a structure represented by:

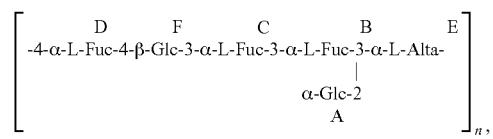

wherein Fuc is a fucose moiety, Glc is a glucose moiety, and AltA is an altruronic acid moiety, and wherein n is an integer from 1 to 1000. In one embodiment, n is between about 280 and about 300. In another embodiment, the molecular weight of the polysaccharide is between about 250 kDa and about 350 kDa. In one embodiment, the polysaccharide has an NMR spectrum as shown in FIG. 2.

In one aspect, the invention relates to a polysaccharide including a repeating unit of a glycerol phosphate moiety and a glucose moiety, wherein the polysaccharide is preferably an *Enterococcus faecium* TX0016 (DO; E1794) polysaccharide. In another aspect, the invention relates to a polysaccharide including a repeating unit of a glycerol phosphate moiety and a glucose moiety, wherein the polysaccharide is an *Enterococcus faecium* E0155 polysaccharide. In one embodiment, the repeating unit includes a structure represented by:

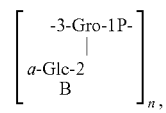

wherein Gro-1P is a glycerol phosphate moiety and Glc is a glucose moiety, and wherein n is an integer from 1 to 1000. In one embodiment, n is between about 80 to about 100. In another embodiment, the repeating unit includes a structure represented by:

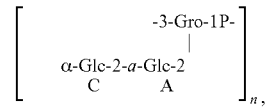

wherein Gro-1P is a glycerol phosphate moiety and Glc is a glucose moiety, and wherein n is an integer from 1 to 1000. In yet another embodiment, n is between about 80 to about 100. In a further embodiment, the molecular weight of the polysaccharide is between about 10 kDa and 20 kDa. In one embodiment, the polysaccharide has an NMR spectrum as shown in FIG. 6.

In one aspect, the invention relates to a polysaccharide including a repeating unit of -6-β-D-Fruf-2, wherein Fru is a fructose moiety, wherein the polysaccharide is preferably an *Enterococcus faecium* TX0016 (DO; E1794) polysaccharide. In another aspect, the invention relates to a polysaccharide including a repeating unit of -6-β-D-Fruf-2, wherein Fru is a fructose moiety, wherein the polysaccharide is an *Enterococcus faecium* E0155 polysaccharide. In one embodiment, the repeating unit includes [-6-β-D-Fruf-2]n, wherein Fru is a fructose moiety, and wherein n is an integer from 1000 to 100,000. In one embodiment, n is between about 35,000 to about 45,000. In one embodiment, the molecular weight of the polysaccharide is between about 10,000 kDa and 20,000 kDa. In one embodiment, the polysaccharide has an NMR spectrum as shown in FIG. 1.

In one embodiment, the polysaccharide is a cell surface polysaccharide. In another embodiment, the polysaccharide is a capsular polysaccharide.

In one embodiment, the polysaccharide is immunogenic. In another embodiment, the polysaccharide is capable of inducing an immune response with opsonic activity. In yet a further embodiment, the polysaccharide is capable of inducing a bactericidal immune response.

In one embodiment, the polysaccharide is isolated. In another embodiment, the polysaccharide is synthetically synthesized.

In one embodiment, the polysaccharide is branched.

In one embodiment, the polysaccharide is a Gram-positive coccal polysaccharide. In one embodiment, the polysaccharide is an *Enterococcus* polysaccharide. In one embodiment, the polysaccharide is an *Enterococcus faecium* polysaccharide. In one embodiment, the polysaccharide is preferably an *Enterococcus faecium* TX0016 (DO; E1794) polysaccharide. In one embodiment, the polysaccharide is an *Enterococcus faecium* E0155 polysaccharide.

In one embodiment, the polysaccharide is a cell surface polysaccharide. In another embodiment, the polysaccharide is a capsular polysaccharide. In one embodiment, the polysaccharide is immunogenic. In another embodiment, the polysaccharide is capable of inducing an immune response with opsonic activity. In yet a further embodiment, the polysaccharide is capable of inducing a bactericidal immune response. In one embodiment, the polysaccharide is isolated. In another embodiment, the polysaccharide is synthetically synthesized.

In one embodiment, the polysaccharide is conjugated to a carrier protein. In another embodiment, the carrier protein is a protein selected from the group consisting of of a diphtheria toxoid, CRM197, a tetanus toxoid, a cholera toxoid, a pertussis toxoid, an *E. coli* heat labile toxoid (LT), a pneumolysin toxoid, pneumococcal surface protein A (PspA), pneumococcal adhesin protein A (PsaA), a C5a peptidase from *Streptococcus*, *Haemophilus influenzae* protein D, ovalbumin, keyhole limpet haemocyanin (KLH), bovine serum albumin (BSA), purified protein derivative of tuberculin (PPD), and a *Pseudomonas* exotoxin, or its derivatives. In a further embodiment, the carrier protein is $CRM_{197}$.

In one aspect, the invention relates to a composition including an effective amount of a polysaccharide and a pharmaceutically acceptable diluent, wherein the polysaccharide includes a legionaminic acid moiety, a N-acetylgalactosamine moiety, a galactose moiety, and a glucose moiety. In one embodiment, the composition is immunogenic.

In one aspect, the invention relates to a composition including an effective amount of a polysaccharide and a pharmaceutically acceptable diluent, wherein the polysaccharide includes an altruronic acid moiety, a fucose moiety, and a glucose moiety. In one embodiment, the composition is immunogenic.

In one aspect, the invention relates to a composition including an effective amount of a polysaccharide and a pharmaceutically acceptable diluent, wherein the polysaccharide includes a repeating unit of a glycerol phosphate moiety and a glucose moiety, wherein the polysaccharide is preferably an *Enterococcus faecium* TX0016 (DO; E1794) polysaccharide. In one embodiment, the composition is immunogenic.

In another aspect, the invention relates to a composition including an effective amount of a polysaccharide and a pharmaceutically acceptable diluent, wherein the polysaccharide includes a repeating unit of a glycerol phosphate moiety and a glucose moiety, wherein the polysaccharide is an *Enterococcus faecium* E0155 polysaccharide. In one embodiment, the composition is immunogenic.

In yet another aspect, the invention relates to a composition including an effective amount of a polysaccharide and a pharmaceutically acceptable diluent, wherein the polysaccharide includes a repeating unit of -6-β-D-Fruf-2, wherein Fru is a fructose moiety, and wherein the polysaccharide is preferably an *Enterococcus faecium* TX0016 (DO; E1794) polysaccharide. In one embodiment, the composition is immunogenic.

In a further aspect, the invention relates to a composition including an effective amount of a polysaccharide and a pharmaceutically acceptable diluent, wherein the polysaccharide includes a repeating unit of -6-β-D-Fruf-2, wherein Fru is a fructose moiety, and wherein the polysaccharide is an *Enterococcus faecium* E0155 polysaccharide. In one embodiment, the composition is immunogenic.

In one aspect, the invention relates to a composition including at least two polysaccharides described herein. In one embodiment, the composition includes at least three polysaccharides described herein. In another embodiment, each polysaccharide is conjugated to a carrier molecule. In yet another embodiment, the carrier molecule is a carrier protein. In a further embodiment, the carrier protein is a protein selected from the group consisting of of a diphtheria toxoid, $CRM_{197}$, a tetanus toxoid, a cholera toxoid, a pertussis toxoid, an *E. coli* heat labile toxoid (LT), a pneumolysin toxoid, pneumococcal surface protein A (PspA), pneumococcal adhesin protein A (PsaA), a C5a peptidase from *Streptococcus*, *Haemophilus influenzae* protein D, ovalbumin, keyhole limpet haemocyanin (KLH), bovine serum albumin (BSA), purified protein derivative of tuberculin (PPD), and a *Pseudomonas* exotoxin, or its derivatives. In one embodiment, the carrier protein is $CRM_{197}$. In another embodiment, the composition further includes a pharmaceutically acceptable diluent.

In one aspect, the invention relates to a method of inducing an immune response in a mammal including administering an effective amount of a polysaccharide described herein. In one embodiment, the immune response is against a Gram-positive coccus. In another embodiment, the immune response is against *Enterococcus*.

In one aspect, the invention relates to a method of inducing an immune response in a mammal including administering an effective amount of a composition, which includes a polysaccharide described herein. In one embodiment, the immune response is against a Gram-positive coccus. In another embodiment, the immune response is against *Enterococcus*.

In one aspect, the invention relates to a method for producing an isolated polysaccharide described herein, including culturing a Gram positive coccus bacterium having an ability to produce the polysaccharide; and isolating the polysaccharide produced by the bacterium. In one embodiment, the Gram-positive coccus is *Enterococcus*. In another embodiment, the Gram-positive coccus is *Enterococcus faecium*. In yet another preferred embodiment, the Gram-positive coccus is *Enterococcus faecium* TX0016 (DO; E1794). In one embodiment, the Gram-positive coccus is *Enterococcus faecium* E0155.

In one aspect, the invention relates to a method of detecting a Gram-positive coccus in a sample including contacting a polysaccharide described herein; detecting an antibody-antigen conjugate complex, wherein the presence of the antibody-antigen complex indicates the presence of a Gram-positive coccus in the sample.

In one aspect, the invention relates to an antibody or fragment thereof that specifically binds to a polysaccharide described herein. In one embodiment, the antibody or fragment thereof is isolated. In one aspect, the invention relates to a composition including an isolated antibody or fragment thereof described herein. In another aspect, the invention relates to a method of detecting a Gram-positive coccus in a sample including contacting an antibody described herein; detecting an antibody-antigen conjugate complex, wherein the presence of the antibody-antigen complex indicates the presence of a Gram-positive coccus in the sample. In a further aspect, the invention relates to a method of producing an isolated antibody or antibody fragment thereof including administering an effective amount of a polysaccharide described herein to a mammal; and isolating the antibody or fragment thereof from the mammal.

BRIEF DESCRIPTION OF THE DRAWINGS

FIG. 11 shows opsonophagocytic activity of antisera induced by *E. faecium* Pf2-Pf4 polysaccharides against strains TX0016(DO) and E0155 (Freiburg). Panel A shows OPA activity of Pf2 sera versus TX0016 (DO) strain is reversed by 20 µg/ml Pf2. Panel B shows partial OPA activity of Pf3 sera versus E0155 (Freiburg) is reversed by 20 µg/ml Pf3. Panel C shows OPA activity of Pf4 sera versus E0155 (Freiburg) is reversed by 20 µg/ml Pf4. The label "no C" in Panel A and Panel B of FIG. 11 refers to the absence of complement.

FIG. 15 shows structures representing A. a saccharide including a legionaminic acid moiety, as shown by formula (I) (Pf4); B. a Pf2 saccharide, as shown by formula (II); C. a Pf3 saccharide, as shown by formula (III) and D. formula (IV); and E. a saccharide having a levan moiety (Pf1).

DETAILED DESCRIPTION OF THE INVENTION

Figure 1:
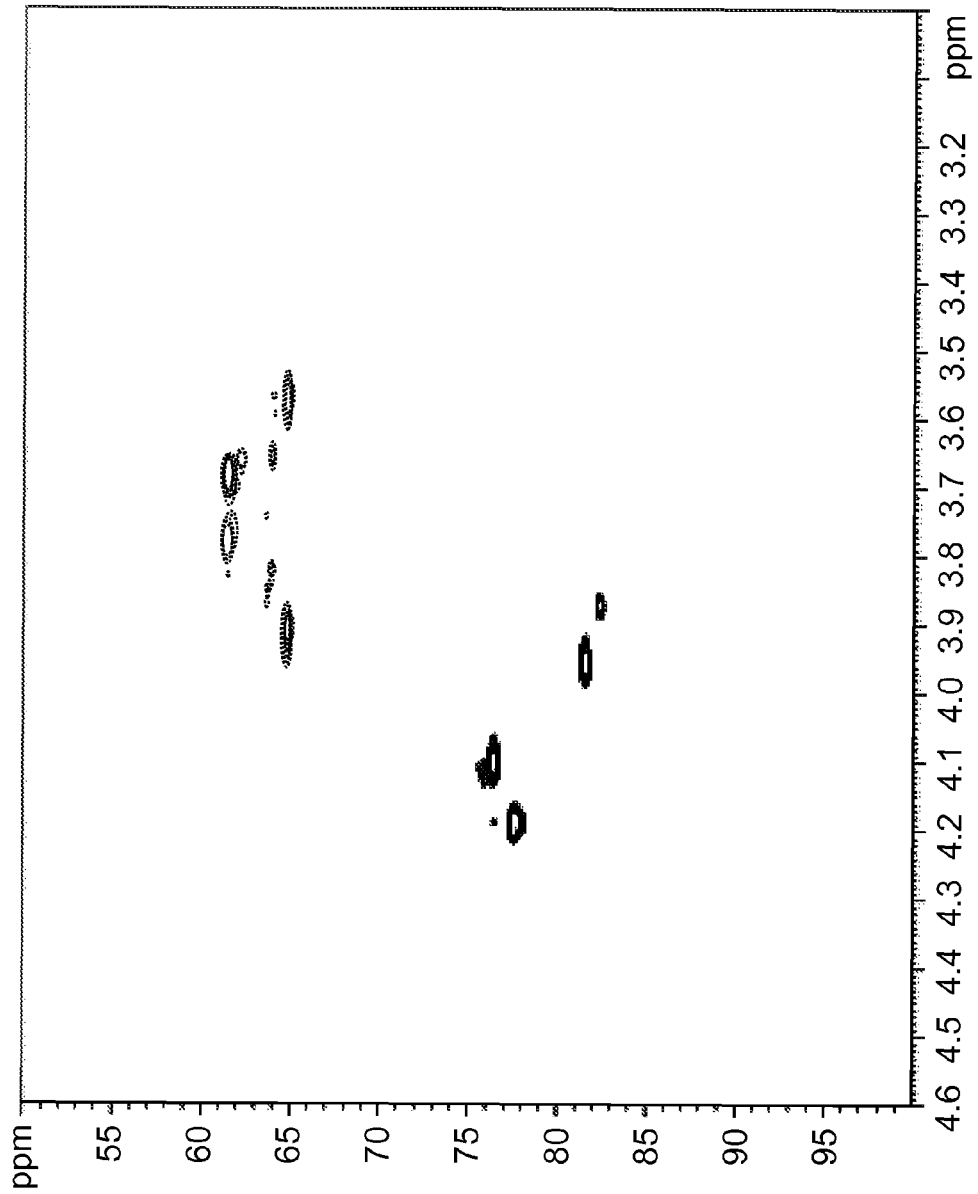
FIG. 1 shows a $^1$H-$^{13}$C HSQC spectrum of the polysaccharide Pf1.

The inventors surprisingly discovered and identified at least four saccharides, designated Pf1, Pf2, Pf3, and Pf4 herein. The Pf1 saccharide includes a levan moiety. The Pf2 saccharide includes an altruronic acid moiety. The Pf3 saccharide includes a glycerol phosphate moiety. The Pf4 saccharide includes a legionaminic acid moiety.

Any of the saccharides described herein may be isolated from a Gram-positive coccus. Gram-positive cocci bacteria are chemoorganotrophic, mesophilic, non-spore-forming cocci that stain Gram positive. Individual organisms have a common spherical morphological characteristic and can form clumps or chains. Examples of Gram-positive cocci include *Staphylococcus* species, *Enterococcus* species, and *Streptococcus* species.

In one embodiment, the saccharide is isolated from an *Enterococcus* bacterium. Exemplary *Enterococcus* species include *E. avium*, *E. casseliflavus*, *E. dispar*, *E. durans*, *E. faecalis*, *E. faecalis* variant, *E. faecium*, *E. flavescens*, *E. gallinarum*, *E. hirae*, *E. mundtii* and *E. raffinosus*.

In one embodiment, the saccharide is isolated from *Enterococcus faecium*. The polysaccharide may be isolated from any strain of *E. faecium*. *E. faecium* strains include, for example, strain E1162 (genome GenBank accession number ABQJ00000000) and strain U0317 (genome GenBank accession number ABSW00000000), and strains listed below.

| Strain | Strain |
|---|---|
| E0510 | E1728 |
| E1760 | E1731 |
| E1679 (Genome GenBank accession number ABSC00000000) | E1794 (DO strain; TX0016 strain) (Genome GenBank accession number ACIY00000000) |
| E1644 | E1360 |
| E1716 | E1674 |

| Strain | Strain |
|---|---|
| E1717 | E1675 |
| E1441 | E1643 |
| E1435 | E1850 |
| E0734 | E0005 |
| E1652 | E0321 |
| E0745 | E0322 |
| E0470 | E0027 |
| E1340 | E1149 |
| E0013 | E1147 |
| E0300 | E0802 |
| E0155 | E0849 |
| E0161 | E1316 |
| E1132 | E1554 |
| E1263 | E1133 |
| E1250 | E1764 |
| E1283 | E1766 |
| E1284 | E1485 |
| E1734 | E1590 |
| E1467 | E0060 |
| E1500 | E0128 |
| E1737 | E0135 |
| E1463 | E1002 |
| E1499 | E1039 (Genome GenBank accession number ACOS00000000) |
| E1735 | E0980 (Genome GenBank accession number ABQA00000000) |
| E0380 | E1071 (Genome GenBank accession number ABQI00000000) |
| E1391 | E1759 |
| E1403 | E1628 |
| E1421 | E1630 |
| E1423 | E1573 |
| E0333 | E0172 |
| E1292 | E0211 |
| E1620 | E0466 |
| E1621 | E1574 |
| E1623 | E0463 |
| E1625 | E1607 |
| E1636 (Genome GenBank accession number ABRY00000000) | E1619 |
| E0073 | E1576 |
| E0125 | E1781 |
| E0772 | E0685 |
| E1172 | E0144 |
| E1302 | E0045 |
| E1307 | E0429 |
| E1308 | E1622 |
| E1721 | |

Additional examples of *E. faecium* strains include *E. faecium* 1,141,733 (genome GenBank accession number ACAZ00000000), 1,230,933 (genome GenBank accession number ACAS00000000), 1,231,408 (genome GenBank accession number ACBB00000000), 1,231,410 (genome GenBank accession number ACBA00000000), 1,231,501 (genome GenBank accession number ACAY00000000), 1,231,502 (genome GenBank accession number ACAX00000000), Com12 (genome GenBank accession number ACBC00000000), and Com15 (genome GenBank accession number ACBD00000000), which are also described in Palmer et al., *J Bacteriol.* 2010 May; 192(9): 2469-70. Yet another example of an *E. faecium* strain is E155 (Freiburg) or E0155 (Freiburg).

As used herein, "E155 (Freiburg)" or "E0155 (Freiburg)" refers to an *Enterococcus faecium* strain designated "E155" or "E0155" by the University of Freiburg.

As used herein, "E155" in the absence of "(Freiburg)" immediately thereafter refers to any *E. faecium* strain known in the art as an "E155" strain, such as, for example, an *E. faecium* E155 strain from the University of Utrect. Preferably, the term "E155" in the absence of "(Freiburg)" excludes the "E155" strain from the University of Freiburg.

As used herein, "E0155" in the absence of "(Freiburg)" immediately thereafter refers to any *E. faecium* strain known in the art as an "E0155" strain, such as, for example, an *E. faecium* E155 strain from the University of Utrect. Preferably, the term "E0155" in the absence of "(Freiburg)" excludes the "E0155" strain from the University of Freiburg.

The saccharides described herein may be isolated from the Gram-positive coccus by methods known in the art, including, for example, methods described herein. As used herein, "isolated" refers to being obtained from and separated from a particular source. The term "isolated" further refers to not being in its respective naturally occurring form, state, and/or environment. For example, "isolated from *Enterococcus*" refers to a matter that was obtained from and separated from an *Enterococcus* cell. The isolated saccharide is not naturally occurring.

Accordingly, in one aspect, the invention relates to a non-naturally occurring saccharide that includes a levan moiety (e.g., Pf1). In another aspect, the invention relates to a non-naturally occurring saccharide that includes an altruronic acid moiety (Pf2). In an additional aspect, the invention relates to a non-naturally occurring saccharide that includes a glycerol phosphate moiety (Pf3). In a further aspect, the invention relates to a non-naturally occurring saccharide that includes a legionaminic acid moiety (Pf4).

In one embodiment, the saccharide is purified. The term "purified" does not require absolute purity. For example, a purified saccharide, conjugate, or other active compound is one that is isolated in whole or in part from proteins, lipids, or other contaminants. Methods for purifying an isolated saccharide are known in the art, including, for example, methods described herein. The term "purified" may include synthetic saccharide preparations retaining artifacts of their synthesis or preparations that include some impurities, so long as the preparation exhibits reproducible saccharide characterization data, for example, molecular weight, carbohydrate residue content, carbohydrate linkage, chromatographic response, and/or immunogenic behavior.

Alternatively, in another embodiment of the invention, the saccharide is synthetic or chemically synthesized. The saccharide may be chemically synthesized according to conventional methods.

In yet another embodiment of the invention, the saccharide is prepared by expression in a surrogate host after cloning and expressing a biosynthetic pathway to produce the saccharide.

As used herein, the term "saccharide" refers to a single sugar moiety or monosaccharide unit as well as combinations of two or more single sugar moieties or monosaccharide units covalently linked to form disaccharides, oligosaccharides, and polysaccharides. The term "saccharide" may be used interchangeably with the term "carbohydrate." The saccharide may be linear or branched.

A "monosaccharide" as used herein refers to a single sugar residue in an oligosaccharide. The term "disaccharide" as used herein refers to a saccharide composed of two monosaccharide units or moieties linked together by a glycosidic bond.

In one embodiment, the saccharide is an oligosaccharide (OS). An "oligosaccharide" as used herein refers to a compound containing two or more monosaccharide units or moieties. Within the context of an oligosaccharide, an individual monomer unit or moiety is a monosaccharide which is, or can be, bound through a hydroxyl group to another monosaccharide unit or moiety. Oligosaccharides can be prepared by either chemical synthesis from protected single residue sugars or by chemical degradation of biologically produced polysaccharides. Alternatively, oligosaccharides may be prepared by in vitro enzymatic methods.

In a preferred embodiment, the saccharide is a polysaccharide (PS), which refers to a linear or branched polymer of at least 5 monosaccharide units or moieties. For clarity, larger number of repeating units, wherein n is greater than about 5, will be referred to herein as a polysaccharide.

In one embodiment of the invention, the polysaccharide is isolated from a bacterium. In another embodiment, the polysaccharide is chemically synthesized according to conventional methods. In yet another embodiment of the invention, the polysaccharide is prepared by expression in a surrogate host after cloning and expressing a biosynthetic pathway to produce the saccharide.

In one embodiment, the polysaccharide is a cell surface polysaccharide. A cell surface polysaccharide refers to a polysaccharide having at least a portion located on the outermost bacterial cell membrane or bacterial cell surface, including the peptidoglycan layer, cell wall, and capsule. Typically, a cell surface polysaccharide is associated with inducing an immune response in vivo. A cell surface polysaccharide may be a "cell wall polysaccharide" or a "capsular polysaccharide." A cell wall polysaccharide typically forms a discontinuous layer on the bacterial surface.

In one embodiment, the polysaccharide is a capsular polysaccharide. A capsular polysaccharide refers to a glycopolymer that includes repeating units of one or more monosaccharides joined by glycosidic linkages. A capsular polysaccharide typically forms a capsule-like layer around a bacterial cell.

In one embodiment, the saccharide is immunogenic. For example, the inventors discovered that each saccharide described herein is capable of inducing or eliciting an immune response. The term "immunogenic" refers to an ability to initiate, trigger, cause, enhance, improve, and/or augment a humoral and/or cell-mediated immune response in a mammal. In one embodiment, the mammal is a human, primate, rabbit, pig, mouse, etc.

In one embodiment, the saccharide described herein is capable of inducing opsonic activity. In another embodiment, the saccharide described herein is capable of inducing opsonic and phagocytic activity (e.g., opsonophagocytic activity).

Opsonic activity or opsonization refers to a process by which an opsonin (for example, an antibody or a complement factor) binds to an antigen (e.g., an isolated saccharide described herein), which facilitates attachment of the antigen to a phagocyte or phagocytic cell (e.g., a macrophage, dendritic cell, and polymorphonuclear leukocyte (PMNL). Some bacteria, such as, for example, encapsulated bacteria that are not typically phagocytosed due to the presence of the capsule, become more likely to be recognized by phagocytes when coated with an opsonic antibody. In one embodiment, the saccharide induces an immune response, such as, e.g., an antibody, that is opsonic. In one embodiment, the opsonic activity is against a Gram-positive coccus, preferably against a *Enterococcus* species, more preferably against at least one strain of *E. faecium*.

Phagocytic activity or phagocytosis refers to a process by which a phagocytic cell engulfs material and encloses the material in its cytoplasm. In one embodiment, the saccharide induces an immune response, such as, e.g., an antibody, that facilitates phagocytosis. In one embodiment, the phagocytic activity is against a Gram-positive coccus, preferably against a *Enterococcus* species, more preferably against at least one strain of *E. faecium*. For example, rabbit antibodies raised against an isolated saccharide described herein may be able to mediate opsonophagocytosis specifically of a strain expressing the saccharide in the presence of complement, as indicated, for example, by an in vitro phagocytosis assay.

In yet another embodiment, the saccharide described herein is capable of inducing a bactericidal immune response. In one embodiment, the bactericidal activity is against a Gram-positive coccus, preferably against an *Enterococcus* species, more preferably against at least one strain of *E. faecium*.

Methods for measuring opsonization, phagocytosis, and/or bactericidal activity are known in the art, such as, for example, by measuring reduction in bacterial load in vivo (e.g., by measuring bacteremia levels in mammals challenged with *Enterococcus*) and/or by measuring bacterial cell killing in vitro (e.g., an in vitro opsonophagocytic assay). In one embodiment, the saccharide is capable of inducing opsonic, phagocytic, and/or bactericidal activity as compared to an appropriate control, such as, for example, as compared to antisera raised against a heat-killed Gram-positive coccus.

Saccharide Including a Legionaminic Acid Moiety

In one aspect, the invention relates to a saccharide including a legionaminic acid moiety. Legionaminic acid (5,7-diacetamido-3,5,7,9-tetradeoxy-D-glycero-D-galacto-nonulosonic acid or Leg) is a nine-carbon α-keto acid having a molecular formula of $C_{13}H_{21}N_2O_8^-$. Legionaminic acid has a molecular weight of about 333 Da.

In one embodiment, the saccharide includes a legionaminic acid moiety and a N-acetylgalactosamine (GalNAc) moiety.

In one embodiment, the saccharide includes a legionaminic acid moiety and a galactose (Gal) moiety.

In one embodiment, the saccharide includes a legionaminic acid moiety and a glucose (Glc) moiety.

In one embodiment, the saccharide includes a legionaminic acid moiety, a N-acetylgalactosamine moiety, and a galactose moiety. In another embodiment, the saccharide includes a legionaminic acid moiety, a N-acetylgalactosamine moiety, and a glucose moiety.

In one embodiment, the saccharide includes a legionaminic acid moiety, a N-acetylgalactosamine moiety, a galactose moiety, and a glucose moiety. In a preferred arrangement of the saccharide, the legionaminic acid moiety is linked to a glucose moiety. In another preferred arrangement, a glucose moiety is linked to another glucose moiety. In some preparations, the saccharide further includes at least one unit of a rhamnose (Rha) moiety.

In one embodiment, the saccharide is a polysaccharide including a legionaminic acid moiety. In one embodiment, the polysaccharide includes a legionaminic acid moiety, a N-acetylgalactosamine moiety, a galactose moiety, and a glucose moiety. In a preferred arrangement of the polysaccharide, the legionaminic acid moiety is linked to a glucose moiety. In another preferred arrangement, a glucose moiety is linked to another glucose moiety. In one embodiment, the polysaccharide includes a legionaminic acid moiety, a N-acetylgalactosamine moiety, a galactose moiety, and a glucose moiety in a molar ratio of 1:1:2:3. In some preparations, the polysaccharide further includes at least one unit of a rhamnose (Rha) moiety.

In one embodiment, the saccharide has a molecular weight of at least about =, 1 kDa, 1.45 kDa, 1.5 kDa, 3 kDa, 10 kDa, or 20 kDa to at most about 5000 kDa, 2000 kDa, 1000 kDa, 900 kDa, 800 kDa, 700 kDa, 600 kDa, 500 kDa, 100 kDa, 90 kDa, 80 kDa, 70 kDa, 60 kDa. Any minimum value and any maximum value may be combined to define a range. For example, in one embodiment, the saccharide has a molecular weight of at least about 1 kDa to at most about 5000 kDa, preferably at least about 50 kDa to at most about 100 kDa. In one embodiment, the saccharide has a molecular weight of about 62.5 kDa. In another embodiment, the saccharide has a molecular weight of about 92.5 kDa.

The molecular weight or average molecular weight of a saccharide described herein refers to the weight of the saccharide as measured by a method known in the art, such as, for example, multi-angle laser light scattering (MALLS). It should be noted that the molecular weight of a given saccharide may vary depending factors such as, for example, pathway and environments of synthesis of the saccharide, the extraction conditions used to isolate the saccharide, the species from which the saccharide is isolated, and/or on location and time of harvest of the saccharide. Moreover, saccharides isolated and purified from natural sources may be heterogenous in size. Accordingly, the value for molecular weight may represent an average or median value for the molecular weight of the molecules in a particular population.

In one embodiment, the saccharide includes a structure represented by formula (I):

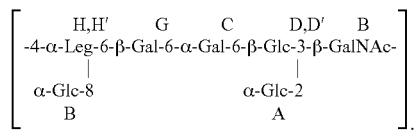

A saccharide that includes a structure represented by formula (I) has a molecular weight of at least about 1000 Da, preferably at least about 1400 Da, most preferably at least about 1456 Da.

In one embodiment, the saccharide including a structure represented by formula (I) is a polysaccharide. In one embodiment, the polysaccharide includes at least one repeating unit of a structure represented by formula (I):

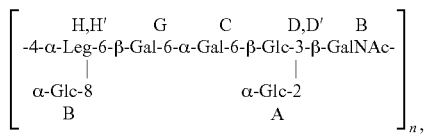

wherein n is any integer greater than or equal to 1.

As defined herein, "n" refers to the number of repeating units (represented in brackets) in a polysaccharide molecule. As is known in the art, in biological macromolecules, repeating structures may be interspersed with regions of imperfect repeats, such as, for example, missing branches. In addition, it is known in the art that polysaccharides isolated and purified from natural sources such as bacteria may be heterogenous in size and in branching. In such a case, n may represent an average or median value for n for the molecules in a population.

In one embodiment, n in formula (I) is an integer of at least 1, 2, 3, 4, 5, 10, 20, or 30 and at most 1000, 500, 400, 300, 200, 100, 90, 80, 70, 60, 50, or 40. Any minimum value and any maximum value may be combined to define a range. Exemplary ranges include, for example, at least 1 to at most 1000; at least 10 to at most 500; and at least 20 to at most 80. In one preferred embodiment, n is at least 35 to at most 55. For example, in one embodiment, n is 35, 36, 37, 38, 39, 40, 41, 42, 43, 44, 45, 46, 47, 48, or 49, most preferably 40. In another preferred embodiment, n is at least 55 to at most 75. For example, in one embodiment, n is 55, 56, 57, 58, 59, 60, 61, 62, 63, 64, 65, 66, 67, 68, or 69, most preferably 60.

Figure 7:
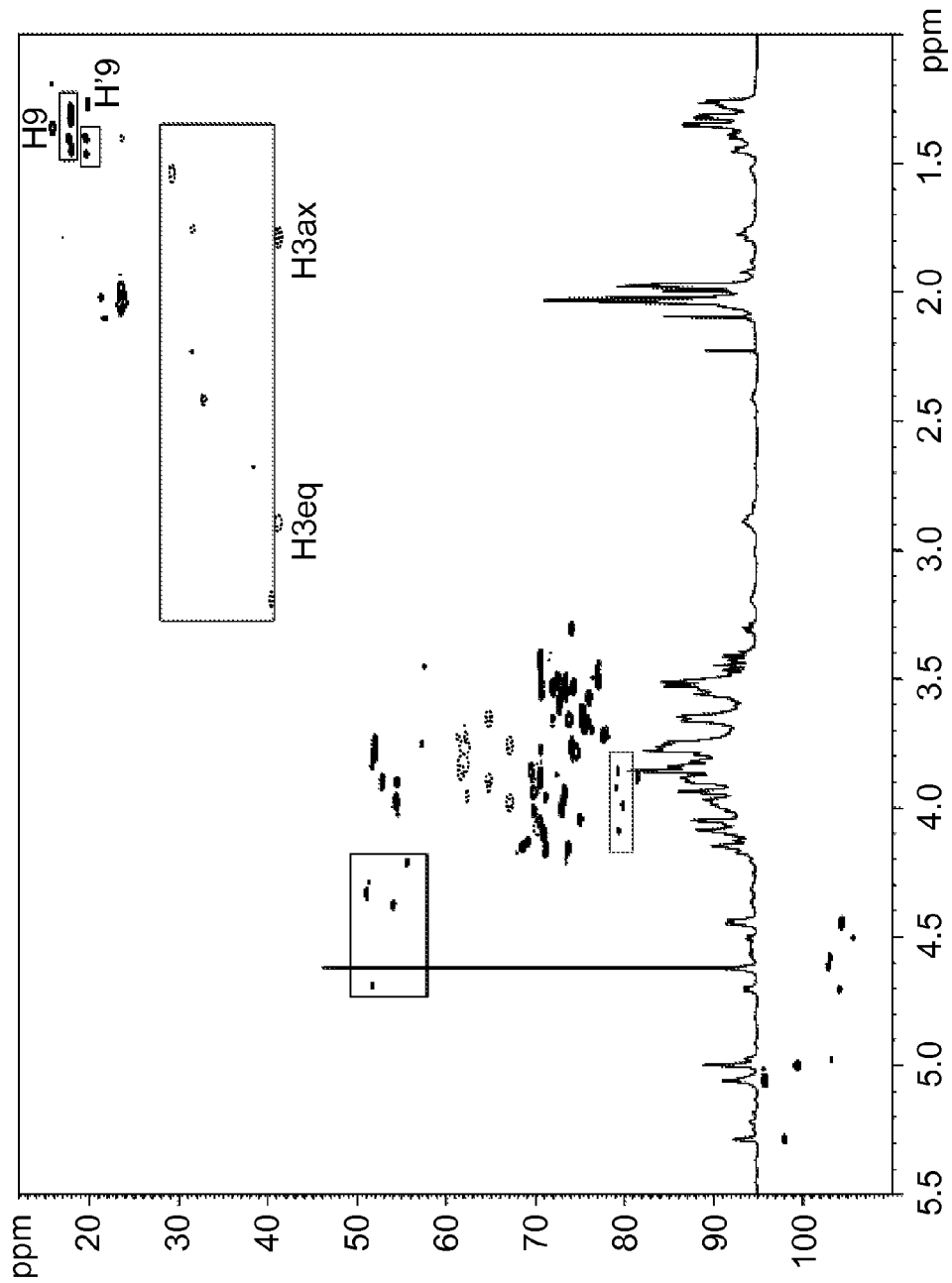
FIG. 7 shows a $^1$H-$^{13}$C HSQC spectrum of the Pf4 polysaccharide sample. Some major signals not related to the described polysaccharide structure are marked by boxes.

The saccharide structure may be determined by methods and tools known art, such as, for example, NMR, including $^1$D, $^1$H, and/or $^{13}$C, 2D TOCSY, DQF-COSY, NOESY, and/or HMQC. In one embodiment, the saccharide is a polysaccharide having an NMR spectrum as shown in FIG. 7.

In one embodiment, the saccharide is an isolated saccharide. In a preferred embodiment, the saccharide is isolated from an *Enterococcus* bacterium, preferably an *E. faecium* strain selected from any of the strains described herein. In a preferred embodiment, the saccharide is isolated from an *E. faecium* strain selected from any of the following strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In another preferred embodiment, the saccharide is isolated from an *E. faecium* E155 (Freiburg) strain.

In a one embodiment, the saccharide is a saccharide isolated from *E. faecium* TX0016 (DO; E1794). In a preferred embodiment, the saccharide is a polysaccharide that is isolated from *E. faecium* TX0016 (DO; E1794), wherein the polysaccharide includes at least one repeating unit of a structure represented by formula (I), and wherein n is an integer of at least one and at most 100, more preferably wherein n is an integer of at least 10 to at most 60, and most preferably, wherein n is an integer of at least 30 to at most 50, such as, for example wherein n is an integer of about 43. In one embodiment, the polysaccharide is isolated from *E. faecium* TX0016 (DO; E1794), wherein the polysaccharide includes at least one repeating unit of a structure represented by formula (I), and wherein the molecular weight of the polysaccharide is at least about 20 kDa, preferably at least about 40 kDa, more preferably at least about 60 kDa, most preferably about 62.5 kDa. Accordingly, in one embodiment, the isolated polysaccharide includes at least one repeating unit of a structure represented by formula (I), wherein n is an integer greater than or equal to 1, as described above. In another embodiment, the isolated polysaccharide has a molecular weight as described above.

In another preferred embodiment, the saccharide is a saccharide isolated from *E. faecium* E0155. In one embodiment, the saccharide is a polysaccharide isolated from *E. faecium* E0155, wherein the polysaccharide includes at least one repeating unit of a structure represented by formula (I), and wherein n is an integer of at least one and at most 100, more preferably wherein n is an integer of at least 20 to at most 80, and most preferably, wherein n is an integer of at least 50 to at most 70, such as, for example wherein n is an integer of about 60. In one embodiment, the polysaccharide is isolated from *E. faecium* E0155, wherein the polysaccharide includes at least one repeating unit of a structure represented by formula (I), and wherein the molecular weight of the polysaccharide is at least about 20 kDa, preferably at least about 40 kDa, more preferably at least about 90 kDa, most preferably about 92.5 kDa. Accordingly, in one embodiment, the isolated polysaccharide includes at least one repeating unit of a structure represented by formula (I), wherein n is an integer greater than or equal to 1, as described above. In another embodiment, the isolated polysaccharide has a molecular weight as described above.

In one embodiment, the saccharide is a polysaccharide isolated from *E. faecium* E155 (Freiburg), wherein the polysaccharide includes at least one repeating unit of a structure represented by formula (I), and wherein n is an integer of at least one and at most 100, more preferably wherein n is an integer of at least 20 to at most 80, and most preferably, wherein n is an integer of at least 50 to at most 70, such as, for example wherein n is an integer of about 60. In one embodiment, the polysaccharide is isolated from *E. faecium* E155 (Freiburg), wherein the polysaccharide includes at least one repeating unit of a structure represented by formula (I), and wherein the molecular weight of the polysaccharide is at least about 20 kDa, preferably at least about 40 kDa, more preferably at least about 90 kDa, most preferably about 92.5 kDa. Accordingly, in one embodiment, the isolated polysaccharide includes at least one repeating unit of a structure represented by formula (I), wherein n is an integer greater than or equal to 1, as described above. In another embodiment, the isolated polysaccharide has a molecular weight as described above.

In another embodiment, the invention relates to a saccharide including a structure represented by formula (I), wherein the saccharide is chemically synthesized. In a further embodiment, the saccharide is a branched polysaccharide.

In one embodiment, the invention relates to a chemically synthesized polysaccharide including at least one repeating unit of a structure represented by formula (I), wherein n is an integer greater than or equal to 1, as described above. In another embodiment, the chemically synthesized polysaccharide has a molecular weight as described above.

In one embodiment, the saccharide is immunogenic and is capable of inducing an immune response in a mammal. In one embodiment, the saccharide is capable of inducing opsonic activity. The opsonic activity may be against a Gram-positive coccus, preferably against a *Enterococcus* species, more preferably against at least one strain of *E. faecium*. For example, in one embodiment, the saccharide is capable of inducing opsonic activity against at least one of any of the following *E. faecium* strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In a preferred embodiment, the saccharide is capable of inducing opsonic activity at least against any of the following *E. faecium* strains: *E. faecium* E0980. In a preferred embodiment, the saccharide is capable of inducing opsonic activity at least against *E. faecium* E0155. In another embodiment, the saccharide is capable of inducing opsonic activity at least against *E. faecium* E155 (Freiburg). In another preferred embodiment, the saccharide is capable of inducing opsonic activity at least against *E. faecium* 1,230,933. In another preferred embodiment, the saccharide is capable of inducing opsonic activity at least against *E. faecium* 1,231,410. In yet another preferred embodiment, the saccharide is capable of inducing opsonic activity at least against *E. faecium* 1,231,502.

In another embodiment, the saccharide is capable of inducing opsonic and phagocytic activity (e.g., opsonophagocytic activity). The opsonophagocytic activity may be against a Gram-positive coccus, preferably against a *Enterococcus* species, more preferably against at least one strain of *E. faecium*. For example, in one embodiment, the saccharide is capable of inducing opsonophagocytic activity against at least one of any of the following *E. faecium* strains: E1162; E1636; E1679; 00317; E0155; TX0016; 1,230,933; 1,231,408; 1,141,733; 1,231,410; 1,231,501; 1,231,502; E0980; E1039; E1071; Com12; Com15; and TX1330. In one embodiment, the saccharide is capable of inducing opsonophagocytic activity at least against *E. faecium* E155 (Freiburg) strain.

In a preferred embodiment, the saccharide is capable of inducing opsonophagocytic activity at least against any of the following *E. faecium* strains: *E. faecium* E0980. In a preferred embodiment, the saccharide is capable of inducing opsonophagocytic activity at least against *E. faecium* E0155. In another preferred embodiment, the saccharide is capable of inducing opsonophagocytic activity at least against *E. faecium* 1,230,933. In another preferred embodiment, the saccharide is capable of inducing opsonophagocytic activity at least against *E. faecium* 1,231,410. In yet another preferred embodiment, the saccharide is capable of inducing opsonophagocytic activity at least against *E. faecium* 1,231,502.

In yet another embodiment, the saccharide is capable of inducing a bactericidal immune response. In one embodiment, the bactericidal activity is against a Gram-positive coccus, preferably against a *Enterococcus* species, more preferably against at least one strain of *E. faecium*. For example, in one embodiment, the saccharide is capable of inducing bactericidal activity against at least one of any of the following *E. faecium* strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In one embodiment, the saccharide is capable of inducing bactericidal activity against *E. faecium* E155 (Freiburg) strain.

In a preferred embodiment, the saccharide is capable of inducing bactericidal activity at least against any of the following *E. faecium* strains: *E. faecium* E0980. In a preferred embodiment, the saccharide is capable of inducing bactericidal activity at least against *E. faecium* E0155. In another preferred embodiment, the saccharide is capable of inducing bactericidal activity at least against *E. faecium* E155 (Freiburg). In another preferred embodiment, the saccharide is capable of inducing bactericidal activity at least against *E. faecium* 1,230,933. In another preferred embodiment, the saccharide is capable of inducing bactericidal activity at least against *E. faecium* 1,231,410. In yet another preferred embodiment, the saccharide is capable of inducing bactericidal activity at least against *E. faecium* 1,231,502.

Saccharide Including an Altruronic Acid Moiety

In one aspect, the invention relates to a saccharide including an altruronic acid moiety. Altruronic acid ((2S,3S,4R, 5S)-2,3,4,5-tetrahydroxy-6-oxohexanoic acid or AltA) has a molecular formula of $C_6H_{10}O_7$. Altruronic acid has a molecular weight of about 194 Da.

In one embodiment, the saccharide includes an altruronic acid moiety and a fucose (Fuc) moiety.

In one embodiment, the saccharide includes an altruronic acid moiety and a glucose (Glc) moiety.

In one embodiment, the saccharide includes an altruronic acid moiety, a fucose moiety, and a glucose moiety. In a preferred arrangement of the saccharide, the altruronic acid moiety is linked to a fucose moiety. In another preferred arrangement, a fucose moiety is linked to a glucose moiety.

In one embodiment, the saccharide is a polysaccharide including an altruronic acid moiety. In one embodiment, the polysaccharide includes an altruronic acid moiety, a fucose moiety, and a glucose moiety. In a preferred arrangement of the polysaccharide, the altruronic acid moiety is linked to a fucose moiety. In another preferred arrangement, a fucose moiety is linked to a glucose moiety. In another embodiment, the polysaccharide includes an altruronic acid moiety, a fucose moiety, and a glucose moiety in a molar ratio of 1:4:2.

In one embodiment, the saccharide has a molecular weight of at least about 1 kDa, 1.046 kDa, 2 kDa, 10 kDa, or 20 kDa to at most about 5000 kDa, 2000 kDa, 1000 kDa, 900 kDa, 800 kDa, 700 kDa, 600 kDa, 500 kDa, 400 kDa, or 300 kDa. Any minimum value and any maximum value may be combined to define a range. For example, in one embodiment, the saccharide has a molecular weight of at least about 1 kDa to at most about 5000 kDa, preferably at least about 50 kDa to at most about 500 kDa. In one embodiment, the saccharide has a molecular weight of about 300.6 kDa.

The molecular weight or average molecular weight of a saccharide described herein refers to the weight of the saccharide as measured by a method known in the art, such as, for example, multi-angle laser light scattering (MALLS). It should be noted that the molecular weight of a given saccharide may vary depending factors such as, for example, pathway and environments of synthesis of the saccharide, the extraction conditions used to isolate the saccharide, the species from which the saccharide is isolated, and/or on location and time of harvest of the saccharide. Moreover, saccharides isolated and purified from natural sources may be heterogenous in size. Accordingly, the value for molecular weight may represent an average or median value for the molecular weight of the molecules in a particular population.

In one embodiment, the saccharide includes a structure represented by formula (II):

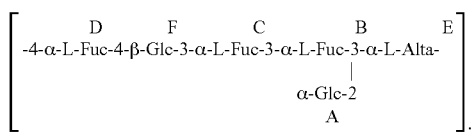

A saccharide that includes a structure represented by formula (II) has a molecular weight of at least about 1000 Da, preferably at least about 1400 Da, most preferably at least about 1046 Da.

In one embodiment, the saccharide including a structure represented by formula (II) is a polysaccharide. In another embodiment, the polysaccharide includes at least one repeating unit of a structure represented by formula (II):

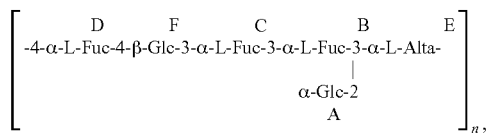

wherein n is integer greater than or equal to 1.

In one embodiment, n in formula (II) is an integer of at least 1, 2, 3, 4, 5, 10, 20, or 30 and at most 1000, 500, 400, 300, 200, 100, 90, 80, 70, 60, 50, or 40. Any minimum value and any maximum value may be combined to define a range. Exemplary ranges include, for example, at least 1 to at most 1000; at least 10 to at most 500; and at least 100 to at most 300. In one embodiment, the polysaccharide includes at least one repeating unit of a structure represented by formula (II), wherein n is an integer of at least 200 to at most 400, more preferably, wherein n is an integer of about 290. For example, in one embodiment, n is 285, 286, 287, 288, 289, 290, 291, 292, 293, 294, or 295.

Figure 2:
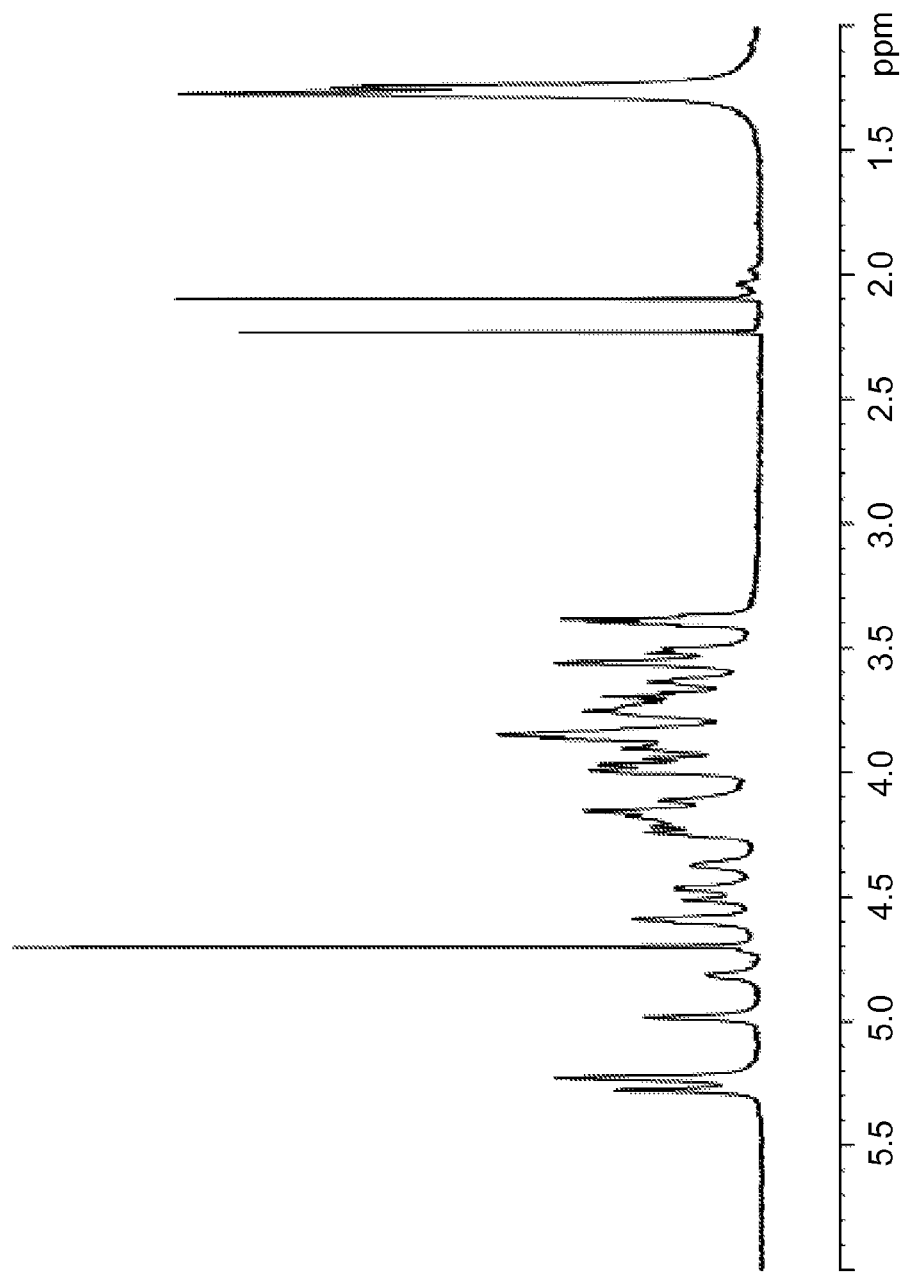
FIG. 2 shows a $^1$H NMR spectrum of the polysaccharide Pf2. Sharp peaks around 2 ppm are acetone (internal standard) and acetic acid (from column buffer).

The saccharide structure may be determined by methods and tools known art, such as, for example, NMR, including $^1$D, $^1$H, and/or $^{13}$C, 2D TOCSY, DQF-COSY, NOESY, and/or HMQC. In one embodiment, the saccharide is a polysaccharide having an NMR spectrum as shown in FIG. 2.

In one embodiment, the saccharide is an isolated saccharide. In one embodiment, the saccharide is isolated from an *Enterococcus* bacterium, preferably an *E. faecium* strain selected from any of the strains described herein. In a preferred embodiment, the saccharide is isolated from an *E. faecium* strain selected from any of the following strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In a further preferred embodiment, the saccharide is a polysaccharide isolated from *E. faecium* TX0016 (DO; E1794). In another preferred embodiment, the saccharide is a polysaccharide isolated from *E. faecium* E0155. In another preferred embodiment, the saccharide is isolated from an *E. faecium* E155 (Freiburg) strain.

In one embodiment, the isolated polysaccharide includes at least one repeating unit of a structure represented by formula (II), wherein n is an integer greater than or equal to 1, as described above. In one embodiment, the isolated polysaccharide has a molecular weight as described above.

In another embodiment, the invention relates to a saccharide including a structure represented by formula (II), wherein the saccharide is chemically synthesized. In a further embodiment, the saccharide is a branched saccharide.

In one embodiment, the invention relates to a chemically synthesized polysaccharide including at least one repeating unit of a structure represented by formula (II), wherein n is an integer greater than or equal to 1, as described above. In one embodiment, the chemically synthesized polysaccharide has a molecular weight as described above.

In one embodiment, the saccharide is immunogenic and is capable of inducing an immune response in a mammal. In one embodiment, the saccharide is capable of inducing opsonic activity. The opsonic activity may be against a Gram-positive coccus, preferably against an *Enterococcus* species, more preferably against at least one strain of *E. faecium*. For example, in one embodiment, the saccharide is capable of inducing opsonic activity against at least one of any of the following *E. faecium* strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In another embodiment, the saccharide is capable of inducing opsonic activity at least against *E. faecium* E155 (Freiburg).

In a preferred embodiment, the saccharide is capable of inducing opsonic activity at least against any of the following *E. faecium* strains: *E. faecium* E0980. In a preferred embodiment, the saccharide is capable of inducing opsonic activity at least against *E. faecium* TX0016 (DO). In another preferred embodiment, the saccharide is capable of inducing opsonic activity at least against *E. faecium* 1,230,933. In another preferred embodiment, the saccharide is capable of inducing opsonic activity at least against *E. faecium* 1,231,410. In yet another preferred embodiment, the saccharide is capable of inducing opsonic activity at least against *E. faecium* 1,231,502.

In another embodiment, the saccharide is capable of inducing opsonic and phagocytic activity (e.g., opsonophagocytic activity). The opsonophagocytic activity may be against a Gram-positive coccus, preferably against a *Enterococcus* species, more preferably against at least one strain of *E. faecium*. For example, in one embodiment, the saccharide is capable of inducing opsonophagocytic activity against at least one of any of the following *E. faecium* strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In another preferred embodiment, the saccharide is capable of inducing opsonophagocytic activity at least against *E. faecium* E155 (Freiburg).

In a preferred embodiment, the saccharide is capable of inducing opsonophagocytic activity at least against any of the following *E. faecium* strains: *E. faecium* E0980. In a preferred embodiment, the saccharide is capable of inducing opsonophagocytic activity at least against *E. faecium* TX0016 (DO). In another preferred embodiment, the saccharide is capable of inducing opsonophagocytic activity at least against *E. faecium* 1,230,933. In another preferred embodiment, the saccharide is capable of inducing opsonophagocytic activity at least against *E. faecium* 1,231,410. In yet another preferred embodiment, the saccharide is capable of inducing opsonophagocytic activity at least against *E. faecium* 1,231,502.

In yet another embodiment, the saccharide is capable of inducing a bactericidal immune response. In one embodiment, the bactericidal activity is against a Gram-positive coccus, preferably against a *Enterococcus* species, more preferably against at least one strain of *E. faecium*. For example, in one embodiment, the saccharide is capable of inducing bactericidal activity against at least one of any of the following *E. faecium* strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In one embodiment, the saccharide is capable of inducing bactericidal activity against *E. faecium* E155 (Freiburg) strain.

In a preferred embodiment, the saccharide is capable of inducing bactericidal activity at least against any of the following *E. faecium* strains: *E. faecium* E0980. In a preferred embodiment, the saccharide is capable of inducing bactericidal activity at least against *E. faecium* TX0016 (DO). In another preferred embodiment, the saccharide is capable of inducing bactericidal activity at least against *E. faecium* 1,230,933. In another preferred embodiment, the saccharide is capable of inducing bactericidal activity at least against *E. faecium* 1,231,410. In yet another preferred embodiment, the saccharide is capable of inducing bactericidal activity at least against *E. faecium* 1,231,502.

Saccharide Including a Glycerol Phosphate Moiety

In one aspect, the invention relates to a saccharide including a glycerol phosphate moiety. Glycerol phosphate (2,3-dihydroxypropyl dihydrogen phosphate or Gro-1P) has a molecular formula of $C_3H_9O_6P$, and a molecular weight of about 172 Da. In one embodiment, the saccharide includes a glycerol phosphate moiety and a glucose (Glc) moiety.

In one embodiment, the saccharide is a polysaccharide including a glycerol phosphate moiety. In one embodiment, the polysaccharide includes a glycerol phosphate moiety and a glucose moiety in a molar ratio of 1:1. In another embodiment, the polysaccharide includes a glycerol phosphate moiety and a glucose moiety in a molar ratio of 1:2.

In one embodiment, the polysaccharide is a teichoic acid. In another embodiment, the polysaccharide is a lipoteichoic acid. A lipoteichoic acid includes a teichoic acid and a lipid tail that may be linked to the plasma membrane of a bacterium.

In one embodiment, the saccharide has a molecular weight of at least about 170 Da, 172 Da, 300 Da, 344 Da, 500 Da, 668 Da, 1 kDa, 2 kDa, 10 kDa, or 20 kDa to at most about 5000 kDa, 2000 kDa, 1000 kDa, 900 kDa, 800 kDa, 700 kDa, 600 kDa, 500 kDa, 100 kDa, 90 kDa, 80 kDa, 70 kDa, 60 kDa. Any minimum value and any maximum value may be combined to define a range. For example, in one embodiment, the saccharide has a molecular weight of at least about 172 Da to at most about 5000 kDa, preferably at least about 1 kDa to at most about 100 kDa. More preferably, the saccharide has a molecular weight of at least about 10 kDa to at most about 20 kDa. In one preferred embodiment, the saccharide has a molecular weight of at least about 12 kDa to at most about 15 kDa.

The molecular weight or average molecular weight of a saccharide described herein refers to the weight of the saccharide as measured by a method known in the art, such as, for example, multi-angle laser light scattering (MALLS). It should be noted that the molecular weight of a given saccharide may vary depending factors such as, for example, pathway and environments of synthesis of the saccharide, the extraction conditions used to isolate the saccharide, the species from which the saccharide is isolated, and/or on location and time of harvest of the saccharide. Moreover, saccharides isolated and purified from natural sources may be heterogenous in size. Accordingly, the value for molecular weight may represent an average or median value for the molecular weight of the molecules in a particular population.

In one embodiment, the saccharide includes at least one glycerol phosphate moiety. In another embodiment, the saccharide includes a structure represented by formula (III):

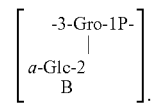

A saccharide that includes a structure represented by formula (III) has a molecular weight of at least about 100 Da, preferably at least about 172 Da, more preferably at least about 334 Da.

In one embodiment, the saccharide including a structure represented by formula (III) is a polysaccharide. In yet another embodiment, the saccharide includes at least one repeating unit of formula (III):

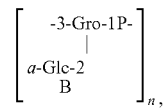

wherein n is any integer greater than or equal to 1.

In one embodiment, n in formula (III) is an integer of at least 1, 2, 3, 4, 5, 10, 20, or 30 and at most 1000, 500, 400, 300, 200, 100, 90, 80, 70, 60, 50, or 40. Any minimum value and any maximum value may be combined to define a range. Exemplary ranges include, for example, at least 1 to at most 1000; at least 10 to at most 500; and at least 50 to at most 200. In one embodiment, the polysaccharide includes at least one repeating unit of a structure represented by formula (III), wherein n is an integer of about 90. For example, in one embodiment, n is 85, 86, 87, 88, 89, 90, 91, 92, 93, 94, 95, 96, 97, 98, or 99, most preferably 90.

In one embodiment, the saccharide includes formula (IV):

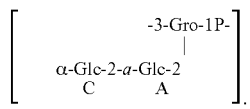

In one embodiment, the saccharide including a structure represented by formula (IV) is a polysaccharide. In another embodiment, the polysaccharide includes at least one repeating unit of formula (IV):

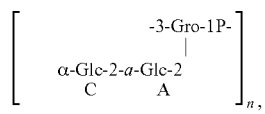

wherein n is any integer greater than or equal to 1.

In one embodiment, n in formula (IV) is an integer of at least 1, 2, 3, 4, 5, 10, 20, or 30 and at most 1000, 500, 400, 300, 200, 100, 90, 80, 70, 60, 50, or 40. Any minimum value and any maximum value may be combined to define a range. Exemplary ranges include, for example, at least 1 to at most 1000; at least 10 to at most 500; and at least 50 to at most 200. In one embodiment, the polysaccharide includes at least one repeating unit of a structure represented by formula (IV), wherein n is an integer of about 90. For example, in one embodiment, n is 85, 86, 87, 88, 89, 90, 91, 92, 93, 94, 95, 96, 97, 98, or 99, most preferably 90.

In one embodiment, the polysaccharide includes glycerol phosphate, a unit of formula (III), and a unit of formula (IV). The unit of formula (III) and the unit of formula (IV) may be present in the polysaccharide in a molar ratio of 1:1.

Figure 6:
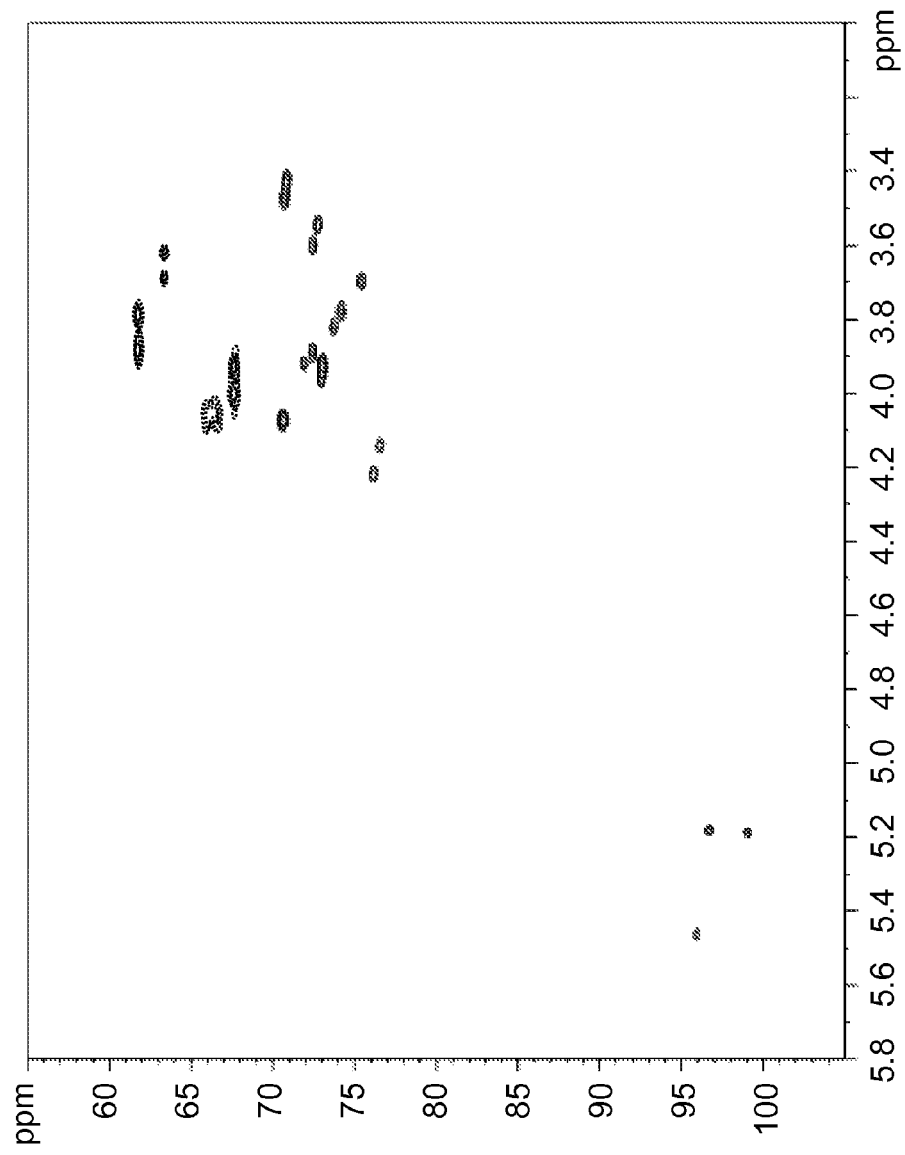
FIG. 6 shows a $^1$H-$^{13}$C HSQC spectrum of the Pf3 polysaccharide.

The saccharide structure may be determined by methods and tools known art, such as, for example, NMR, including $^1$D, $^1$H, and/or $^{13}$C, 2D TOCSY, DQF-COSY, NOESY, and/or HMQC. In one embodiment, the saccharide is a polysaccharide having an NMR spectrum as shown in FIG. 6.

In one embodiment, the saccharide is an isolated saccharide. In a preferred embodiment, the saccharide is isolated from an *Enterococcus* bacterium, preferably an *E. faecium* strain selected from any of the strains described herein. In another preferred embodiment, the saccharide is isolated from an *E. faecium* strain selected from any of the following strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In a further preferred embodiment, the saccharide is a polysaccharide isolated from *E. faecium* TX0016 (DO; E1794). In another preferred embodiment, the saccharide is a polysaccharide isolated from *E. faecium* E0155. In another preferred embodiment, the saccharide is isolated from an *E. faecium* E155 (Freiburg) strain.

In one embodiment, the isolated polysaccharide includes at least one repeating unit of a levan moiety, wherein n is an integer greater than or equal to 1, as described above. In one embodiment, the isolated polysaccharide has a molecular weight as described above.

In another embodiment, the invention relates to a saccharide including a structure represented by formula (III), wherein the saccharide is chemically synthesized. In yet another embodiment, the invention relates to a saccharide including a structure represented by formula (IV), wherein the saccharide is chemically synthesized. In one embodiment, the saccharide is a branched saccharide.

In one embodiment, the invention relates to a chemically synthesized polysaccharide including at least one repeating unit of a structure represented by formula (III), wherein n is an integer greater than or equal to 1, as described above. In one embodiment, the chemically synthesized polysaccharide has a molecular weight as described above.

In one embodiment, the chemically synthesized polysaccharide includes at least one repeating unit of a structure represented by formula (IV), wherein n is an integer greater than or equal to 1, as described above. In one embodiment, the chemically synthesized polysaccharide has a molecular weight as described above.

In one embodiment, the saccharide is immunogenic and is capable of inducing an immune response in a mammal. In one embodiment, the saccharide is capable of inducing opsonic activity. The opsonic activity may be against a Gram-positive coccus, preferably against a *Enterococcus* species, more preferably against at least one strain of *E. faecium*. For example, in one embodiment, the saccharide is capable of inducing opsonic activity against at least one of any of the following *E. faecium* strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In a preferred embodiment, the saccharide is capable of inducing opsonic activity at least against *E. faecium* E0155. In another embodiment, the saccharide is capable of inducing opsonic activity at least against *E. faecium* E155 (Freiburg).

In another embodiment, the saccharide is capable of inducing opsonic and phagocytic activity (e.g., opsonophagocytic activity). The opsonophagocytic activity may be against a Gram-positive coccus, preferably against a *Enterococcus* species, more preferably against at least one strain of *E. faecium*. For example, in one embodiment, the saccharide is capable of inducing opsonophagocytic activity against at least one of any of the following *E. faecium* strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In a preferred embodiment, the saccharide is capable of inducing opsonophagocytic activity at least against *E. faecium* E0155. In another embodiment, the saccharide is capable of inducing opsonophagocytic activity at least against *E. faecium* E155 (Freiburg).

In yet another embodiment, the saccharide is capable of inducing a bactericidal immune response. In one embodiment, the bactericidal activity is against a Gram-positive coccus, preferably against a *Enterococcus* species, more preferably against at least one strain of *E. faecium*. For example, in one embodiment, the saccharide is capable of inducing bactericidal activity against at least one of any of the following *E. faecium* strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In a preferred embodiment, the saccharide is capable of inducing bactericidal activity at least against *E. faecium* E0155. In one embodiment, the saccharide is capable of inducing bactericidal activity against *E. faecium* E155 (Freiburg) strain.

Saccharide Including a Levan Moiety

In one aspect, the invention relates to a saccharide including a levan moiety. Levan ((2→6)-beta-D-fructofuranan or 6-β-D-Fruf-2) has a molecular formula of $C_{18}H_{32}O_{16}$, and a molecular weight of about 504 Da.

In one embodiment, the saccharide has a molecular weight of at least about 500 Da, 504 Da, 1 kDa, 2 kDa, 10 kDa, or 20 kDa to at most about 50,000 kDa, 30,000 kDa, 10,000 kDa, 5000 kDa, 2000 kDa, 1000 kDa, 900 kDa, 800 kDa, 700 kDa, 600 kDa, 500 kDa, 100 kDa, 90 kDa, 80 kDa, 70 kDa, 60 kDa. Any minimum value and any maximum value may be combined to define a range. For example, in one embodiment, the saccharide has a molecular weight of at least about 500 Da to at most about 50,000 kDa, preferably at least about 1 kDa to at most about 30,000 kDa. More preferably, the saccharide has a molecular weight of at least about 5000 kDa to at most about 25,000 kDa. In one preferred embodiment, the saccharide has a molecular weight of at least about 10,000 kDa to at most about 25,000 kDa.

The molecular weight or average molecular weight of a saccharide described herein refers to the weight of the saccharide as measured by a method known in the art, such as, for example, multi-angle laser light scattering (MALLS). It should be noted that the molecular weight of a given saccharide may vary depending factors such as, for example, pathway and environments of synthesis of the saccharide, the extraction conditions used to isolate the saccharide, the species from which the saccharide is isolated, and/or on location and time of harvest of the saccharide.

In one embodiment, the saccharide is a polysaccharide that includes at least one repeating unit of a levan moiety, wherein the n number of units is any integer greater than or equal to 1. In one embodiment, n is an integer of at least 1, 2, 3, 4, 5, 10, 20, or 30 and at most 100,000, 50,000, 40,000, 1000, 500, 400, 300, 200, 100, 90, 80, 70, 60, 50, or 40. Any minimum value and any maximum value may be combined to define a range. Exemplary ranges include, for example, at least 1 to at most 100,000; at least 10 to at most 50,000; and at least 50 to at most 50,000. In one embodiment, the polysaccharide includes at least one repeating unit of a levan moiety, wherein n is an integer of at most about 40,000.

The saccharide structure may be determined by methods and tools known art, such as, for example, NMR, including $^1$D, $^1$H, and/or $^{13}$C, 2D TOCSY, DQF-COSY, NOESY, and/or HMQC. In one embodiment, the saccharide is a polysaccharide having an NMR spectrum as shown in FIG. 1.

In one embodiment, the saccharide is an isolated saccharide. In a preferred embodiment, the saccharide is isolated from an *Enterococcus* bacterium, preferably an *E. faecium* strain selected from any of the strains described herein. In another preferred embodiment, the saccharide is isolated from an *E. faecium* strain selected from any of the following strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In a further preferred embodiment, the saccharide is a polysaccharide isolated from *E. faecium* TX0016 (DO; E1794). In another preferred embodiment, the saccharide is a polysaccharide isolated from *E. faecium* E0155. In another preferred embodiment, the saccharide is isolated from an *E. faecium* E155 (Freiburg) strain.

In one embodiment, the isolated polysaccharide includes at least one repeating unit of a levan moiety, wherein n is an integer greater than or equal to 1, as described above. In one embodiment, the isolated polysaccharide has a molecular weight as described above.

In another embodiment, the invention relates to a saccharide including a levan moiety, wherein the saccharide is chemically synthesized. In one embodiment, the saccharide is a branched saccharide.

In one embodiment, the invention relates to a chemically synthesized polysaccharide including at least one repeating unit of a levan moiety, wherein n is an integer greater than or equal to 1, as described above. In one embodiment, the chemically synthesized polysaccharide includes at least one repeating unit of a levan moiety, and has a molecular weight as described above.

In one embodiment, the saccharide is immunogenic and is capable of inducing an immune response in a mammal. In one embodiment, the saccharide is capable of inducing opsonic activity. The opsonic activity may be against a Gram-positive coccus, preferably against a *Enterococcus* species, more preferably against at least one strain of *E. faecium*. For example, in one embodiment, the saccharide is capable of inducing opsonic activity against at least one of any of the following *E. faecium* strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In another embodiment, the saccharide is capable of inducing opsonic activity at least against *E. faecium* E155 (Freiburg).

In another embodiment, the saccharide is capable of inducing opsonic and phagocytic activity (e.g., opsonophagocytic activity). The opsonophagocytic activity may be against a Gram-positive coccus, preferably against a *Enterococcus* species, more preferably against at least one strain of *E. faecium*. For example, in one embodiment, the saccharide is capable of inducing opsonophagocytic activity against at least one of any of the following *E. faecium* strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In another embodiment, the saccharide is capable of inducing opsonophagocytic activity at least against *E. faecium* E155 (Freiburg).

In yet another embodiment, the saccharide is capable of inducing a bactericidal immune response. In one embodiment, the bactericidal activity is against a Gram-positive coccus, preferably against a *Enterococcus* species, more preferably against at least one strain of *E. faecium*. For example, in one embodiment, the saccharide is capable of inducing bactericidal activity against at least one of any of the following *E. faecium* strains: E1162; E1636; E1679; U0317; E0155; TX0016; 1,230,933; 1,231,408; 1,141,733; 1,231,410; 1,231,501; 1,231,502; E0980; E1039; E1071; Com12; Com15; and TX1330. In one embodiment, the saccharide is capable of inducing bactericidal activity against *E. faecium* E155 (Freiburg) strain.

Compositions Including a Saccharide

In one aspect, the invention relates to a composition including a combination of at least two of any saccharide described herein. For example, in one embodiment, the composition includes at least two of any of: (a) a polysaccharide including a legionaminic acid moiety; (b) a polysaccharide including an altruronic acid moiety; (c) a polysaccharide including a glycerol phosphate moiety; and (d) a polysaccharide including a levan moiety. In another embodiment, the composition includes at least three of any isolated polysaccharide described herein. In yet another embodiment, the composition includes at least four of any isolated polysaccharide described herein.

In another aspect, the invention relates to a composition including at least one of any saccharide described herein and a pharmaceutically acceptable excipient, carrier, buffer, stabilizer, adjuvant, or mixture thereof. In a preferred embodiment, the composition includes an isolated polysaccharide described herein and a carrier molecule. Suitable carrier molecules may include proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG.

Polysaccharide-Protein Conjugates

As used herein, a "polysaccharide-protein conjugate" refers to a polysaccharide molecule conjugated to a protein carrier molecule through one or more covalent bonds. It may be desirable to conjugate the polysaccharide to a protein from another species known to be immunogenic in the target host. Accordingly, in one embodiment, the carrier molecule is a carrier protein. As defined herein, such a foreign protein is referred to as a "carrier protein." Carrier proteins serve to enhance the antigenicity and immunogenicity of the polysaccharide. As used herein, the term "carrier effect" refers to the process where the antigenicity and immunogenicity of a weakly immunogenic or non-immunogenic molecule is enhanced, by being attached to a more immunogenic molecule as carrier (e.g., a heterologous protein). In this case, the polysaccharide in the combined polysaccharide-protein conjugate becomes more immunogenic than if it were presented alone. Carrier proteins contain T cell epitopes for stimulating T-cell help for producing antibody responses.

Cross-reacting materials or CRMs are especially useful for some embodiments of the present invention. One may produce genetically altered proteins, which are antigenically similar to the certain bacterial toxins, yet non-toxic. These are called "cross reacting materials", or CRMs. $CRM_{197}$ is noteworthy since it has a single amino acid change from the native diphtheria toxin and is immunologically indistinguishable from it. See Pappenheimer et al., Immunochem., 9:891-906, (1972), and U.S. Pat. No. 5,614,382 the disclosures of which are hereby incorporated by reference in their entirety. CRM3201 is a genetically manipulated variant of pertussis toxin. See Black et al., Science, 240:656-659, (1988), the disclosures of which is hereby incorporated by reference in their entirety.

In addition to a diphtheria toxoid, $CRM_{197}$, and a pertussis toxoid, further examples of carrier proteins include a tetanus toxoid, a cholera toxoid, an E. coli heat labile toxoid (LT), pneumolysin from S. pneumonia (wild-type or mutant with reduced toxicity), pneumococcal surface protein A (PspA), pneumococcal adhesin protein A (PsaA), a C5a peptidase from Streptococcus, hemolysin from Staphylococcus aureus, Nontypeable Haemophilus influenzae (NTHi) proteins, Haemophilus influenzae protein D, Clostridium perfringens exotoxins/toxoid, hepatitis B surface antigen, hepatitis B core antigen, rotavirus VP 7 protein, and respiratory syncytial virus F and G protein, ovalbumin, keyhole limpet haemocyanin (KLH), bovine serum albumin (BSA), purified protein derivative of tuberculin (PPD), and a Pseudomonas exotoxin, or its derivatives including a recombinantly-produced non-toxic mutant Pseudomonas aeruginosa Exotoxin A. In a preferred embodiment, the carrier protein is a diphtheria toxoid. More preferably, the carrier protein is $CRM_{197}$.

In a preferred embodiment, the composition includes a polysaccharide linked to the carrier molecule. The polysaccharide may be linked by any suitable means known in the art. Preferably, the polysaccharide is conjugated to the carrier molecule. Methods of conjugating a carrier protein to a polysaccharide are known in the art.

A "conjugate immunogenic composition," as used herein, refers to a immunogenic composition wherein the immunogenic material includes an antigenic saccharide that is covalently linked to a carrier protein to produce a saccharide-protein conjugate. In one embodiment, a saccharide-protein conjugate of the invention may be formulated as a univalent and/or multivalent immunogenic composition.

For the synthesis of a monovalent conjugate immunogen, saccharides derived from a single serotype of bacterium may be conjugated to protein. For the synthesis of a multivalent conjugate immunogenic composition, saccharide-protein conjugates may be produced by conjugating a mixture of saccharides purified from bacteria of two different species to a carrier protein. Alternatively, a multivalent conjugate immunogenic composition may be produced by combining saccharides purified from bacteria of two or more different serotypes of the same bacteria and conjugating them as a mixture to a carrier protein. Alternatively, saccharide-protein conjugates produced by reacting a single type of saccharide with carrier protein in separate reactions using different saccharides, may be mixed. Thus, a multivalent immunogenic composition may include a carrier protein bearing a homogeneous or a heterogeneous population of linked saccharides.

Exemplary Saccharide-Protein Compositions

In one aspect, the invention relates to a composition including a polysaccharide having a legionaminic acid moiety, and a carrier molecule. In one embodiment, the polysaccharide includes a structure represented by formula (I). In one embodiment, the polysaccharide is conjugated to the carrier molecule. In one embodiment, the composition is immunogenic.

In another aspect, the invention relates to a polysaccharide-protein conjugate comprising an immunogenic amount of a polysaccharide covalently linked to a carrier protein, wherein the polysaccharide includes a structure represented by formula (I). In one embodiment, the polysaccharide is isolated and/or purified from an Enterococcus bacterium, preferably E. faecium. In another embodiment, the polysaccharide is chemically synthesized. In yet another embodiment, the polysaccharide is prepared by expression in a surrogate host after cloning and expressing a biosynthetic pathway to produce the saccharide.

In one aspect, the invention relates to a composition including a polysaccharide having an altruronic acid moiety, and a carrier molecule. In one embodiment, the polysaccharide includes a structure represented by formula (II). In one embodiment, the polysaccharide is conjugated to the carrier molecule. In one embodiment, the composition is immunogenic.

In another aspect, the invention relates to a polysaccharide-protein conjugate comprising an immunogenic amount of a polysaccharide covalently linked to a carrier protein, wherein the polysaccharide includes a structure represented by formula (II). In one embodiment, the polysaccharide is isolated and/or purified from an Enterococcus bacterium, preferably E. faecium. In another embodiment, the polysaccharide is chemically synthesized. In yet another embodiment, the polysaccharide is prepared by expression in a surrogate host after cloning and expressing a biosynthetic pathway to produce the saccharide.

In one aspect, the invention relates to a composition including a polysaccharide having a glycerol phosphate moiety, and a carrier molecule. In one embodiment, the polysaccharide includes a structure represented by formula (III) and/or a structure represented by formula (IV). In one embodiment, the polysaccharide is conjugated to the carrier molecule. In one embodiment, the composition is immunogenic. In one embodiment, the polysaccharide is conjugated to the carrier molecule.

In another aspect, the invention relates to a polysaccharide-protein conjugate comprising an immunogenic amount of a polysaccharide covalently linked to a carrier protein, wherein the polysaccharide includes a structure represented by formula (III) and/or a structure represented by formula (IV). In one embodiment, the polysaccharide is isolated and/or purified from an *Enterococcus* bacterium, preferably *E. faecium*. In another embodiment, the polysaccharide is chemically synthesized. In yet another embodiment, the polysaccharide is prepared by expression in a surrogate host after cloning and expressing a biosynthetic pathway to produce the saccharide.

In one aspect, the invention relates to a composition including a polysaccharide having a levan moiety, and a carrier molecule. In one embodiment, the polysaccharide is conjugated to the carrier molecule. In one embodiment, the composition is immunogenic. In one embodiment, the polysaccharide is conjugated to the carrier molecule. In one embodiment, the polysaccharide is conjugated to the carrier molecule.

In another aspect, the invention relates to a polysaccharide-protein conjugate comprising an immunogenic amount of a polysaccharide covalently linked to a carrier protein, wherein the polysaccharide includes a levan moiety. In one embodiment, the polysaccharide is isolated and/or purified from an *Enterococcus* bacterium, preferably *E. faecium*. In another embodiment, the polysaccharide is chemically synthesized. In yet another embodiment, the polysaccharide is prepared by expression in a surrogate host after cloning and expressing a biosynthetic pathway to produce the saccharide.

Conjugation

Conjugation may be direct, where the atoms from the polysaccharide are covalently bonded to atoms from the protein surface. Conjugation may be through a linker molecule, which reacts with both the polysaccharide and the protein and connects the two and tethers the carbohydrate to the protein.

In one embodiment, the polysaccharide and the protein are conjugated together to form an immunogenic polysaccharide-protein conjugate or immunoconjugate. In one embodiment, there are between about 1 and about 50 molecules of conjugated polysaccharide per molecule of protein. In another embodiment, there are between about 1 and about 20 molecules of conjugated polysaccharide per molecule of protein. In a preferred embodiment, there are between about 2 and about 20 molecules of conjugated polysaccharide per molecule of protein.

Direct Polysaccharide to Protein Conjugation

Conjugates of the polysaccharide and protein carriers may be formed by reacting reducing end groups of the polysaccharide polymer fragment to primary amino groups of a carrier protein to yield antigenic determinants of the polymer covalently linked to the carrier protein. The reducing groups may be formed by selective hydrolysis or specific oxidative cleavage of the carbohydrate, or combinations of both.

Methods of conjugation are known in the art, such as, for example, conjugating a polysaccharide to a protein. In general, the polysaccharide should be activated or otherwise rendered amenable to conjugation, i.e., at least one moiety must be rendered capable of covalently bonding to a protein or other molecule. See, for example, U.S. Pat. No. 4,356,170, which describes the use of periodic acid to generate aldehyde groups on the polysaccharide and then performs reductive amination using cyanoborohydride. U.S. Pat. No. 4,663,160, describes use of periodic acid to generate aldehyde groups but then linked the polysaccharide to a protein derivatized with a 4-12 carbon moiety with a Schiff's base reaction in the presence of a reducing agent such as cyanoborohydride. U.S. Pat. No. 4,619,828, which describes cyanogen bromide to activate the polysaccharide and then conjugated it through a spacer bridge of 4-8 carbon atoms to the protein. Still other methods of conjugation are known in the art.

Where the polysaccharide is hydrolyzed to form polysaccharide fragments having only one functional aldehyde group, conjugation to a multifunctional protein (having at least two free amine groups) results in a conjugate in which a single molecule of the protein has one or more polysaccharide fragments covalently attached. As used herein, the terms "polysaccharide" or "polysaccharide fragments" will be used interchangeably in the context of conjugation reactions. It can readily be seen that the number of polysaccharides attached to the protein can be routinely regulated by changes in the conditions of the conjugation reaction, including the relative concentration of polysaccharide or polysaccharide fragments to protein and the overall concentration of the reactants. Of course, regulation of any reaction parameter, e.g., time, temperature, pH, etc., which affects the reactivity or rate of reaction will alter the final composition and structure of the conjugate.

When the polysaccharide fragment has at least one functional aldehyde group located on each end of the fragment, conjugation to a multifunctional protein can result in several types of conjugate. For example, conjugation of such reactants has the potential for forming a lattice or network structure, particularly where there are many free amines on the protein and capsular fragments are in low molar excess to protein. The degree of crosslinking and overall size of the network or lattice can be regulated by routine variation of the conditions of the conjugation reaction.

In one embodiment, the conjugation is carried out according to a reductive amination process known in the art. For example, the process may involve reacting the reducing polysaccharide fragment and carrier protein in the presence of cyanoborohydride ions, or another reducing agent which will not reduce the reducing ends of interest nor adversely affect the carrier protein or polysaccharide.

The cyanoborohydrate ions (or their equivalent) act primarily as a mild selective reducing agent of the Schiff base intermediate formed between the carbonyl groups of the polysaccharide fragment and amino groups of the protein. A secondary effect of such ions is the slower reduction of any active aldehyde groups remaining on the polysaccharide fragments after conjugation has occurred. Optionally, after conjugation, additional cyanoborohydrate ions (or their equivalent) may be added to reduce such unreacted free aldehyde groups. It is often desirable to add the stronger reducing agent, borohydride ion, after conjugation to ensure adequate reduction of the remaining carbonyl groups.

Polysaccharide-Protein Conjugates: Using Linkers

Success with the direct conjugation depends on how many surface groups are available to each reaction partner. Steric effects are known to influence the efficiency of conjugation of polysaccharides to protein. This can be overcome using highly flexible bifunctional linkers or spacer arms (linkers) to access otherwise inaccessible sites on the protein being conjugated. Linkers do not have any unified classification scheme, however the following characteristics are common: they are low molecular weight, bifunctional reagents capable of stepwise or simultaneous reactions with selected functional groups on the polysaccharide and protein. The bacterial polysaccharides can have a wide array of functional groups like hydroxyl groups, amino groups, which may or may not be acylated, phosphodiesters and carboxyl groups. Any of these functional groups, in principle, can be used for coupling of the linker to polysaccharide.

As discussed above, polysaccharides may be conjugated to carrier proteins through an intermediary or spacer molecule known as a linker. For example, according to the methods provided herein, reductive amination of the reducing end of an polysaccharide is performed using a molecule containing two amino groups. In a certain embodiment of the invention, reductive amination is accomplished by reacting a given molar amount of polysaccharide with a diaminoethane solution in 10× molar excess in 0.2M $KH_2PO_4$ at about pH=9 at a temperature of approximately 25-100° C., and preferably 100° C. for between about 1-60 minutes, and preferably about 15 minutes. Thereafter, a molar amount of pyridine borane equivalent to 25 times the molar concentration of polysaccharide in the preparation may be added, and the reaction is performed at between about 25-100° C., and preferably about 50° C. for between about 1 and 72 hours, preferably about 48 hours.

The resulting product of the reductive amination reaction may then be reacted with a "linker." As used herein, a "linker" is a bifunctional molecule, wherein both functional groups are capable of reaction with either the terminal amino group of the activated polysaccharide or amino groups present in the structure of the carrier protein, such that the bifunctional molecule may serve to link together the polysaccharide and the carrier protein. In one embodiment of the invention, the bifunctional group is a diester, and is, more particularly, a diester of adipic acid, which has been shown to be associated with more efficient glycosylation of protein. In a specific embodiment of the invention a polysaccharide, having been subjected to reductive amination, is further reacted with a succinimidyl diester of succinic or, more preferably, adipic acid; this reaction may best be performed with the aminated polysaccharide at a molar concentration (as amino groups) equivalent to about one-fifth of the molar concentration of succinimidyldiester of adipic acid (SIDEA) or succinimidyidiester of succinic acid (SIDES) in a solution of dimethylsulfoxide (DMSO) at between about 0° C. and about 25° C., and preferably about 4° C. for between about 0.5 and 5 hours and preferably about 2 hours. The activated polysaccharide may then be collected by precipitation using 1, 4 dioxane (80% v/v), which also leaves in the supernatant the excess of SIDEA (or SIDES).

In a specific embodiment of the invention, activated polysaccharides may be linked to $CRM_{197}$ protein which has been purified as follows: $CRM_{197}$, produced by the strain *Corynebacterium diphtheriae*, may be separated from culture medium by passing the bacterial culture through a Millipore membrane, thereby precipitating protein from the filtrate, and then purifying $CRM_{197}$ by ion exchange chromatography. Alternatively, substantially pure $CRM_{197}$ may be obtained by any method known in the art.

Activated polysaccharide may be covalently linked to carrier protein in the presence of an organic solvent and, optionally, any other agent (such as a condensing agent) in order to promote the linkage of the terminal functional group of the activated polysaccharide to the protein.

In a certain embodiment of the invention, activated polysaccharide bearing a terminal ester group may be covalently linked to free amino groups present on carrier protein as follows: Activated polysaccharide may be dissolved in dimethylsulfoxide and then added to an aqueous solution of carrier protein (for example, but not limited to $CRM_{197}$ at a concentration of about 2 mg/ml) such that the molar ratio of monoester-activated polysaccharide/total amino groups of the carrier protein is about 1:2 and the final concentration of DMSO is about 50% v/v. The conjugation reaction is performed at 4° C. and although the reaction is near to completion in about 2 hours, it is suitable to leave the reaction going overnight in order to increase the yield of reaction at the highest values for each type specific glycoconjugate. The glycoconjugates so obtained are then purified by gel chromatography.

Linkers

The use of linkers is known in the field of conjugate immunogenic compositions. Linking a polysaccharide to a carrier protein may be accomplished, for example, by using a cross linking reagent such as glutaraldehyde. However, in a certain embodiment, the polysaccharide and the protein carrier are separated by a linker. The linker promotes optimum immunogenicity of the conjugate and more efficient coupling of the polysaccharide with the carrier. Linkers separate the two antigenic components by chains whose length and flexibility can be adjusted as desired. Between the bifunctional sites, the chains can contain a variety of structural features, including heteroatoms and cleavage sites. Linkers also permit corresponding increases in translational and rotational characteristics of the antigens, increasing access of the binding sites to soluble antibodies. Besides adipic acid dihydrazide (ADH), suitable linkers include, for example, heterodifunctional linkers such as epsilon-aminohexanoic acid, 3-(2-pyridyidithio propionyl hydrazide (PDPH), chlorohexanol dimethyl acetal, D-glucuronolactone and p-nitrophenyl amine. Coupling reagents contemplated for use include hydroxysuccinimides and carbodiimides. Many other linkers and coupling reagents known to those of ordinary skill in the art are also suitable for use.

Where a carrier and one or more antigens such as a polysaccharide are conjugated (i.e., covalently associated), conjugation may be by any chemical method, process or genetic technique known in the art. For example, a carrier polypeptide and one or more antigens selected from a group comprising a carbohydrate, an oligosaccharide, a lipid, a lipooligosaccharide, a polysaccharide, an oligosaccharide-protein conjugate, a polysaccharide-protein conjugate, a peptide-protein conjugate, an oligosaccharide-peptide conjugate, a polysaccharide-peptide conjugate, a protein-protein conjugate, a lipooligosaccharide-protein conjugate, a polysaccharide-protein conjugate, or any combination thereof, may be conjugated by techniques, including, but not limited to: (1) direct coupling via protein functional groups (e.g., thiol-thiol linkage, amine-carboxyl linkage, amine-aldehyde linkage; enzyme direct coupling); (2) homobifunctional coupling of amines (e.g., using bis-aldehydes); (3) homobifunctional coupling of thiols (e.g., using bis-maleimides); (4) homobifunctional coupling via photoactivated reagents (5) heterobifunctional coupling of amines to thiols (e.g., using maleimides); (6) heterobifunctional coupling via photoactivated reagents (e.g., the β-carbonyidiazo family); (7) introducing amine-reactive groups into a poly- or oligosaccharide via cyanogen bromide activation or carboxymethylation; (8) introducing thiol-reactive groups into a poly- or oligosaccharide via a heterobifunctional compound such as maleimido-hydrazide; (9) protein-lipid conjugation via introducing a hydrophobic group into the protein and (10) protein-lipid conjugation via incorporating a reactive group into the lipid. Also, contemplated are heterobifunctional "non-covalent coupling" techniques such the Biotin-Avidin interaction. Other methods well known in the art for effecting conjugation of oligosaccharides and polysaccharides to immunogenic carrier proteins are also within the scope of some embodiments of the invention.

Immunogenic Compositions

In one aspect, the present invention relates to immunogenic compositions that include an effective amount of at least one saccharide, oligosaccharide, polysaccharide, polysaccharide-protein conjugate thereof, or biological equivalent thereof, described herein. For example, in one embodiment, the immunogenic composition includes at least one polysaccharide including a structure represented by formula (I) and/or a polysaccharide-protein conjugate thereof. In one embodiment, the immunogenic composition includes at least one polysaccharide including a structure represented by formula (II) and/or a polysaccharide-protein conjugate thereof. In another embodiment, the immunogenic composition includes at least one polysaccharide including a structure represented by formula (III) and/or a polysaccharide-protein conjugate thereof. In yet another embodiment, the immunogenic composition includes at least one polysaccharide including a structure represented by formula (IV) and/or a polysaccharide-protein conjugate thereof. In a further embodiment, the immunogenic composition includes at least one polysaccharide including a levan moiety and/or a polysaccharide-protein conjugate thereof.

In one embodiment, the immunogenic composition of the invention includes a pharmaceutically acceptable diluent and/or pharmaceutically acceptable carrier. Such pharmaceutically acceptable carriers are not to be confused with "carrier proteins", which are used in attaching the carbohydrate of the invention to a protein and, which modify the immune response to that carbohydrate. To avoid confusion with the protein carriers herein described, the term pharmaceutically acceptable diluent will be preferred over pharmaceutically acceptable carriers, but these terms may occasionally be used interchangeably.

Suitable pharmaceutically acceptable diluents include any and all conventional solvents, dispersion media, fillers, solid carriers, aqueous solutions, coatings, antibacterial and antifungal agents, isotonic and absorption delaying agents, and the like. Suitable pharmaceutically acceptable diluents include, for example, one or more of sterile water, water for injection (WFI), sterile isotonic saline, phosphate buffered saline, dextrose, glycerol, ethanol and the like, as well as combinations thereof. Pharmaceutically acceptable diluents may further comprise minor amounts of auxiliary substances such as wetting or emulsifying agents, preservatives or buffers, which enhance the shelf life or effectiveness in the body. The preparation and use of pharmaceutically acceptable diluents is well known in the art. Except insofar as any conventional media or agent is incompatible with the active ingredient, use thereof in the immunogenic compositions of the present invention is contemplated.

In certain embodiments, the immunogenic composition will include one or more adjuvants. As used herein, an "adjuvant" is a substance that serves to enhance the immunogenicity of an immunogenic composition of particular embodiments of the invention. Adjuvants are known in the art.

Methods

Methods of Use

In one aspect, the invention relates to a method of inducing an immune response in a mammal by administering to the mammal an effective amount of at least one of the saccharides described herein. In one embodiment, the method includes inducing an immune response against a Gram-positive coccus. Examples of Gram-positive cocci include *Staphylococcus* species, *Enterococcus* species, and *Streptococcus* species. In a preferred embodiment, the method includes inducing an immune response against an *Enterococcus* species, most preferably against *Enterococcus faecium*.

In another aspect, the invention relates to a method of inducing an immune response in a mammal by administering to the mammal an effective amount of a composition described herein, wherein the composition includes at least one of the saccharides described herein. In one embodiment, the method includes inducing an immune response against a Gram-positive coccus. Examples of Gram-positive cocci include *Staphylococcus* species, *Enterococcus* species, and *Streptococcus* species. In a preferred embodiment, the method includes inducing an immune response against an *Enterococcus* species, most preferably against *Enterococcus faecium*.

Diagnostic Uses

In yet another aspect, the invention relates to methods and uses of the saccharides described herein as a diagnostic marker. For example, in one embodiment, an isolated saccharide described herein may be useful for detecting the presence of a Gram-positive coccal antigen and/or antibody (such as, e.g., an *Enterococcus* antigen and/or an anti-*Enterococcus* antibody) in a sample. The sample may be from a mammal, from food or water, or other substance suspected of infection of a Gram positive coccus. Accordingly, in one aspect, the invention relates to a method of detecting a Gram positive coccus in a test sample. The method includes assaying the sample for the presence of at least one saccharide described herein. Examples of Gram-positive cocci include *Staphylococcus* species, *Enterococcus* species, and *Streptococcus* species.

The saccharides described herein may be used, for example, in carbohydrate-based pharmaceutical compositions, immunogenic compositions, and/or as research and diagnostic tools. For example, in one embodiment, a saccharide, oligosaccharide or polysaccharide described herein may be conjugated to one or more carriers suitable for development of diagnostic assays, including ELISAs and microarrays. Exemplary carriers for use in such assays include bovine serum albumin (BSA), keyhole limpet hemocyanine (KLH), biotin, a label, a glass slide or a gold surface.

In one aspect, the invention relates to a method for diagnosing a Gram-positive cocci infection, such as an infection from a *Staphylococcus* species, *Enterococcus* species, and *Streptococcus* species, in a mammal. The method includes (i) obtaining a saccharide as described herein; (ii) producing a monoclonal antibody that specifically recognizes and binds to said saccharide; (iii) reacting said monoclonal antibody with a biological sample from the mammal; and (iv) detecting the presence of antibody bound to the saccharide.

In another embodiment, the invention relates to a method of detecting whether a mammal has been infected with or exposed to a Gram-positive cocci infection, such as an infection from a *Staphylococcus* species, *Enterococcus* species, and *Streptococcus* species. The method includes (i) obtaining a saccharide as described herein; (ii) reacting an antibody, obtained from the mammal, with said saccharide; and (iii) detecting whether an antibody from the mammal recognizes and binds to said saccharide.

In one embodiment, the invention relates to a kit or set for the detection and/or identification of bacteria belonging to the species *Enterococcus* or to a related microorganism. For example, the kit may be include reagents such as a labeled or labelable compound or agent, such as a monoclonal antibody, capable of detecting a saccharide described herein in a biological sample.

Antibodies Immunoreactive with Saccharides Described Herein

In one aspect, the present invention relates to an antibody immunoreactive with a saccharide described herein. The antibody preparation may include any one of a polyclonal antibody, monoclonal antibody, mouse monoclonal IgG antibody, humanized antibody, chimeric antibody, fragment thereof, or combination thereof. An antibody may be generated in a mammal by using this polysaccharide and then the antibody may be used in assays for detecting antigens indicative of *Enterococcus* infection from the gastric fluids of potentially infected subjects.

Antibody responses to repeat structures such as a polysaccharide of the present invention may exhibit some unique features. For example, the regularity of the repeating units may mean that antigen molecules of vastly different molecular weights can bind to antibodies specific for the polysaccharide. Second, the repeat structures of the larger length polysaccharides are capable of inducing T-cell independent antibody responses. Therefore, when using polysaccharides conjugated to protein carriers having T-cell helper epitopes, both T-cell independent and T-cell dependent antibody responses can be stimulated. Therefore, immune response can be modified by appropriate selection of polysaccharide size and whether or not a carrier protein is used.

In one aspect, the invention relates to an isolated antibody or fragment thereof that specifically binds to a saccharide described herein. An "isolated" antibody as used herein refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In exemplary embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. An isolated antibody includes the antibody in situ within recombinant cells since at least one component of the antibody's natural environment will not be present. Ordinarily, however, an isolated antibody will be prepared by at least one purification step.

An antibody that "specifically binds to" or is "specific for" a particular saccharide or an epitope on a particular saccharide is one that binds to that particular saccharide or epitope on a particular saccharide without substantially binding to any other saccharide or saccharide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

Polyclonal Antibodies

In certain embodiments, the anti-polysaccharide antibody is a polyclonal antibody. Polyclonal antibodies, as defined herein, refers to a mixture of antibodies having differing specificities derived from a preparation of serum and originating from different B-cell clones. The preparation and characterization of polyclonal antibodies are known in the art.

Polyclonal antibodies are raised in a mammal, for example, by administering one or more injections of an immunogen or immunogenic composition described herein and, if desired, an adjuvant, buffer, and/or diluent. A range of animal species may be used for the production of specific antisera. Typically an animal used for production of anti-saccharide polyclonal antisera is a rabbit, a mouse, a rat, a hamster or a guinea pig. Typically, the immunogen or immunogenic composition with or without the adjuvant is injected in the mammal by multiple injections. The immunogenic material may include a saccharide, oligosaccharide, polysaccharide, polysaccharide-protein conjugate described herein, or a larger assembly of immunogens. Typically, beginning 2-6 weeks after the first immunization, blood is collected from the immunized animal, allowed to clot and serum is harvested. The serum contains the anti-saccharide polyclonal antibodies from the immunized animal and is often referred to as antisera.

Monoclonal Antibodies

An anti-saccharide monoclonal antibody may be prepared through use of known hybridoma techniques. Typically, preparing monoclonal antibodies involves first immunizing a suitable target animal host with a selected immunogen comprising a saccharide, oligosaccharide, polysaccharide or polysaccharide-protein conjugate of the present invention. If desired, an adjuvant, buffer, and/or diluents may be included. The immunization is conducted in a manner sufficient to elicit B lymphocytes to produce or express antibodies that specifically bind to the saccharide or conjugate thereof. Alternatively, the lymphocytes are immunized in vitro.

The lymphocytes are then fused with an immortalized cell line using a suitable fusing agent, such as polyethylene glycol, to form a hybridoma cell. The source of the lymphocytes determines whether the monoclonal antibodies are of human or animal origin. In general, peripheral blood lymphocytes ("PBLs") are used if antibodies and cells of human origin are desired, and spleen cells or lymph node cells are used if non-human mammalian sources are desired.

Immortalized cell lines are typically transformed mammalian cells, particularly myeloma cells of rodent, bovine and human origin. Usually, rat or mouse myeloma cell lines are employed. The hybridoma cells are cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Immortalized cell lines are chosen for practical considerations such as species of origin, fusion and growth characteristics. For example, suitable immortalized cell lines are those that fuse efficiently, support stable high level expression of antibody by the selected antibody-producing cells, and are sensitive to a medium such as HAT medium. Examples of immortalized cell lines include: murine myeloma lines. Human myeloma and mouse-human heteromyeloma cell lines also have been described for the production of human monoclonal antibodies.

The monoclonal antibody is secreted into the culture medium by the hybridoma cells. The culture medium is then assayed for the presence of monoclonal antibodies that recognize and bind the polysaccharide. The anti-polysaccharide binding specificity of particular monoclonal antibodies produced by the hybridoma cells is determined by one of numerous procedures that are well known in the art. For example, antibody binding specificity may be determined by immunoprecipitation, radioimmunoassay (RIA), western blot, enzyme-linked immunoabsorbent assay (ELISA) or surface plasmon resonance (e.g. Biacore). The precise epitope recognized by the monoclonal antibody is determined by epitope mapping. Such techniques and assays are well known in the art.

After hybridoma cells producing antibodies with the desired specificity are identified, the clones are subcloned by limiting dilution and cultured using standard methods. Suitable culture media for this purpose include, for example, Dulbecco's Modified Eagle's Medium and RPMI-1640 medium. Alternatively, the hybridoma cells are grown in vivo as ascites in a mammal. The monoclonal antibodies secreted by the subclones are isolated or purified from the culture medium or ascites fluid by conventional immunoglobulin purification procedures such as, for example, protein A-Sepharose, hydroxylapatite chromatography, gel electrophoresis, dialysis, or affinity chromatography.

Alternatively, antibodies having the desired specificity and from the desired species of origin can be obtained through the use of phage display libraries. Additionally, examples of methods and reagents particularly amenable for use in generating and screening antibody display library can be found in the art.

Uses of Antibodies

In one aspect, the invention relates to use of a saccharide described herein for detecting or producing a Gram-positive cocci antibody and/or antibody fragment, such as, for example, an *Enterococcus* antibody and/or antibody fragment. The saccharides described herein and/or antibodies generated therefrom may be used in a variety of immunodiagnostic techniques known to those of skill in the art, including ELISA- and microarray-related technologies. In addition, these reagents may be used to evaluate antibody responses, including serum antibody levels, for example, to immunogenic saccharide conjugates. The assay methodologies of the invention may involve the use of labels such as fluorescent, chemiluminescent, radioactive, enzymatic labels or dye molecules, and/or secondary immunologic reagents for direct or indirect detection of a complex between an antigen or antibody in a biological sample and a corresponding antibody or antigen bound to a solid support.

The antibody or antibody fragment produced may also be useful in passive immunotherapy or for prophylaxis against a Gram-positive cocci infection, such as, for example, an *Enterococcus* infection.

Method of Producing a Saccharide

In yet another aspect, the invention relates to a method for producing at least one of the saccharides described herein. The method includes culturing a Gram positive coccus and collecting the saccharide produced by the bacterium. In one embodiment, the Gram-positive coccus includes a *Staphylococcus* species, *Enterococcus* species, and *Streptococcus* species. In one embodiment, the bacterium is an *Enterococcus* bacterium. In one embodiment, the bacterium is *Enterococcus faecium*. The bacterium may be any strain of *E. faecium*. In a preferred embodiment, the bacterium is *E. faecium* TX0016 (DO; E1794). In another preferred embodiment, the bacterium is *E. faecium* E0155. In a further embodiment, the bacterium is *E. faecium* E155 (Freiburg).

A saccharide described herein may be produced by culturing the Gram positive coccus in an appropriate medium. An appropriate medium may include Columbia broth. The medium may include dextrose, hemin, and/or glucose. Preferably, the medium includes Columbia broth and dextrose. If *E. faecium* is cultured using Columbia broth and dextrose, preferably the temperature for culture is 20 to 40° C., preferably 37° C. In a preferred embodiment, the bacterium is cultured under aerobic conditions. In another preferred embodiment, the bacterium is cultured for 12 to 60 hours.

A saccharide may be collected from the obtained culture by using a method known in the art to collect a target substance from a culture, such as, for example, heating, enzyme treatment, centrifugation, and/or filtration. In one embodiment, the culture containing the bacterium and saccharide is centrifuged and treated with an enzyme, such as, for example, lysozyme, RNase, DNase, and/or Pronase. For example, in one embodiment, an appropriate organic solvent is added to the obtained supernatant to precipitate proteins, and the precipitate is removed by centrifugation. Then a saccharide may be precipitated by further adding an appropriate organic solvent to the supernatant, and the saccharide may be collected by centrifugation. More specifically, a saccharide described herein may be obtained by adding ethanol at a final concentration of about 25 volume % to the supernatant from which the bacterium has been removed, removing a precipitation that contains protein by centrifugation, further adding ethanol to a final concentration of about 75 volume % thereto, and then collecting a precipitate by centrifugation. The resulting precipitate may be dried with nitrogen. The resulting precipitate may be resuspended in Tris and 0.05% Na Azide.

Alternatively, in another embodiment of the invention, the saccharide is chemically synthesized. The saccharide may be chemically synthesized according to conventional methods.

In yet another embodiment of the invention the saccharide is prepared by expression in a surrogate host after cloning and expressing a biosynthetic pathway to produce the saccharide. For example, a host cell may be modified to produce a saccharide having structural similarity to a saccharide described herein, wherein a repeating unit of the saccharide produced in the host cell is partially identical to a repeating unit of a saccharide described herein. A saccharide is structurally similar to a saccharide described herein if, for example, a repeating unit of the saccharide has a missing branch, is heterogeneous in size and/or is heterogeneous in branching arrangement, as compared to a repeating unit of a saccharide described herein. Preferably, the host cell is a bacterial host cell.

EXAMPLES

Example 1: *E. faecium* Strains

Two strains associated with clonal complex 17 (CC17), TX0016(DO) and strain E155 (Freiburg), were selected for for analysis of surface carbohydrates. The TX0016 strain isolated originally from an endocarditis patient is resistant to polymorphonuclear leukocyte [PMN]-mediated killing.

Example 2: Fermentation 500 mL seed cultures were grown overnight at 37° C. without aeration in Columbia broth with 2% Dextrose. The entire volume was added to 7.5 L of the same media in an 8 L stirred tank reactor under pH control and grown for 6 h or 24 h. After killing by heat treatment (1 h 60° C.), cells were harvested by centrifugation, resuspended in 150 ml Tris/Sucrose buffer, and treated overnight with 1 mg/ml lysozyme and 10 U/ml mutanolysin. After centrifugation (10,000 rpm, 20 min) the supernatant was treated with 100 μg/ml RNase and 10 U/ml DNase for 8 hours, and then Pronase (50 μg/ml) overnight. Ethanol was added to 25% and the precipitate discarded after centrifugation. The supernatant was adjusted to 75% ethanol and the resulting precipitate retained. After washing twice with 75% ethanol, the pellet was dried with nitrogen and resuspended in 20 ml of 30 mM Tris pH 7.5 and 0.05% Na Azide. In this way, 2-3 g of crude carbohydrate was obtained from 50-100 g of wet cells.

Example 3: Antigen Purification

Crude polysaccharide was loaded on a size exclusion chromatography (SEC) Sephacryl S-400 column (16/60 and 26/60 columns in a series) equilibrated with 50 mM Tris pH 7.5/100 mM NaCl with 0.5 ml/min flow rate. Fractions were monitored by UV absorption at 215 nM, 254 nM and 280 nM, by native PAGE gel electrophoresis with Stains-All detection reagent and with carbohydrate biochemical assays (anthrone, deoxy-sugarO-acetyl). For polysaccharide extracted from TX0016 (DO) strain, recovered fractions were consolidated into 5 pools corresponding to the major peaks with anthrone activity. The first four SEC pools contained high molecular weight material by Stains-All staining; the fifth did not and was not studied further. Individual SEC pools were applied to an anion exchange column chromatography (AEC) column (2× HiTrap Q HP in series) equilibrated with 25 mM Tris/50 mM NaCl and carbohydrates eluted with a 1M NaCl gradient. Fractions were screened as described above and samples corresponding to peak activities of interest were pooled, concentrated with 30 KDa MWCO spin filters, dialyzed against water and freeze-dried prior to biochemical analysis.

Example 4: Antigen Structural Analysis

Structural determination of carbohydrate samples involved $^1$H-NMR and 2D-NMR analysis (DQCOSY, TOCSY, NOESY/ROESY and $^1$H/$^{13}$C HSQC). Monosaccharide composition was determined by GC-MS of alditol acetate derivatives. Samples were methylated by the Ciucanu and Kerek procedure (*Carbohydr Res.* 1984; 131:209-217). The partially methylated derivatives were converted to the corresponding alditol acetates and were analyzed by gas chromatography (GC) coupled to high orifice voltage ESI mass spectrometry.

Example 5: Determination of Molecular Weight

Weight-average molecular weight (Mw) of purified polysaccharides was determined by size-exclusion chromatography (SEC) coupled with online differential refractive index (dRI), ultraviolet (UV) and multi-angle laser light scattering (MALLS) triple detection system. For size exclusion chromatography, sized-based separation of polysaccharides was performed on a TSK-gel GMPWxl mixed-bed analytical column, with isocratic elution at a flow rate of 0.8 mL/min using aqueous PBS buffer (pH 6.8) as mobile phase. For detectors, an OptiLab rex dRI, a TREOS three-angle MALLS detector (both from Wyatt Technology) and a Varian single-wavelength UV detector were used. A generic do/dc value of 0.133 mL/g was used for all polysaccharide samples for the Mw determination by SEC-UV-RI-MALLS. Data acquisition and analysis were performed using Wyatt Technology ASTRA software (v. 5.3.4.20).

Example 6: Structural Analysis of *E. faecium* Pf1 Polysaccharide

This polysaccharide eluted as a single peak near the void volume by SEC and passing through the AEC without binding. It was identified as a levan-like polymer associated with *Bacillus* and may promote tolerance to environmental stress, such as, for example, heat, cold, freezing temperatures, starvation, etc).

Monosaccharide analysis of the sample (GC of alditol acetates) showed the presence of glucose and mannose in equal amount. $^1$H-NMR spectrum contained no anomeric signals but multiple signals between 3.5 and 4.3 ppm were present and no evidence of protein or other impurities. These data show that the polymer was built from fructose, which gives Man and Glc upon reduction. Analysis of the 2D NMR data (Table 1, FIG. 1) indicated that polymer mostly had regular structure with the -6-β-D-Fruf-2- (Levan) repeating unit. The linkage type was determined by comparison of the spectra with published data for various fructose polymers. Spectra contained minor signals of fructose of undefined origin, possibly ends of chain or different substitution type.

TABLE 1

NMR data for PF1 sample. 600 MHz, 25° C. Acetone reference 2.23/31.45 ppm.

|  | H/C-1 | H/C-2 | H/C-3 | H/C-4 | H/C-5 | H/C-6 |
| --- | --- | --- | --- | --- | --- | --- |
| Fru | 3.67; 3.77 |  | 4.19 | 4.10 | 3.95 | 3.56; 3.90 |
|  | 61.2 | 105.5 | 77.5 | 76.4 | 81.5 | 64.6 |

Example 7: Structural Analysis of *E. faecium* Pf2 Polysaccharide

Figure 3:
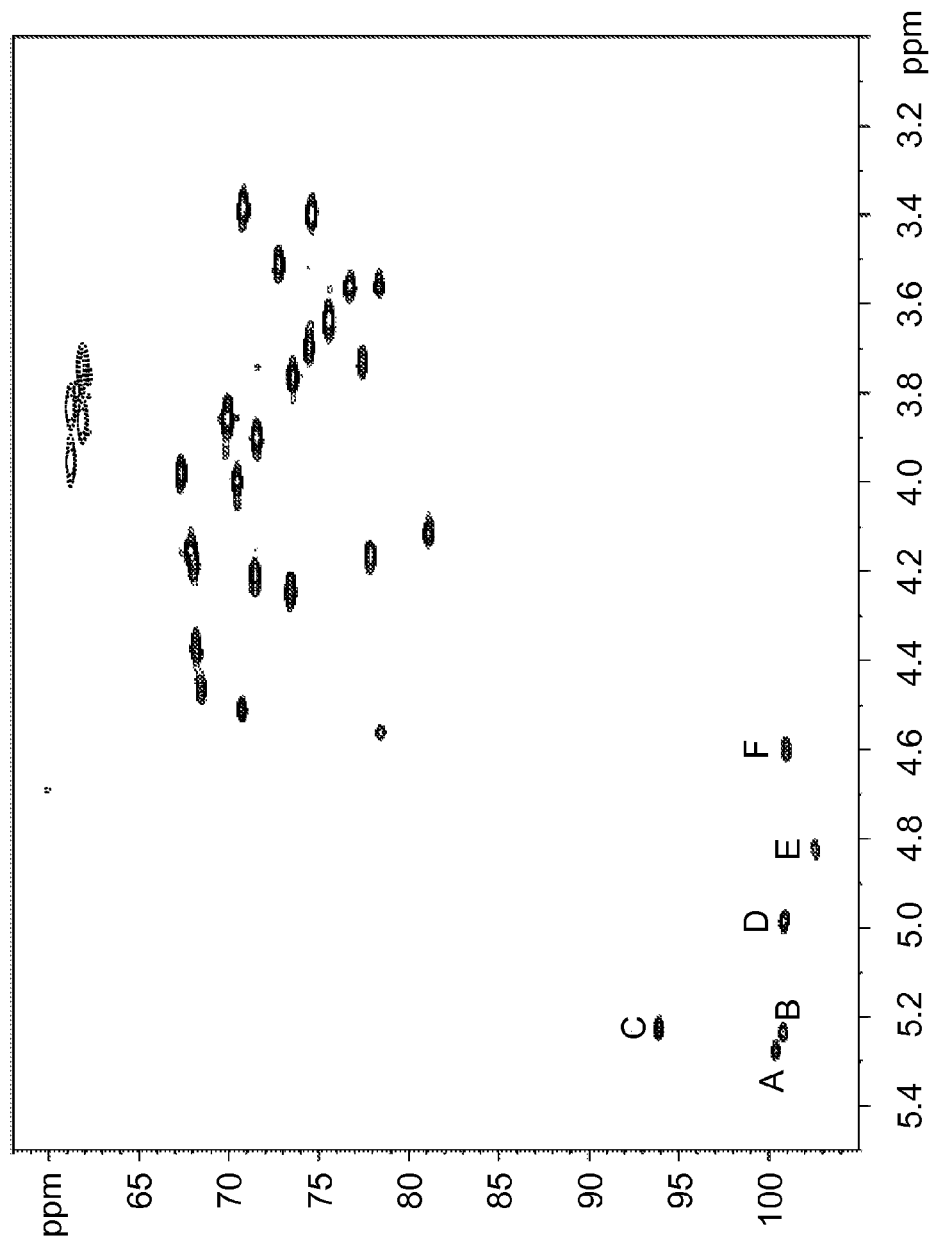
FIG. 3 shows a fragment of the $^1$H-$^{13}$C HSQC spectrum of Pf2 polysaccharide.

This polysaccharide was purified from the second SEC pool by anion exchange chromatography. The anthrone positive peak eluted from the AEC column with 0.22M NaCl. The sample was concentrated and desalted on Sephadex G-15 prior to NMR analysis (FIGS. 2, 3). GC analysis of the alditol acetates prepared by acid hydrolysis of the PS showed the presence of fucose and glucose in amount of 3:2. A set of 2D NMR spectra of the PS (DQCOSY, TOCSY, NOESY/ROESY and $^1$H/$^{13}$C HSQC) was recorded and assigned (Table 2, FIG. 3). Spectra contained spin systems of six monosaccharides. Three fucose, two glucose and a monosaccharide with TOCSY signal pattern and vicinal H—H coupling constants typical for β-galacturonic acid in pyranose form were identified. The identification of the uronic acid was not definitive, since in an attempt to determine its absolute configuration by GC-MS of acetylated glycosides/esters with optically pure 2-butanol no derivatives of galacturonic acid were found. $^{13}$C NMR data of this monosaccharide were not consistent with the expected values of β-galacturonic acid. Also, no NOE correlation between H-1 and H-5, which is typical for β-Gal, was observed. This situation pointed to the presence of α-L-altruronic acid in $^4C_1$ conformation, which has a ring configuration the same as β-Gal and equatorial H-5, resulting in the absence of NOE between H-1 and H-5.

Connections between monosaccharides in the PS were identified on the basis of NOE correlations (A1:B1,2; B1:E3; C1:B3; D1:F4; F1:C3) and $^{13}C$ chemical shifts. Analysis of the substitution effects showed that assuming that glucose has D-configuration fucose should have an L-configuration.

Figure 4:
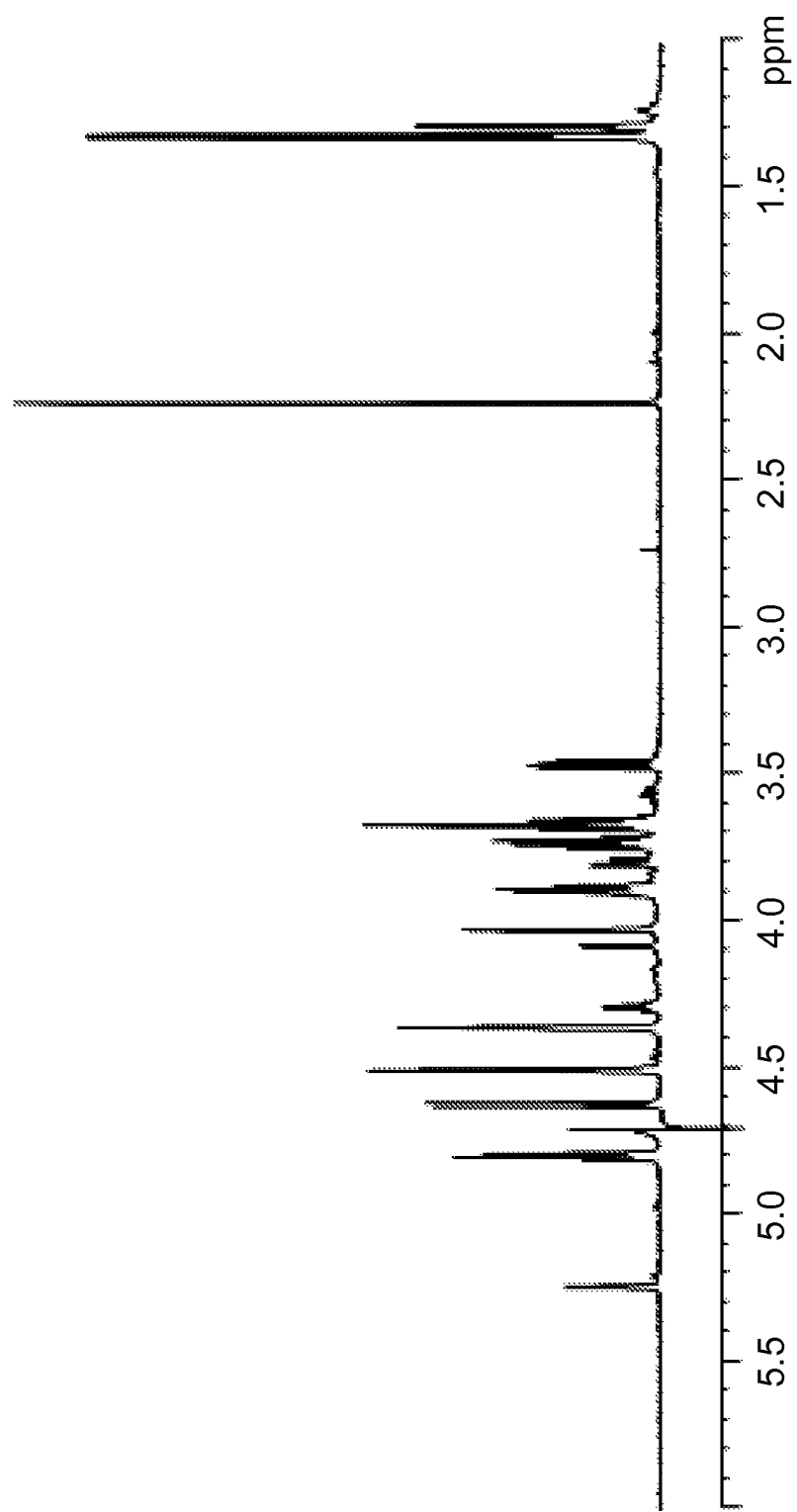
FIG. 4 shows a $^1$H NMR spectrum of the Pf2 OS1 oligosaccharide.

To further explore the tentative identification of uronic acid partial hydrolysis of the PS was done (0.5 M TFA, 90° C., 2 h). It afforded an acidic disaccharide (OS1), which was isolated by anion-exchange chromatography and gel chromatography on Sephadex G-15. It generated a clean, completely interpretable NMR spectra (FIG. 4, Table 3). The assignment of NMR spectra confirmed that uronic acid had α-altro-configuration.

Figure 5:
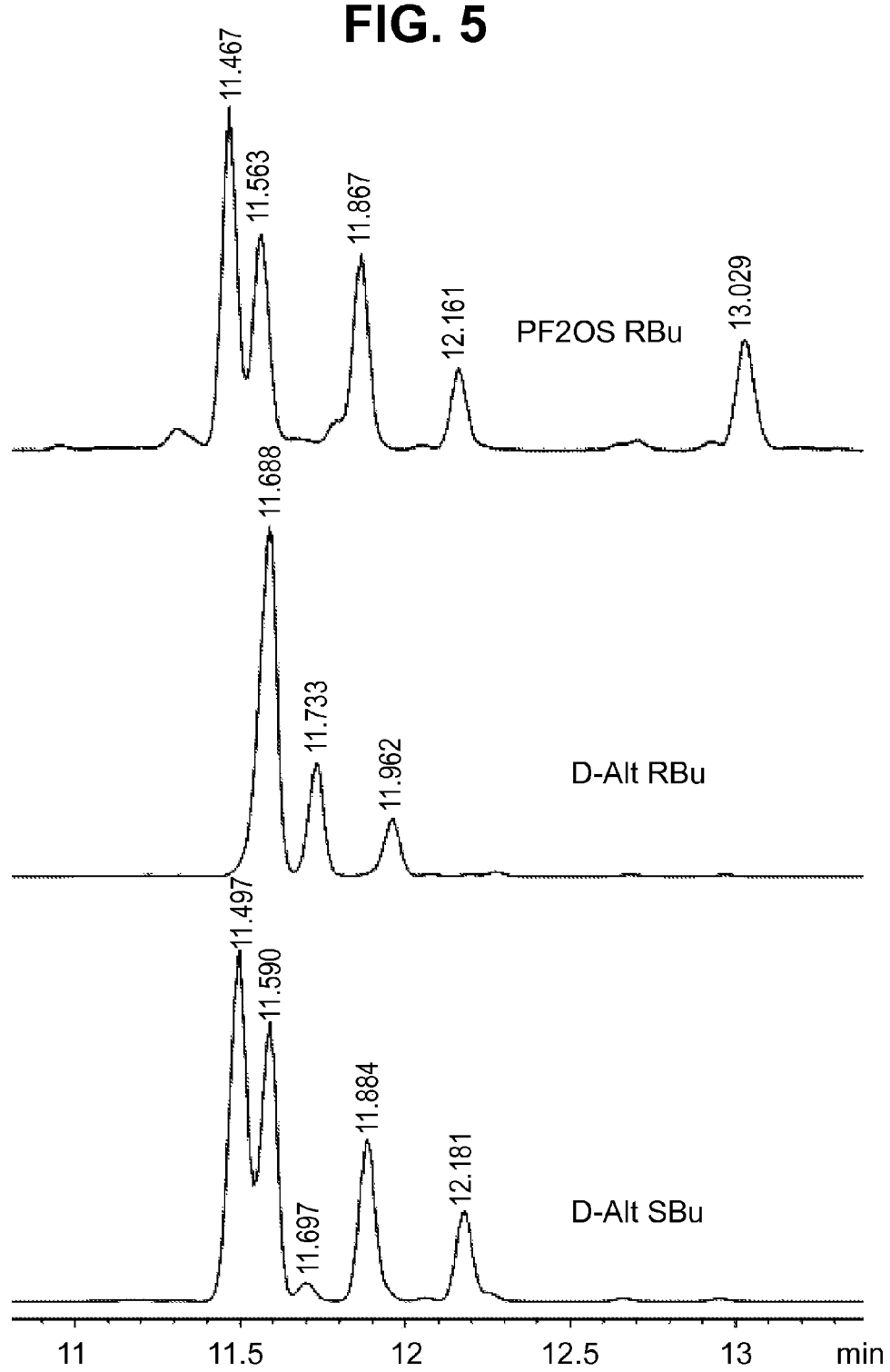
FIG. 5 shows GC traces of acetylated 2-butyl glycosides derived from Pf2 OS1 oligosaccharide and D-altrose.

Absolute configurations of L-fucose and D-glucose were determined by GC analysis of the acetylated 2-butyl glycosides prepared with optically pure isomers of 2-butanol. For the identification of the absolute configuration of altruronic acid OS1 was treated with 1M HCl/MeOH (90° C., 2 h) to obtain methyl ester, reduced with $NaBH_4$ in water (2 h, 30° C.), excess of $NaBH_4$ was destroyed with 4 M HCl, boric acid evaporated with methanol twice, residue treated with (R)-2-BuOH-AcCl (10:1) for 3 h at 90° C., dried and acetylated. GC analysis of the product showed that it was identical to the standard prepared from D-altrose and (S)-2-BuOH and differed from the derivative obtained with (R)-2-BuOH, indicating L-configuration of altruronic acid (FIG. 5).

Methylation analysis (Ciucanu-Kerek procedure, GC of partially methylated alditol acetates) showed the presence of 3-, 4-, and 2,3-substituted fucose, terminal and 4-substituted glucose, in agreement with NMR data.

High orifice voltage ESI mass spectra of the polysaccharide confirmed its structure, containing prominent peak at 937.7 amu (negative mode) or 939.7 amu (positive mode), which corresponded to repeating unit less one $H_2O$ (calculated exact mass 938.3 amu), but no significant structural information could be deduced from these spectra. Other peaks corresponded to addition or loss of hexose (162) or 6-deoxy hexose (146) residues.

TABLE 2

NMR data for PS Pf2 and proposed structure ($D_2O$, 32° C., 600 MHz).

| Unit | | H/C-1 | H/C-2 | H/C-3 | H/C-4 | H/C-5 | H/C-6a; b |
|---|---|---|---|---|---|---|---|
| A α-Glc | H | 5.27 | 3.51 | 3.69 | 3.38 | 3.76 | 3.75; 3.85 |
| | C | 100.3 | 72.8 | 74.4 | 70.7 | 73.5 | 61.8 |
| B α-Fuc | H | 5.23 | 4.21 | 4.24 | 4.15 | 4.18 | 1.27 |
| | C | 100.8 | 71.4 | 73.4 | 67.8 | 68.0 | 16.5 |
| C α-Fuc | H | 5.22 | 3.98 | 4.17 | 4.00 | 4.37 | 1.24 |
| | C | 93.8 | 67.3 | 77.8 | 70.4 | 68.1 | 16.5 |
| D α-Fuc PS | H | 4.98 | 3.84 | 3.86 | 4.11 | 4.46 | 1.28 |
| | C | 100.9 | 69.9 | 69.9 | 81.1 | 68.5 | 16.5 |
| D α-Fuc OS1 | H | 5.24 | 3.79 | 3.88 | 4.08 | 4.29 | 1.29 |
| | C | 93.3 | 69.7 | 69.5 | 81.0 | 67.6 | 16.6 |
| D β-Fuc OS1 | H | 4.62 | 3.46 | 3.67 | 4.02 | 3.89 | 1.32 |
| | C | 97.2 | 73.2 | 73.1 | 80.1 | 71.9 | 16.7 |
| E α-L-AltA PS | H | 4.82 | 3.90 | 3.73 | 4.51 | 4.57 | |
| | C | 102.6 | 71.5 | 77.3 | 70.7 | 78.3 | |
| E α-L-AltA OS1 | H | 4.79 | 3.73 | 3.66 | 4.36 | 4.50 | |
| | C | 102.3 | 71.5 | 71.1 | 70.6 | 77.8 | |
| | J, Hz | $J_{1,2}$ 7 | $J_{2,3}$ 9.4 | $J_{3,4}$ 3 | $J_{4,5}$ 3 | | |
| F β-Glc | H | 4.60 | 3.40 | 3.63 | 3.56 | 3.56 | 3.83; 3.95 |
| | C | 100.1 | 74.5 | 75.5 | 78.3 | 76.7 | 61.2 |

Pf2 structure:

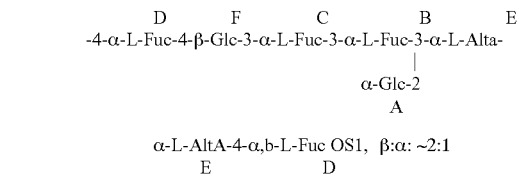

Example 8: Structural Analysis of *E. faecium* Pf3 Polysaccharide

This polysaccharide was identified from the first and second SEC pools, eluting from the AEC column with 0.58M NaCl. It showed only very weak anthrone activity. After a preliminary $^1$H-NMR study these samples were combined and desalted on Sephadex G15, and called PF3 due to the presence of a teichoic acid compound. A set of 2D NMR spectra of the PF3 (DQCOSY, TOCSY, ROESY, $^1H/^{31}P$ HMQC and $^1H/^{13}C$ HSQC) was recorded and assigned (Table 3). Spectra contained spin systems of three monosaccharides, all α-Glcp, and phosphorylated glycerol. The structures of four discrete structural units representing the glycerol phosphate backbone with or without and mono and disaccharide substitutions are shown below:

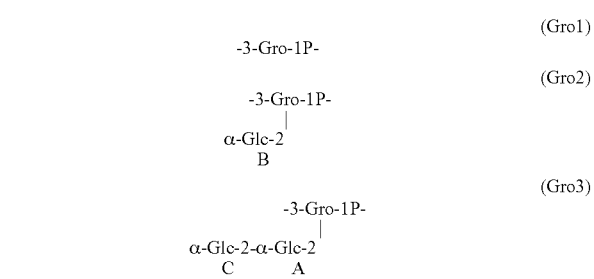

Lipid signals were present (hump around 1 ppm H), suggesting that the carbohydrate is a cell membrane anchored lipoteichoic acid. The lipid was not analyzed further. The non-glycosylated structure is prominent (Gro1) and present in approximately equal proportions to the glycosylated (Gro2+Gro3). Mono and di saccharide modified units were present in equal proportions (Gro2=Gro3). Connections between monosaccharides were identified on the basis of NOE correlations (A1:Gro3-2; B1:Gro2-2; C1:A1, 2) and $^{13}C$ chemical shifts. $^1H$-$^{31}P$ HMQC showed correlations between glycerol H-1 and H-3 with $^{31}P$ at 0.4 ppm (FIG. 6). The 3-Gro-1P- unit may be present at the polymer terminus. The presence of this lipoteichoic acid in high molecular weight SEC fractions reflects its micellular nature. PAGE analysis confirmed that the Pf3 migrates as a low molecular weight compound in the presence of SDS detergent. Compounds of identical structure but minus the lipid tail were also purified by AEC from SEC pools 3 and 4.

TABLE 3

NMR data for Pf3 (D₂O, 28° C., 600 MHz).

| Unit | | H/C-1 | H/C-2 | H/C-3 | H/C-4 | H/C-5 | H/C-6a; b |
|---|---|---|---|---|---|---|---|
| Glc A | H | 5.46 | 3.69 | 3.89 | 3.48 | 3.96 | 3.78-3.89 |
|       | C | 95.9 | 75.4 | 72.4 | 70.6 | 73.0 | 61.7 |
| Glc B | H | 5.19 | 3.54 | 3.77 | 3.42 | 3.94 | 3.78-3.89 |
|       | C | 99.0 | 72.7 | 74.2 | 70.8 | 73.0 | 61.7 |
| Glc C | H | 5.18 | 3.59 | 3.82 | 3.46 | 3.92 | 3.78-3.89 |
|       | C | 96.6 | 72.4 | 73.7 | 70.6 | 73.0 | 61.7 |
| Gro1  | H | 3.93 | 4.07 | 4.00 | | | |
|       | C | 67.6 | 70.5 | 67.6 | | | |
| Gro2  | H | 4.05 | 4.14 | 4.05 | | | |
|       | C | 65.9* | 76.5 | 66.4* | | | |
| Gro3  | H | 4.05 | 4.22 | 4.05 | | | |
|       | C | 65.9* | 76.1 | 66.4* | | | |
| Gro4  | H | 3.89; 3.94 | 3.92 | 3.62; 3.68 | | | |
|       | C | 67.6 | 71.9 | 63.2 | | | |

Signals marked with * can be interchanged.

Pf3 structure

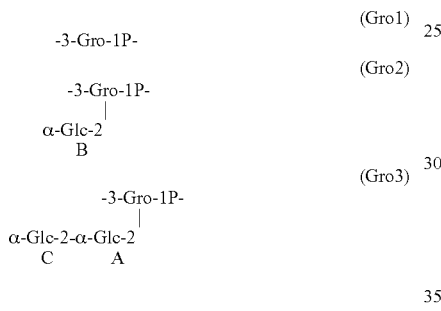

Example 9: Structural Analysis of *E. faecium* Pf4 Polysaccharide

The Pf4 carbohydrate was recovered from SEC pools 3 and 4, eluting from AEC with 1.2M NaCl. Samples were heterogeneous, containing a predominant heteroglycan with heteroheptameric repeat structure with small amounts of rhamnan and peptide contaminants. Heterogeneity was evident due to the presence by NMR analysis of two non-stoichiometric glucose residues. The minor polymer is apparently made of 3 Rha repeating units. As it was not possible to purify them further by anion-exchanger (retained) and Sephadex G50 (eluted with void volume), these minor contaminants may be covalently linked to the primary polysaccharide. Monosaccharide compositional analysis identified Rha, Glc, and Gal in a ratio of ~1:3:3. NMR analysis of the sample (FIG. 7) and derived fragments (below) led to the following structure, where the side-chain Glc was linked to the residues H and D:

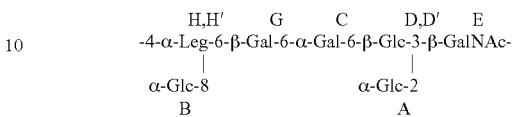

H' and D' are monosubstituted. Glc A and B are ~50%. Leg is legionaminic acid (5,7-diacetamido-3,5,7,9-tetradeoxy-D-glycero-D-galacto-nonulosonic acid), having all axial ring protons (large coupling constants, ~10 Hz), and NMR shifts of H/C 7-9. Partial acid hydrolysis with 0.5 M TFA (90° C., 1.5 h) produced mixture of the oligosaccharides and higher molecular mass peak containing all unidentified components of the PF4. The minor Rhamnan was not recovered and probably completely depolymerized. Oligosaccharides were separated by anion-exchange chromatography to give a neutral mixture OS1 and acidic disaccharide OS2:

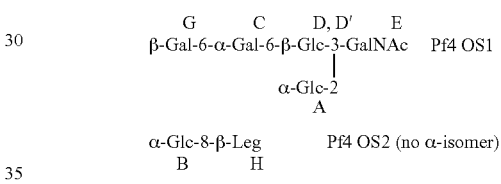

OS1 was heterogenous due to partial substitution with Glc A and Gal G (Gal G was partially lost due to hydrolysis). NMR spectra of the OS1 were generally in agreement with expectations, detailed assignment was not done due to presence of too many variants. MS (negative ions) showed Hex2HexNAc1 (m/z 544.6), Hex3HexNAc1 (m/z 706.7), and Hex4HexNAc1 (m/z 868.8). NMR data for Pf4 OS2 are shown in the Table 4. Negative mode ES MS m/z 495.4 (calculated molecular mass 496.19). Configurations of Glc, Gal, GalN were determined and found to be all D. GC analysis of the alditol acetates with internal inositol shows that this main Pf4 polysaccharide constitutes about 80% of the sample mass relative to contaminants.

TABLE 4

NMR data for P4 and proposed structure (D₂O, 40° C., 600 MHz).

| Unit | | H/C-1 | H/C-2 | H/C-3(a, e) | H/C-4 | H/C-5 | H/C-6a; b | H/C-7 | H/C-8 | H/C-9 |
|---|---|---|---|---|---|---|---|---|---|---|
| Glc A | H | 5.28 | 3.52 | 3.76 | 3.45 | 4.00 | 3.77; 3.83 | | | |
|       | C | 97.9 | 72.8 | 74.1 | 70.5 | 72.9 | 61.7 | | | |
| Glc B | H | 5.06 | 3.50 | 3.55 | 3.41 | 3.52 | 3.76; 3.84 | | | |
|       | C | 95.7 | 72.5 | 73.4 | 70.5 | 74.3 | 61.7 | | | |
| Gal C | H | 5.00 | 3.85 | 3.89 | 4.05 | 4.09 | 3.84; 4.07 | | | |
|       | C | 99.4 | 69.4 | 70.5 | 70.4 | 70.9 | 70.0 | | | |
| β-Glc D | H | 4.70 | 3.51 | 3.56 | 3.54 | 3.64 | 3.76; 3.98 | | | |
|         | C | 104.1 | 77.0 | 75.9 | 70.6 | 75.2 | 67.1 | | | |
| β-Glc D' | H | 4.50 | 3.30 | 3.46 | 3.53 | 3.61 | 3.75; 3.99 | | | |
|          | C | 105.7 | 74.0 | 76.9 | 70.5 | 75.2 | 67.0 | | | |
| β-GalNAc E | H | 4.58; 4.61 | 3.89; 3.88 | 3.88 | 4.13 | 3.67 | 3.76; 3.82 | | | |
|            | C | 103.0; 102.8 | 52.7 | 81.4 | 69.1 | 75.6 | 62.1 | | | |

TABLE 4-continued

NMR data for P4 and proposed structure (D₂O, 40° C., 600 MHz).

| Unit | | H/C-1 | H/C-2 | H/C-3(a, e) | H/C-4 | H/C-5 | H/C-6a; b | H/C-7 | H/C-8 | H/C-9 |
|---|---|---|---|---|---|---|---|---|---|---|
| β-Gal G | H | 4.44 | 3.52 | 3.65 | 3.94 | 3.78 | 3.65; 3.90 | | | |
| | C | 104.4 | 72.0 | 73.7 | 69.7 | 74.5 | 64.7 | | | |
| α-Leg H | H | | | 1.79; 2.89 | 3.72 | 3.79 | 4.15 | 3.97 | 3.94 | 1.35 |
| | C | | | 41.1 | 77.7 | 51.8 | 73.6 | 54.3 | 73.2 | 15.7 |
| α-Leg H' | H | | | 1.79; 2.89 | 3.72 | 3.75 | 4.04 | 3.90 | 4.01 | 1.26 |
| | C | | | 41.1 | 77.7 | 51.9 | 75.0 | 54.4 | 69.8 | 19.7 |
| β-Leg H OS2 | H | | | 1.87; 2.30 | 3.94 | 3.75 | 4.14 | 4.03 | 3.86 | 1.20 |
| | C | | 96.7 | 40.6 | 68.3 | 54.0 | 71.5 | 53.8 | 73.0 | 15.6 |
| α-Glc B OS2 | H | 5.02 | 3.49 | 3.54 | 3.40 | 3.51 | 3.75; 3.83 | | | |
| | C | 95.7 | 72.4 | 73.3 | 70.5 | 74.2 | 61.7 | | | |

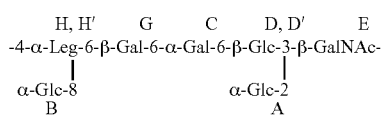

Figure 8:
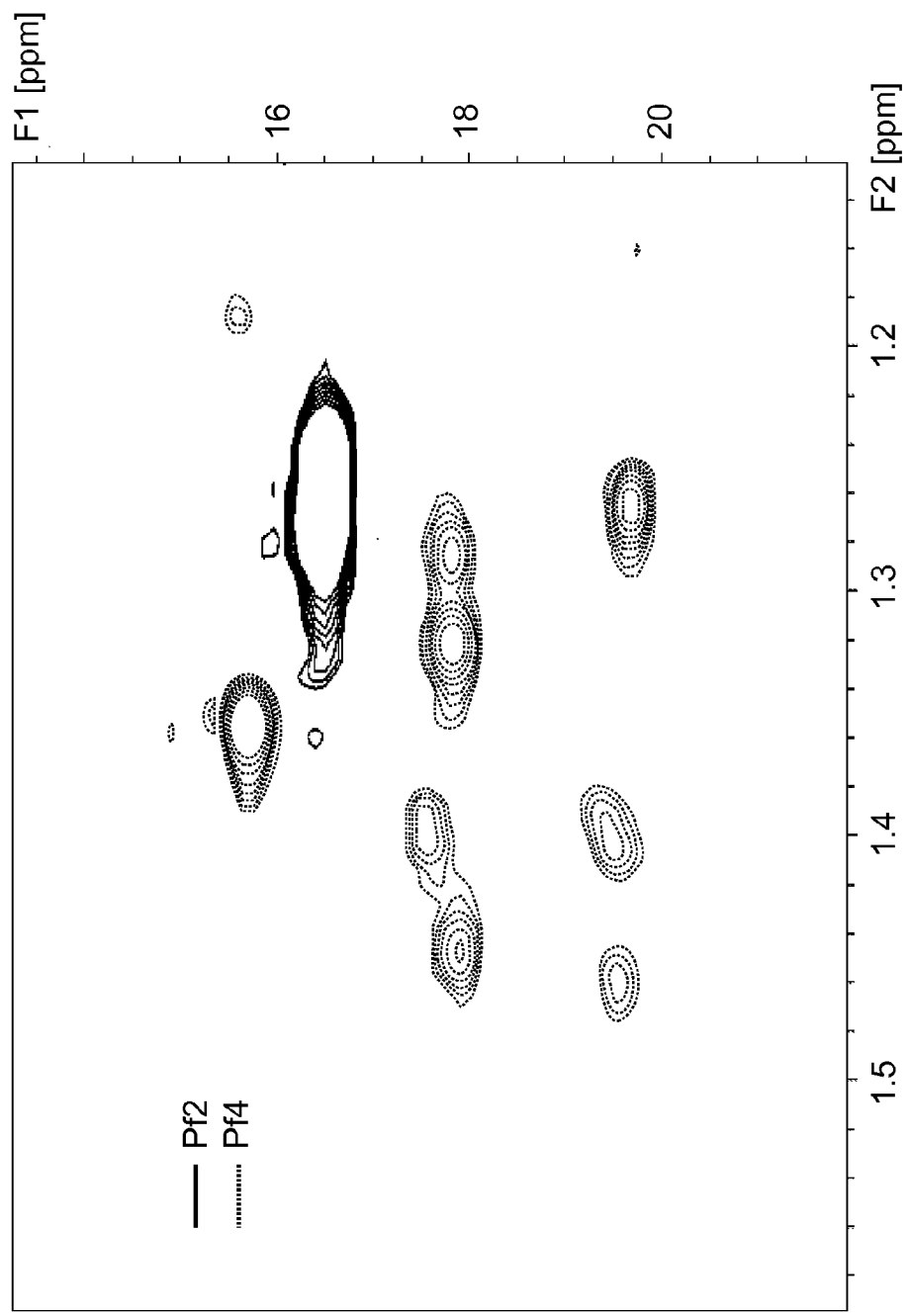
FIG. 8 shows a overlay of Pf2 (black solid lines) and Pf4 (black dotted lines) polysaccharides HSQC-methyl group spectra

To assess relative purity of the Pf4 compared with the Pf2 antigen the 2D-HSQC methyl group NMR spectra were compared. As no overlap between the spectra were detected we conclude that the samples are relatively free of antigen cross-contamination (FIG. 8).

Example 10: Analogous Polysaccharides (Pf11-Pf14) Identified from Strain E155 (Freiburg)

Figure 9:
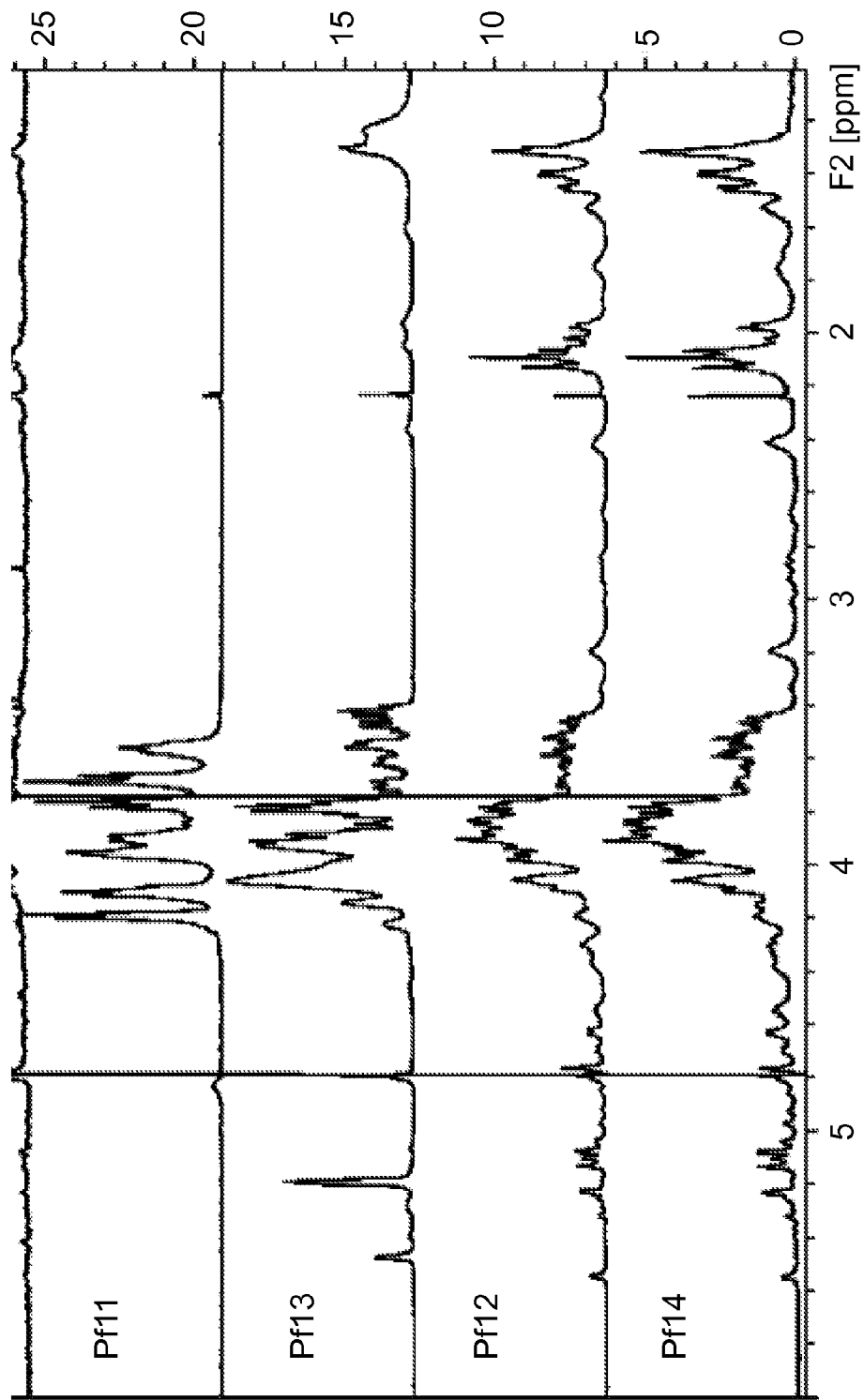
FIG. 9 shows a NMR spectra of E155 (Freiburg) strain polysaccharides Pf11-14.

The same purification scheme as described above for the TX0016(DO) strain was used to isolate polysaccharides from a second *E. faecium* clinical strain known as E155 (Freiburg). Polysaccharides with NMR spectra identical to Pf1, Pf3 and Pf4 were identified and named Pf11, Pf13 and Pf14, respectively (FIG. 9). However, a polysaccharide similar to Pf2 was absent under the culture and isolation conditions used. Instead, a carbohydrate named Pf12, with similar SEC and AEC properties to Pf2 but with an NMR spectrum matching Pf4, was isolated. As Pf12 eluted earlier from SEC than Pf14.

A summary of yields of Pf1-Pf4 purified from TX0016 and E155 (Freiburg) strains is shown in Table 5. Structurally equivalent polysaccharides Pf4 (TX0016) and Pf12/Pf14 (E155 (Freiburg)) were recovered in higher yields than Pf1/Pf11 (levan), Pf2 and Pf3/Pf13 (LTA) antigens.

TABLE 4

Antigen Yields

| *E. faecium* TX0016 (DO) | | *E. faecium* E155 (Freiburg) | |
|---|---|---|---|
| Antigen | Yield (mg/g)* | Antigen | Yield (mg/g)* |
| Pf1 | 1.9 | Pf11 | 22.4 |
| Pf2 | 20.2 | Pf12 | 27.7 |
| Pf3 | 1.7 | Pf13 | 10.1 |
| Pf4 | 73.6 | Pf14 | 59.7 |

*mg pure compound recovered/g crude polysaccharide starting material

Example 11: Preparation of Antigen CRM₁₉₇ Conjugates

CRM$_{197}$ carrier protein conjugates of Pf1, Pf2 and Pf4 were prepared using a cyanylation procedure and the 1-cyano-4-dimethylamino-pyridinium tetrafluoroborate (CDAP) reagent. CDAP introduces a cyanate group to carbohydrate hydroxyl groups which may form a covalent bond with protein carrier amino groups. PS antigen (5 mg in 1 ml water) was combined with CDAP (50 μl 100 mg/ml in acetonitrile) at RT and mixed for 30 s. Fifty μl of 0.2M TEA was added and reaction mixed gently for 2 min. An equal volume of CRM$_{197}$ (5 mg/ml in HEPES buffer) was introduced and the mixture stirred for 16 h at RT. The reaction mixture was transferred to a 100 kDa MWCO spin dialysis tube and washed 3× in 0.9% NaCl. The final 2 ml volume was applied to a SEC column to remove free carrier protein and to enrich for conjugated polysaccharide relative to the unconjugated free polysaccharide subpopulation. Fractions corresponding to the conjugate, which eluted earlier than the free polysaccharide, were pooled and the carbohydrate and peptide content quantified.

Example 12: Preparation of Antisera

Polyclonal whole cell antisera raised against TX0016 (DO) strain was prepared by injecting rabbits subcutaneously with 1×10⁸ heat-killed bacteria and 100 μg ISCOMATRIX™ adjuvant (CSL) at weeks 0, 4 and 6. Cells were killed by heating at 65° C. for 45 min. Rabbit were bled at week 8, and all three animals showed strong responses in whole cell ELISA assays. (data not shown) (See FIG. 12 for ELISA titers against the purified antigen).

To raise antisera specific for purified carbohydrate, groups of 3-4 rabbits were injected IM with 25 μg of conjugated polysaccharide and 100 μg ISCOMATRIX™ at weeks 0, 6 and 8. Rabbits were bled at week 10 and ELISA titers against purified antigen determined (see FIG. 12). The vaccination schedule for the un-conjugated Pf3 LTA antigen involved subcutaneous injections of 100 μg with 100 μg ISCOMATRIX at week 0 and week 1, followed by thrice weekly IV injections of 10 □μg (minus adjuvant) at weeks 2-4. Rabbits were bled at week 5 and ELISA titers against the purified antigens determined. For Pf1, Pf2 and Pf4 ELISAs 5 μg/ml antigen was applied in pH10.0 bicarbonate coating buffer to high binding microtiter plates and probed with serially diluted sera from animals sampled at day 0 and at the post-vaccination test bleed timepoint. For ELISAs measuring Pf3 LTA serum titers, 1 μg/ml antigen was combined with 1 μg/ml methylated human serum albumin for microplate coating to improve binding. ELISAs were developed using an HRP-detection kit from KPL.

For antisera raised against the Pf1 and Pf2 conjugates, all four rabbits responded with half maximal binding activity observed at serum dilutions in the range of 1:500-1:1000.

For the CRM$_{197}$-Pf4 antisera, all three vaccinated rabbits responded, with half maximal binding activity observed at serum dilutions in the range of 1:3000-1:10,000. The activity of the Pf3 LTA antisera was noticeably lower than the antisera elicited against the carbohydrate conjugates, with all four rabbits showing half maximal serum titers in the 1:100-1:500 dilution range. By way of comparison, the maximal non-specific ELISA binding activity of the matched pre-immune sera was negligible, less than 5% of the activity of the immune sera at dilutions of greater than 1:100.

Example 13: Flow Cytometry

The rabbit antisera and matched pre-bleed control sera were used as primary antibodies for flow cytometry detection. Overnight bacterial cultures were washed in 1×PBS and killed by heating (45 min 65° C.). Cells were then blocked with 2% BSA/PBS for 1 h RT. After washing in PBS cells were resuspended in 2% BSA in PBS with primary rabbit antibody and incubated for 1 h at RT. After washing, this was followed by secondary labeling with a phycoerythrin conjugated donkey anti-rabbit IgG (Jackson Immunoresearch, PA). The bacterial cells were fixed with 1% paraformaldehyde and analyzed with an Accuri C6 flow cytometer (BD Bioscience, CA). The mean fluorescence intensity (MFI) of the PE channel was determined for each sample (counting 20,000 events).

Figure 10:
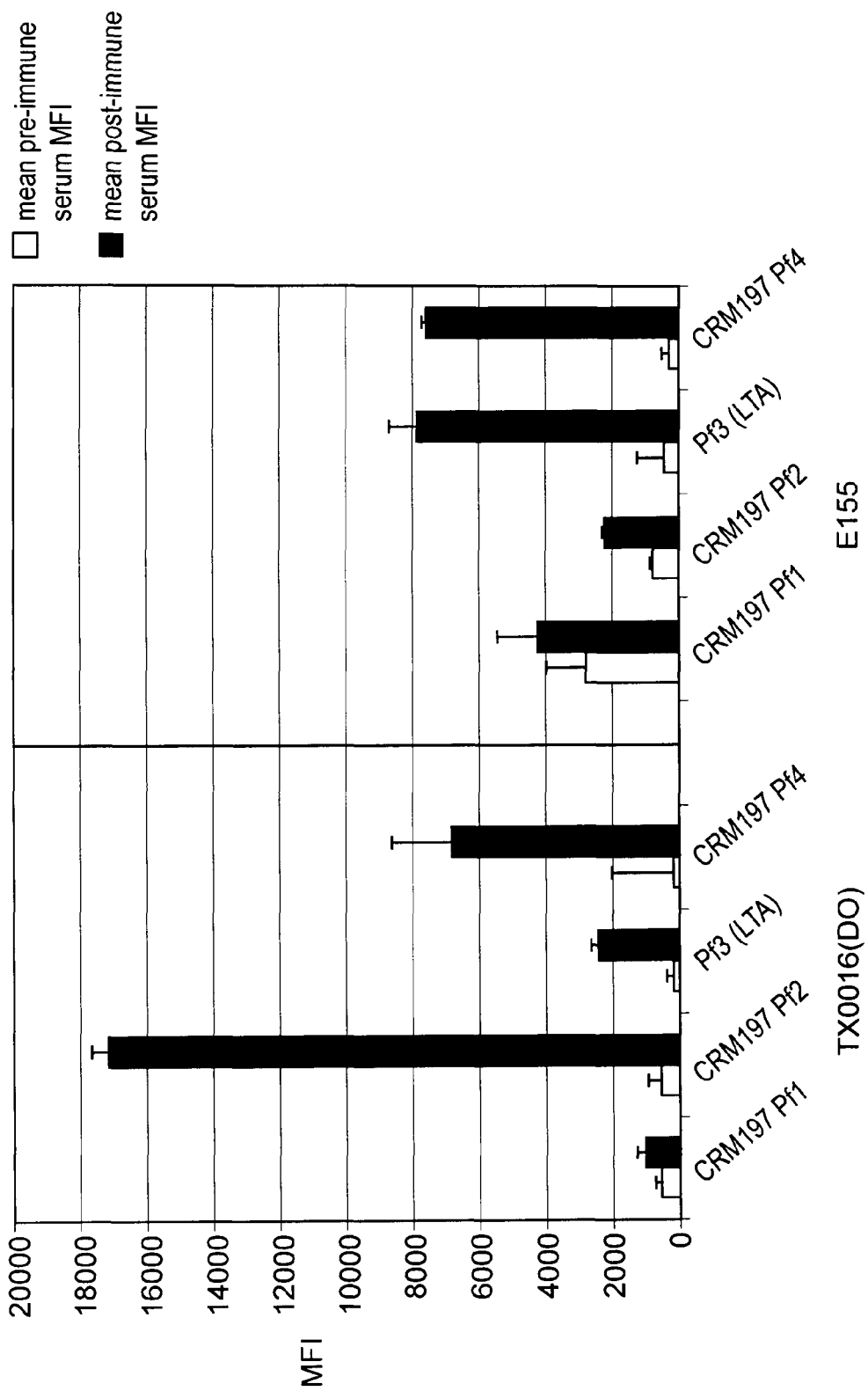
FIG. 10, Panel A shows a flow cytometry analysis of Pf1-Pf4 polysaccharides expressed on *E. faecium* strains TX0016(DO) and FIG. 10, Panel B shows a flow cytometry analysis of Pf1-Pf4 polysaccharides expressed on *E. faecium* E0155 (Freiburg). Solid white bars represent mean pre-immune serum MFI. Solid black bars represent mean post-immune serum MFI.
Figure 12B:
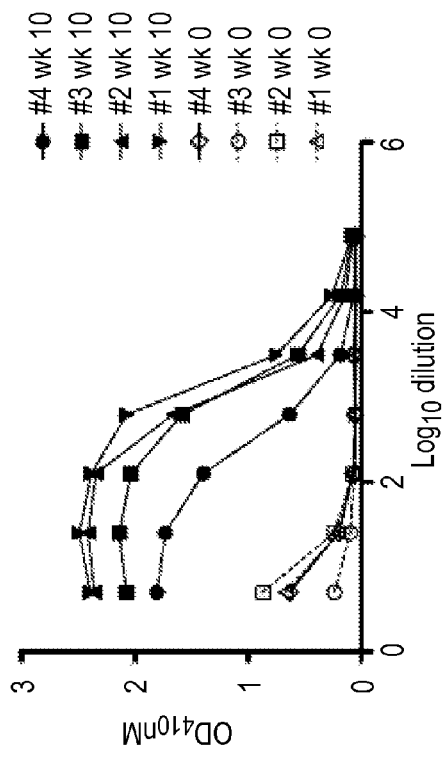
FIG. 12 shows ELISA screening of rabbit sera against a Pf1-CRM$_{197}$ conjugate, Pf2-CRM$_{197}$ conjugate, Pf4-CRM$_{197}$ conjugate, and Pf3 (LTA). Panel A shows Pf1-CRM$_{197}$ antisera versus Pf1 antigen. Panel B shows Pf2-CRM$_{197}$ antisera versus Pf2 antigen. Panel C shows Pf3 (LTA) antisera versus Pf3 antigen. Panel D shows Pf4-CRM$_{197}$ antisera versus Pf4 antigen.
Figure 12D:
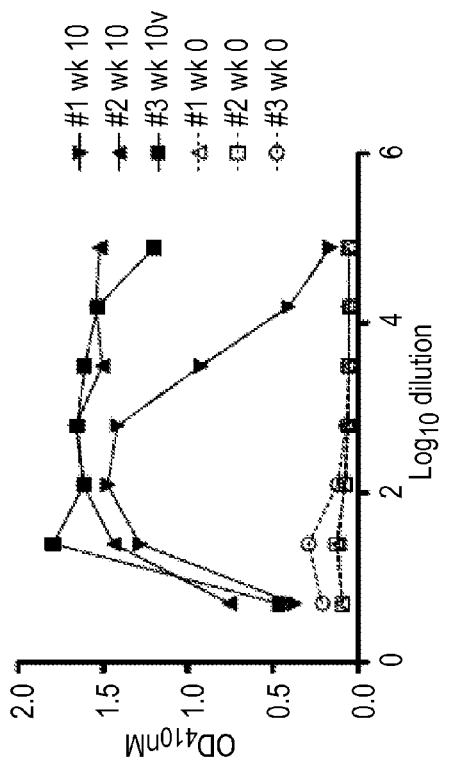
Figure 12A:
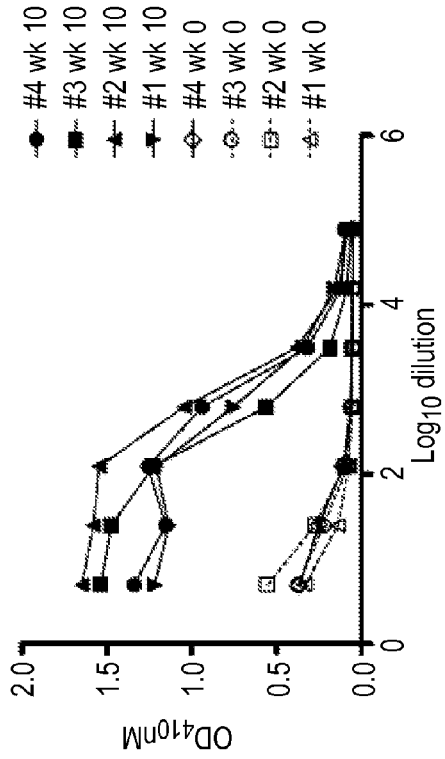
Figure 12C:
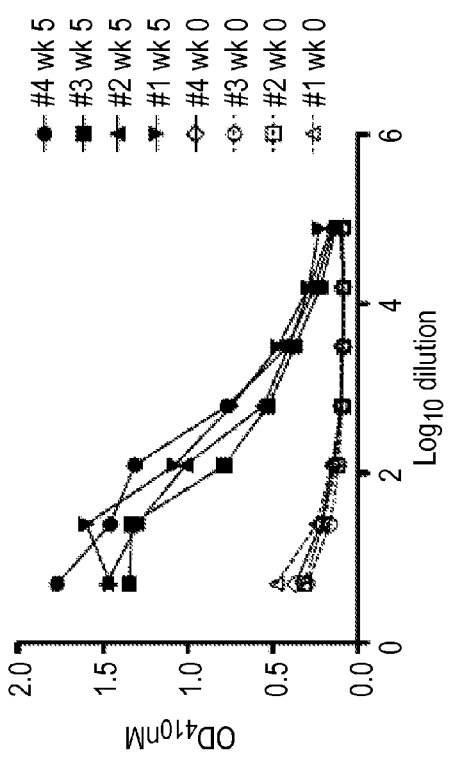

Flow cytometric analysis of *E. faecium* strains TX0016 and E155 (Freiburg) probed with Pf1-Pf4 antisera is shown in FIG. 10. The surface staining of antigens detected by specific sera are compared with matched pre-immune serum controls (1:500 dilution for serum raised against conjugates; 1:400 dilution for the Pf3 LTA serum). The Pf1 polysaccharide was not expressed at significant levels on the surface of TX0016, the strain from which the antigen was purified, under in vivo growth conditions. Low level Pf1 activity detected on the E155 (Freiburg) strain surface was not significantly different from that detected with the matched pre-immune control. High levels of Pf2 antigen were detected on TX0016 (DO), but not on strain E155 (Freiburg). Substantial levels of polysaccharides equivalent to Pf3 and Pf4 (Pf13 and Pf12/14, respectively) were detected on strain E155 (Freiburg).

Figure 13:
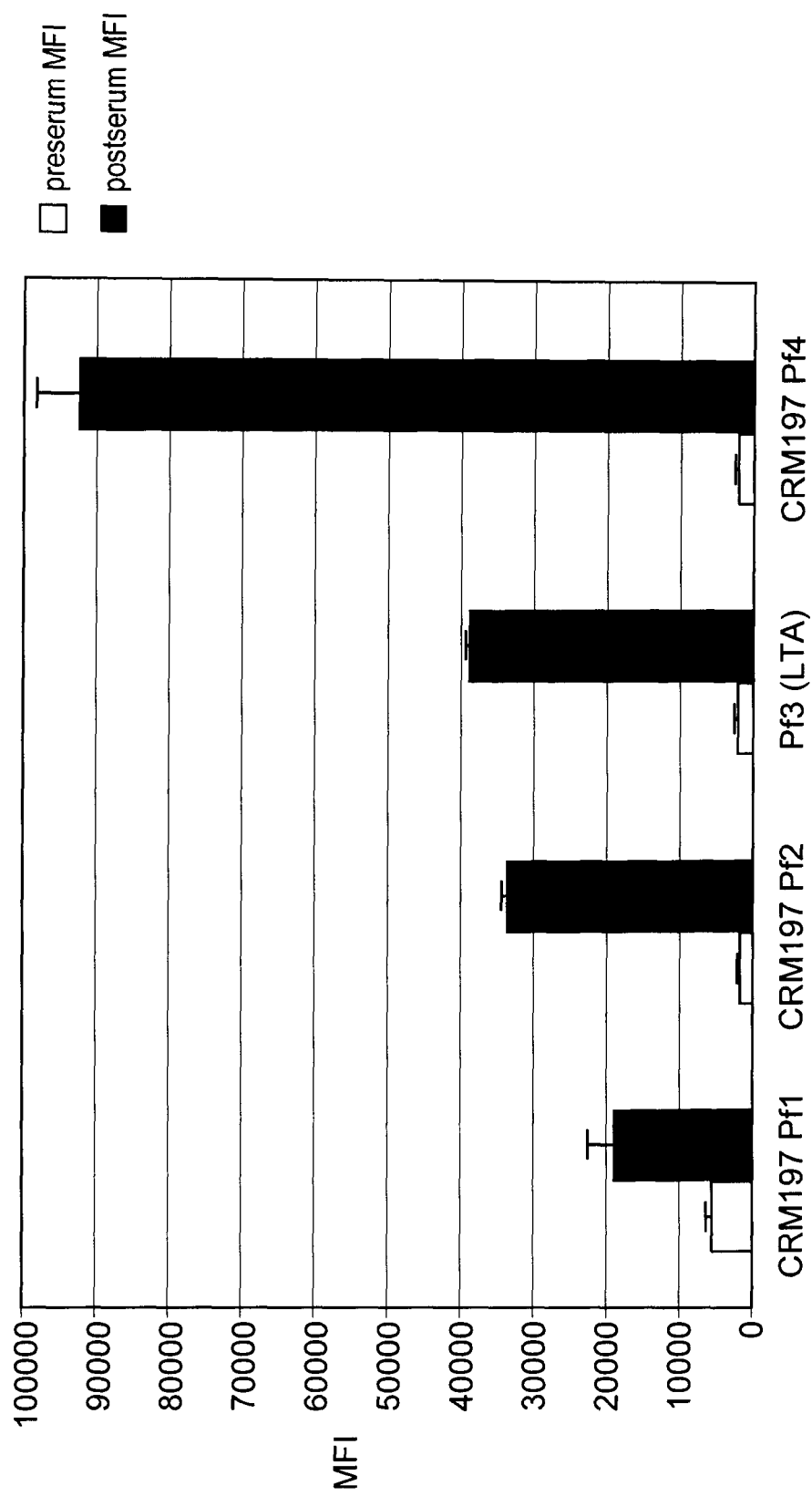
FIG. 13 shows a flow cytometry analysis of Pf1-Pf4 polysaccharides expressed on *E. faecium* 1,231,502.

Flow cytometric analysis of additional *E. faecium* strains probed with Pf1-Pf4 antisera is shown in Table 5 below. Moreover, FIG. 13 shows a flow cytometry analysis of Pf1-Pf4 polysaccharides expressed on *E. faecium* 1,231,502.

TABLE 5

| | | *E. faecium* PS antigen | | | |
|---|---|---|---|---|---|
| Strain | Epidemiology | Pf1 | Pf2 | Pf3 | Pf4 |
| E1162 | BSI | – | – | + | – |
| E1636 | BSI | – | – | + | – |
| E1679 | catheter | – | – | ++ | – |
| U0317 | UTI | – | + | ++ | + |
| E0155 (Freiburg) | Unknown Epidemiology; may or may not be epidemic, VRE endocarditis | – | – | +++ | +++ |
| TX0016 | | – | +++ | ++ | +++ |
| 1,230,933 | wound | – | + | +++ | ++ |
| 1,231,408 | BSI | – | – | +++ | – |
| 1,141,733 | Unknown. | – | – | – | – |
| 1,231,410 | Unknown. | – | + | +++ | ++ |
| 1,231,501 | Unknown. | – | – | + | – |
| 1,231,502 | Unknown. | – | ++ | +++ | +++ |
| E0980 | Fecal, healthy v. | – | +++ | + | +++ |
| E1039 | Fecal, healthy v. | – | – | ++ | – |
| E1071 | Fecal, hospital patient | – | – | +++ | + |
| Com12 | Fecal, healthy v. | – | – | + | – |
| Com15 | Fecal, healthy v. | – | – | – | – |
| TX1330 | Fecal, healthy v. | – | – | + | – |

MFI Ratio of Post/Pre-Bleed:
1 to 4.9X –
5 to 9.9X +
10 to 14.9X ++
>15X +++

Example 14: HL-60 Opsonophagocytic Assays

Pre-frozen bacterial stocks of *E. faecium* TX0016(DO) and E155 (Freiburg) were prepared from the same fermentation from which the Pf1-Pf4 antigens were purified. Cells were pelleted and suspended to concentration of 1 OD$_{600}$ unit per ml in DPBS 20% glycerol and frozen. Thawed cells were diluted to 1×10$^5$ CFU/ml in OPA buffer (Hanks Balanced Salt Solution, 0.1% gelatin, 1 mM MgCl$_2$, 2.5 mM CaCl$_2$) and 10 μl (10$^3$ CFU) opsonized with 10 μl of serially diluted sera for 1 h at 4° C. in a U-bottomed tissue culture microplate. Subsequently, 10 μl of complement (Baby Rabbit Serum, Pel-Freez) and 20 μl of HL-60 cells (0.5×10$^7$/ml) were added and the mixture shaken at 300 rpm for 1 h at 37° C. in a 5% CO$_2$ incubator. Ten μl of each 50 μl reaction was transferred into the corresponding wells of a prewetted Millipore MultiScreenHTS HV filter plate containing 200 μl water. After vacuum filtering the liquid, 150 μl of Columbia broth (with 2% glucose) was applied and filtered and plate incubated overnight at 37° C. The next day the colonies were enumerated after staining with Coomassie dye using an ImmunoSpot® analyzer and ImmunoCapture software. To establish the specificity of any detectable OPA activity, immune sera were preincubated with 20 μg/ml purified antigen prior to the opsonization step. The OPA assay include control reactions without neutrophil-like HL60s or complement, to demonstrate dependence of any observed killing on these components.

Antisera raised against heat-killed TX0016(DO) failed to show bactericidal activity in OPA assays. In contrast, antigen-specific opsonic activity was detected for the Pf2, Pf3 and Pf4 antisera FIG. 11. The Pf2-specific antisera showed activity against the TX0016 (DO) strain but not the E155 (Freiburg) strain, which does not produce the Pf2 polysaccharide under the fermentation conditions used. The Pf3 and Pf4 antisera showed activity against E155 (Freiburg) strain but not TX0016, despite presence of these antigens on the bacterial surface. The Pf1 antisera was not able to kill these strains under the OPA conditions tested. Antigen-specific opsonic activity was also detected by the opsonophagocytic assay for the Pf2, Pf3 and Pf4 antisera against additional *E. faecium* strains. See Table 6 below, wherein observed OPA activity is represented by an asterisk superimposed over relative expression levels determined by flow cytometry (same as in Table 5).

Figure 14A:
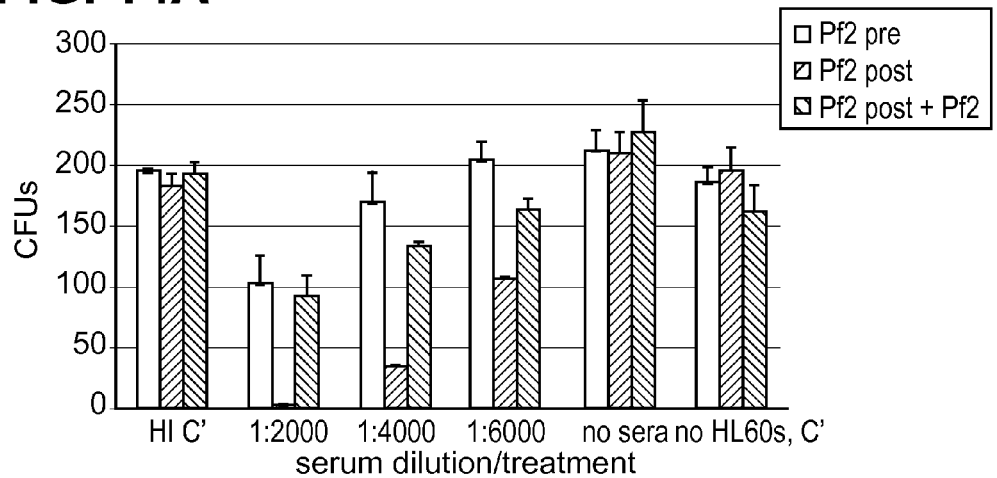
FIG. 14 shows opsonophagocytic activity of antisera induced by *E. faecium* Pf2- and Pf4-CRM$_{197}$ conjugates against strain 1,231,502 (502). Panel A of FIG. 14 shows that OPA activity of Pf2 sera versus strain '502 is reversed by 20 µg/ml Pf2. Panel B and Panel C of FIG. 14 shows that OPA activity of Pf4 sera versus strain '502 is reversed by 20 µg/ml Pf4. Panel B includes a typographical error in the last box of the legend, which should have indicated "Pf4 post+Pf4" instead of "Pf4 post+Pf2." Panel C of FIG. 14 is identical to Panel B of FIG. 14 but includes the corrected legend. "HI C" in Panel A, Panel B, and Panel C of FIG. 14 refers to heat-inactivated complement.
Figure 14B:
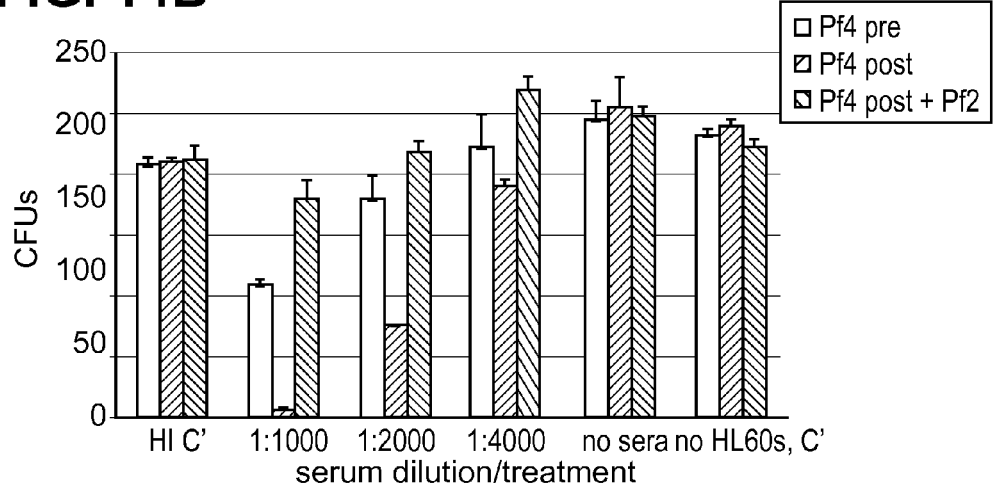
Figure 14C:
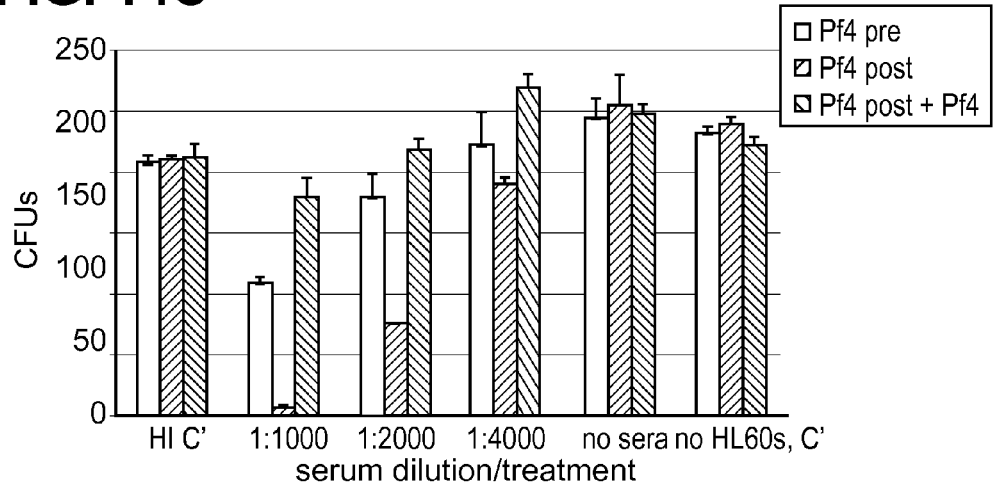

Moreover, FIG. 14 shows opsonophagocytic activity of antisera induced by *E. faecium* Pf2 and Pf4 antigens. More specifically, FIG. 14 indicates activity of *E. faecium* polysaccharide-conjugates, Pf2-CRM$_{197}$ and Pf4-CRM$_{197}$ conjugates, against strain 1,231,502 ('502). Panel A of FIG. 14 shows that OPA activity of Pf2 sera versus strain '502 is reversed by 20 μg/ml Pf2. Panel B and Panel C of FIG. 14 show that OPA activity of Pf4 sera versus strain '502 is reversed by 20 μg/ml Pf4. Panel B includes a typographical error in the last box of the legend, which should have indicated "Pf4 post+Pf4" instead of "Pf4 post+Pf2." Panel C of FIG. 14 is identical to Panel B of FIG. 14 but includes the corrected legend. "HI C'" in Panel A, Panel B, and Panel C of FIG. 14 refers to heat-inactivated complement.

TABLE 6

| | | E. faecium PS antigen | | | |
|---|---|---|---|---|---|
| Strain | Epidemiology | Pf1 | Pf2 | Pf3 | Pf4 |
| E0980 | community | − | +++* | + | +++* |
| E1039 | community | − | − | ++ | − |
| E1071 | community | − | − | +++ | + |
| Com12 | community | − | − | + | − |
| Com15 | community | − | − | − | − |
| TX1330 | community | − | − | + | − |
| E1162 | clinical | − | − | + | − |
| E1636 | clinical | − | − | + | − |
| E1679 | clinical, VRE | − | − | ++ | − |
| U0317 | clinical | − | + | ++ | + |
| E0155 (Freiburg) | Unknown epidemiology; may or may not be epidemic, VRE | − | − | +++* | +++* |
| TX0016 | clinical | − | +++* | ++ | +++ |
| 1,230,933 | clinical | − | +* | +++ | ++* |
| 1,231,408 | clinical | − | − | +++ | − |
| 1,141,733 | clinical | − | − | − | − |
| 1,231,410 | clinical | − | +* | +++ | ++* |
| 1,231,501 | clinical | − | − | + | − |
| 1,231,502 | clinical | − | ++* | +++ | +++* |

Example 15: Preparation of an Antibody that Binds to a Saccharide Herein

The present example illustrates preparation of a monoclonal antibody that can specifically bind to a saccharide described herein, such as to polysaccharides Pf1, Pf2, Pf3, Pf4, and/or immunoconjugates, and/or immunogenic compositions thereof.

Techniques for producing monoclonal antibodies are known in the art. Immunogens that may be employed include a purified saccharide described herein, an immunoconjugate containing a saccharide described herein, and cells expressing a saccharide described herein on the cell surface. Selection of the immunogen can be made by the skilled artisan without undue experimentation.

Mice, such as Balb/c, are immunized with the immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-saccharide antibodies.

After a suitable antibody titer has been detected, the animals "positive" for antibodies can be injected with a final intravenous injection of the immunogen. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the saccharide. Determination of "positive" hybridoma cells secreting the desired monoclonal antibodies against the saccharide is within the skill in the art.

The positive hybridoma cells can be injected intraperitoneally into syngeneic Balb/c mice to produce ascites containing the anti-saccharide monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Aspects of the Invention

The following clauses describe additional embodiments of the invention:

C1. An isolated polysaccharide comprising a legionaminic acid moiety, a N-acetylgalactosamine moiety, a galactose moiety, and a glucose moiety.

C2. The polysaccharide of clause C1, wherein the legionaminic acid moiety is linked to the glucose moiety.

C3. The polysaccharide of clause C1, wherein the legionaminic acid moiety is linked to the galactose moiety.

C4. The polysaccharide of clause C1, wherein the legionaminic acid moiety is linked to the N-acetylgalactosamine moiety.

C5. The polysaccharide of clause C1, wherein the legionaminic acid moiety, N-acetylgalactosamine moiety, galactose moiety, and glucose moiety are in a molar ratio of 1:1:2:3.

C6. The polysaccharide of clause C1, wherein the polysaccharide comprises a repeating unit of a structure represented by:

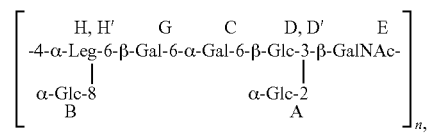

wherein Leg is a legionaminic acid moiety, Gal is a galactose moiety, Glc is a glucose moiety, and GalNAc is a N-acetylgalactosamine moiety, and wherein n is an integer from 1 to 1000.

C7. The polysaccharide of clause C6, wherein n is between about 40 and about 60.

C8. The polysaccharide of clause C1, wherein the molecular weight of the polysaccharide is between about 60 kDa and about 100 kDa.

C9. The polysaccharide of clause C1, wherein the polysaccharide has an NMR spectrum as shown in FIG. 7.

C10. The polysaccharide of clause C1, wherein the polysaccharide is branched.

C11. The polysaccharide of clause C1, wherein the polysaccharide is a Gram-positive coccal polysaccharide.

C12. The polysaccharide of clause C11, wherein the polysaccharide is an *Enterococcus* polysaccharide.

C13. The polysaccharide of clause C12, wherein the polysaccharide is an *Enterococcus faecium* polysaccharide.

C14. The polysaccharide of clause C13, wherein the polysaccharide is an *Enterococcus faecium* TX0016 (DO; E1794) polysaccharide.

C15. The polysaccharide of clause C13, wherein the polysaccharide is an *Enterococcus faecium* E0155 polysaccharide.

C16. The polysaccharide of clause C1, wherein the polysaccharide is a cell surface polysaccharide.

C17. The polysaccharide of clause C1, wherein the polysaccharide is a capsular polysaccharide.

C18. The polysaccharide of clause C1, wherein the polysaccharide is immunogenic.

C19. The polysaccharide of clause C18, wherein the polysaccharide is capable of inducing an immune response with opsonic activity.

C20. The polysaccharide of clause C18, wherein the polysaccharide is capable of inducing a bactericidal immune response.

C21. A branched polysaccharide comprising a legionaminic acid moiety, a N-acetylgalactosamine moiety, a galactose moiety, and a glucose moiety.

C22. The polysaccharide of clause C21, wherein the legionaminic acid moiety is linked to the glucose moiety.

C23. The polysaccharide of clause C21, wherein the legionaminic acid moiety is linked to the galactose moiety.

C24. The polysaccharide of clause C21, wherein the legionaminic acid moiety is linked to the N-acetylgalactosamine moiety.

C25. The polysaccharide of clause C21, wherein the legionaminic acid moiety, N-acetylgalactosamine moiety, galactose moiety, and glucose moiety are in a molar ratio of 1:1:2:3.

C26. The polysaccharide of clause C21, wherein the polysaccharide comprises a repeating unit of a structure represented by:

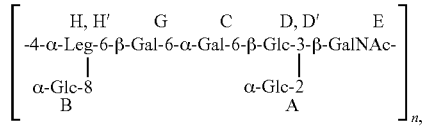

wherein Leg is a legionaminic acid moiety, Gal is a galactose moiety, Glc is a glucose moiety, and GalNAc is a N-acetylgalactosamine moiety, and wherein n is an integer from 1 to 1000.

C27. The polysaccharide of clause C22, wherein n is between about 40 and about 60.

C28. The polysaccharide of clause C21, wherein the molecular weight of the polysaccharide is between about 60 kDa and about 100 kDa.

C29. The polysaccharide of clause C21, wherein the polysaccharide has an NMR spectrum as shown in FIG. 7.

C30. The polysaccharide of clause C21, wherein the polysaccharide is a Gram-positive coccal polysaccharide.

C31. The polysaccharide of clause C30, wherein the polysaccharide is an *Enterococcus* polysaccharide.

C32. The polysaccharide of clause C31, wherein the polysaccharide is an *Enterococcus faecium* polysaccharide.

C33. The polysaccharide of clause C32, wherein the polysaccharide is an *Enterococcus faecium* TX0016 (DO; E1794) polysaccharide.

C34. The polysaccharide of clause C32, wherein the polysaccharide is an *Enterococcus faecium* E0155 polysaccharide.

C35. The polysaccharide of clause C21, wherein the polysaccharide is a cell surface polysaccharide.

C36. The polysaccharide of clause C21, wherein the polysaccharide is a capsular polysaccharide.

C37. The polysaccharide of clause C21, wherein the polysaccharide is immunogenic.

C38. The polysaccharide of clause C37, wherein the polysaccharide is capable of inducing an immune response with opsonic activity.

C39. The polysaccharide of clause C37, wherein the polysaccharide is capable of inducing a bactericidal immune response.

C40. The polysaccharide of clause C21, wherein the polysaccharide has been chemically synthesized.

C41. An immunogenic composition comprising an effective amount of a polysaccharide and a pharmaceutically acceptable diluent, wherein the polysaccharide comprises a legionaminic acid moiety, a N-acetylgalactosamine moiety, a galactose moiety, and a glucose moiety.

C42. The polysaccharide of clause C41, wherein the legionaminic acid moiety is linked to the glucose moiety.

C43. The polysaccharide of clause C41, wherein the legionaminic acid moiety is linked to the galactose moiety.

C44. The polysaccharide of clause C41, wherein the legionaminic acid moiety is linked to the N-acetylgalactosamine moiety.

C45. The composition of clause C41, wherein the legionaminic acid moiety, N-acetylgalactosamine moiety, galactose moiety, and glucose moiety are in a molar ratio of 1:1:2:3.

C46. The composition of clause C41, wherein the polysaccharide comprises a repeating unit of a structure represented by:

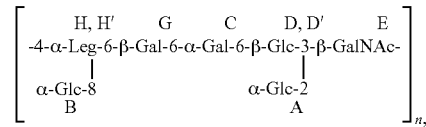

wherein Leg is a legionaminic acid moiety, Gal is a galactose moiety, Glc is a glucose moiety, and GalNAc is a N-acetylgalactosamine moiety, and wherein n is an integer from 1 to 1000.

C47. The composition of clause C42, wherein n is between about 40 and about 60.

C48. The composition of clause C41, wherein the molecular weight of the polysaccharide is between about 60 kDa and about 100 kDa.

C49. The composition of clause C41, wherein the polysaccharide has an NMR spectrum as shown in FIG. 7.

C50. The composition of clause C41, wherein the polysaccharide is branched.

C51. The composition of clause C41, wherein the polysaccharide is a Gram-positive coccal polysaccharide.

C52. The composition of clause C51, wherein the polysaccharide is an *Enterococcus* polysaccharide.

C53. The composition of clause C52, wherein the polysaccharide is an *Enterococcus faecium* polysaccharide.

C54. The composition of clause C53, wherein the polysaccharide is an *Enterococcus faecium* TX0016 (DO; E1794) polysaccharide.

C55. The composition of clause C53, wherein the polysaccharide is an *Enterococcus faecium* E0155 polysaccharide.

C56. The composition of clause C41, wherein the polysaccharide is a cell surface polysaccharide.
C57. The composition of clause C41, wherein the polysaccharide is a capsular polysaccharide.
C58. The composition of clause C41, wherein the polysaccharide has been chemically synthesized.
C59. The composition of clause C41, wherein the polysaccharide is conjugated to a carrier protein.
C60. The composition of clause C59, wherein the carrier protein is a protein selected from the group consisting of of a diphtheria toxoid, CRM197, a tetanus toxoid, a cholera toxoid, a pertussis toxoid, an *E. coli* heat labile toxoid (LT), a pneumolysin toxoid, pneumococcal surface protein A (PspA), pneumococcal adhesin protein A (PsaA), a C5a peptidase from *Streptococcus, Haemophilus influenzae* protein D, ovalbumin, keyhole limpet haemocyanin (KLH), bovine serum albumin (BSA), purified protein derivative of tuberculin (PPD), and a *Pseudomonas* exotoxin, or its derivatives.
C61. The composition of clause C60, wherein the carrier protein is $CRM_{197}$.
C62. An isolated polysaccharide comprising an altruronic acid moiety, a fucose moiety, and a glucose moiety.
C63. The polysaccharide of clause C62, wherein the altruronic acid moiety is linked to the fucose moiety.
C64. The polysaccharide of clause C62, wherein the fucose moiety is linked to a glucose moiety.
C65. The polysaccharide of clause C62, wherein the altruronic acid moiety, fucose moiety, and glucose moiety are in a molar ratio of 1:4:2.
C66. The polysaccharide of clause C62, wherein the polysaccharide comprises a repeating unit of a structure represented by:

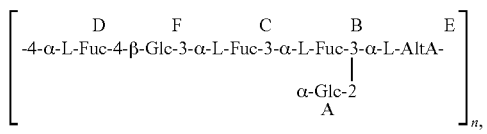

wherein Fuc is a fucose moiety, Glc is a glucose moiety, and AltA is an altruronic acid moiety, and wherein n is an integer from 1 to 1000.
C67. The polysaccharide of clause C63, wherein n is between about 280 and about 300.
C68. The polysaccharide of clause C62, wherein the molecular weight of the polysaccharide is between about 250 kDa and about 350 kDa.
C69. The polysaccharide of clause C62, wherein the polysaccharide has an NMR spectrum as shown in FIG. 2.
C70. The polysaccharide of clause C62, wherein the polysaccharide is branched.
C71. The polysaccharide of clause C62, wherein the polysaccharide is a Gram-positive coccal polysaccharide.
C72. The polysaccharide of clause C71, wherein the polysaccharide is an *Enterococcus* polysaccharide.
C73. The polysaccharide of clause C72, wherein the polysaccharide is an *Enterococcus faecium* polysaccharide.
C74. The polysaccharide of clause C73, wherein the polysaccharide is an *Enterococcus faecium* TX0016 (DO; E1794) polysaccharide.
C75. The polysaccharide of clause C73, wherein the polysaccharide is an *Enterococcus faecium* E0155 polysaccharide.
C76. The polysaccharide of clause C62, wherein the polysaccharide is a cell surface polysaccharide.
C77. The polysaccharide of clause C62, wherein the polysaccharide is a capsular polysaccharide.
C78. The polysaccharide of clause C62, wherein the polysaccharide is immunogenic.
C79. The polysaccharide of clause C78, wherein the polysaccharide is capable of inducing an immune response with opsonic activity.
C80. The polysaccharide of clause C78, wherein the polysaccharide is capable of inducing a bactericidal immune response.
C81. A branched polysaccharide comprising an altruronic acid moiety, a fucose moiety, and a glucose moiety.
C82. The polysaccharide of clause C81, wherein the altruronic acid moiety is linked to the fucose moiety.
C83. The polysaccharide of clause C81, wherein the fucose moiety is linked to a glucose moiety.
C84. The polysaccharide of clause C81, wherein the altruronic acid moiety, fucose moiety, and glucose moiety are in a molar ratio of 1:4:2.
C85. The polysaccharide of clause C81, wherein the polysaccharide comprises a repeating unit of a structure represented by:

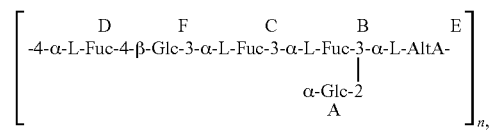

wherein Fuc is a fucose moiety, Glc is a glucose moiety, and AltA is an altruronic acid moiety, and wherein n is an integer from 1 to 1000.
C86. The polysaccharide of clause C85, wherein n is between about 280 and about 300.
C87. The polysaccharide of clause C81, wherein the molecular weight of the polysaccharide is between about 250 kDa and about 350 kDa.
C88. The polysaccharide of clause C81, wherein the polysaccharide has an NMR spectrum as shown in FIG. 2.
C89. The polysaccharide of clause C81, wherein the polysaccharide is a Gram-positive coccal polysaccharide.
C90. The polysaccharide of clause C89, wherein the polysaccharide is an *Enterococcus* polysaccharide.
C91. The polysaccharide of clause C90, wherein the polysaccharide is an *Enterococcus faecium* polysaccharide.
C92. The polysaccharide of clause C91, wherein the polysaccharide is an *Enterococcus faecium* TX0016 (DO; E1794) polysaccharide.
C93. The polysaccharide of clause C91, wherein the polysaccharide is an *Enterococcus faecium* E0155 polysaccharide.
C94. The polysaccharide of clause C81, wherein the polysaccharide is a cell surface polysaccharide.
C95. The polysaccharide of clause C81, wherein the polysaccharide is a capsular polysaccharide.
C96. The polysaccharide of clause C81, wherein the polysaccharide is immunogenic.
C97. The polysaccharide of clause C96, wherein the polysaccharide is capable of inducing an immune response with opsonic activity.
C98. The polysaccharide of clause C96, wherein the polysaccharide is capable of inducing a bactericidal immune response.

C99. The polysaccharide of clause C81, wherein the polysaccharide has been chemically synthesized.

C100. An immunogenic composition comprising an effective amount of a polysaccharide and a pharmaceutically acceptable diluent, wherein the polysaccharide comprises an altruronic acid moiety, a fucose moiety, and a glucose moiety.

C101. The composition of clause C100, wherein the altruronic acid moiety is linked to the fucose moiety.

C102. The composition of clause C100, wherein the fucose moiety is linked to a glucose moiety.

C103. The composition of clause C100, wherein the altruronic acid moiety, fucose moiety, and glucose moiety are in a molar ratio of 1:4:2.

C104. The composition of clause C100, wherein the polysaccharide comprises a repeating unit of a structure represented by:

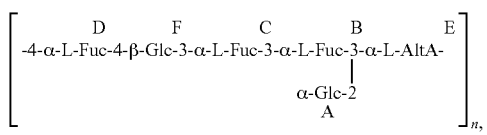

wherein Fuc is a fucose moiety, Glc is a glucose moiety, and AltA is an altruronic acid moiety, and wherein n is an integer from 1 to 1000.

C105. The composition of clause C104, wherein n is between about 280 and about 300.

C106. The composition of clause C100, wherein the molecular weight of the polysaccharide is between about 250 kDa and about 350 kDa.

C107. The composition of clause C100, wherein the polysaccharide has an NMR spectrum as shown in FIG. 2.

C108. The composition of clause C100, wherein the polysaccharide is branched.

C109. The composition of clause C100, wherein the polysaccharide is a Gram-positive coccal polysaccharide.

C110. The composition of clause C109, wherein the polysaccharide is an *Enterococcus* polysaccharide.

C111. The composition of clause C110, wherein the polysaccharide is an *Enterococcus faecium* polysaccharide.

C112. The composition of clause C111, wherein the polysaccharide is an *Enterococcus faecium* TX0016 (DO; E1794) polysaccharide.

C113. The composition of clause C111, wherein the polysaccharide is an *Enterococcus faecium* E0155 polysaccharide.

C114. The composition of clause C100, wherein the polysaccharide is a cell surface polysaccharide.

C115. The composition of clause C100, wherein the polysaccharide is a capsular polysaccharide.

C116. The composition of clause C100, wherein the polysaccharide has been chemically synthesized.

C117. The composition of clause C100, wherein the polysaccharide is conjugated to a carrier protein.

C118. The composition of clause C117, wherein the carrier protein is a protein selected from the group consisting of of a diphtheria toxoid, CRM197, a tetanus toxoid, a cholera toxoid, a pertussis toxoid, an *E. coli* heat labile toxoid (LT), a pneumolysin toxoid, pneumococcal surface protein A (PspA), pneumococcal adhesin protein A (PsaA), a C5a peptidase from *Streptococcus*, *Haemophilus influenzae* protein D, ovalbumin, keyhole limpet haemocyanin (KLH), bovine serum albumin (BSA), purified protein derivative of tuberculin (PPD), and a *Pseudomonas* exotoxin, or its derivatives.

C119. The composition of clause C118, wherein the carrier protein is $CRM_{197}$.

C120. An isolated polysaccharide comprising a repeating unit of a glycerol phosphate moiety and a glucose moiety, wherein the polysaccharide is an *Enterococcus faecium* TX0016 (DO; E1794) polysaccharide.

C121. An isolated polysaccharide comprising a repeating unit of a glycerol phosphate moiety and a glucose moiety, wherein the polysaccharide is an *Enterococcus faecium* E0155 polysaccharide.

C122. The polysaccharide of clause C120 or C121, wherein the repeating unit comprises a structure represented by:

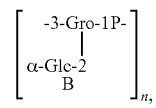

wherein Gro-1P is a glycerol phosphate moiety and Glc is a glucose moiety, and wherein n is an integer from 1 to 1000.

C123. The polysaccharide of clause C122, wherein n is between about 80 to about 100.

C124. The polysaccharide of clause C120 or C121, wherein the repeating unit comprises a structure represented by:

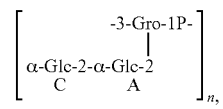

wherein Gro-1P is a glycerol phosphate moiety and Glc is a glucose moiety, and wherein n is an integer from 1 to 1000.

C125. The polysaccharide of clause C124, wherein n is between about 80 to about 100.

C126. The polysaccharide of clause C120 or C121, wherein the molecular weight of the polysaccharide is between about 10 kDa and 20 kDa.

C127. The polysaccharide of clause C120 or C121, wherein the polysaccharide has an NMR spectrum as shown in FIG. 6.

C128. The polysaccharide of clause C120 or C121, wherein the polysaccharide is a cell surface polysaccharide.

C129. The polysaccharide of clause C120 or C121, wherein the polysaccharide is a capsular polysaccharide.

C130. The polysaccharide of clause C120 or C121, wherein the polysaccharide is immunogenic.

C131. The polysaccharide of clause C130, wherein the polysaccharide is capable of inducing an immune response with opsonic activity.

C132. The polysaccharide of clause C130, wherein the polysaccharide is capable of inducing a bactericidal immune response.

C133. A branched polysaccharide comprising a repeating unit of a glycerol phosphate moiety and a glucose moiety, wherein the polysaccharide is an *Enterococcus faecium* TX0016 (DO; E1794) polysaccharide.

C134. A branched polysaccharide comprising a repeating unit of a glycerol phosphate moiety and a glucose moiety, wherein the polysaccharide is an *Enterococcus faecium* E0155 polysaccharide.

C135. The polysaccharide of clause C133 or C134, wherein the repeating unit comprises a structure represented by:

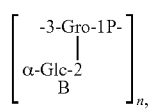

wherein Gro-1P is a glycerol phosphate moiety and Glc is a glucose moiety, and wherein n is an integer from 1 to 1000.

C136. The polysaccharide of clause C135, wherein n is between about 80 to about 100.

C137. The polysaccharide of clause C133 or C134, wherein the repeating unit comprises a structure represented by:

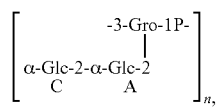

wherein Gro-1P is a glycerol phosphate moiety and Glc is a glucose moiety, and wherein n is an integer from 1 to 1000.

C138. The polysaccharide of clause C137, wherein n is between about 80 to about 100.

C139. The polysaccharide of clause C133 or C134, wherein the molecular weight of the polysaccharide is between about 10 kDa and 20 kDa.

C140. The polysaccharide of clause C133 or C134, wherein the polysaccharide has an NMR spectrum as shown in FIG. 6.

C141. The polysaccharide of clause C133 or C134, wherein the polysaccharide is a cell surface polysaccharide.

C142. The polysaccharide of clause C133 or C134, wherein the polysaccharide is a capsular polysaccharide.

C143. The polysaccharide of clause C133 or C134, wherein the polysaccharide is immunogenic.

C144. The polysaccharide of clause C143, wherein the polysaccharide is capable of inducing an immune response with opsonic activity.

C145. The polysaccharide of clause C143, wherein the polysaccharide is capable of inducing a bactericidal immune response.

C146. The polysaccharide of clause C133 or C134, wherein the polysaccharide has been chemically synthesized.

C147. An immunogenic composition comprising an effective amount of a polysaccharide and a pharmaceutically acceptable diluent, wherein the polysaccharide comprises a repeating unit of a glycerol phosphate moiety and a glucose moiety, wherein the polysaccharide is an *Enterococcus faecium* TX0016 (DO; E1794) polysaccharide.

C148. An immunogenic composition comprising an effective amount of a polysaccharide and a pharmaceutically acceptable diluent, wherein the polysaccharide comprises a repeating unit of a glycerol phosphate moiety and a glucose moiety, wherein the polysaccharide is an *Enterococcus faecium* E0155 polysaccharide.

C149. The composition of clause C147 or C148, wherein the repeating unit comprises a structure represented by:

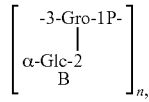

wherein Gro-1P is a glycerol phosphate moiety and Glc is a glucose moiety, and wherein n is an integer from 1 to 1000.

C150. The composition of clause C149, wherein n is between about 80 to about 100.

C151. The composition of clause C147 or C148, wherein the repeating unit comprises a structure represented by:

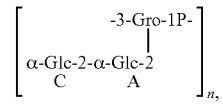

wherein Gro-1P is a glycerol phosphate moiety and Glc is a glucose moiety, and wherein n is an integer from 1 to 1000.

C152. The composition of clause C151, wherein n is between about 80 to about 100.

C153. The composition of clause C147 or C148, wherein the molecular weight of the polysaccharide is between about 10 kDa and 20 kDa.

C154. The composition of clause C147 or C148, wherein the polysaccharide has an NMR spectrum as shown in FIG. 6.

C155. The composition of clause C147 or C148, wherein the polysaccharide is a cell surface polysaccharide.

C156. The composition of clause C147 or C148, wherein the polysaccharide is a capsular polysaccharide.

C157. The composition of clause C147 or C148, wherein the polysaccharide has been chemically synthesized.

C158. The composition of clause C147 or C148, wherein the polysaccharide is conjugated to a carrier protein.

C159. The composition of clause C158, wherein the carrier protein is a protein selected from the group consisting of a diphtheria toxoid, CRM197, a tetanus toxoid, a cholera toxoid, a pertussis toxoid, an *E. coli* heat labile toxoid (LT), a pneumolysin toxoid, pneumococcal surface protein A (PspA), pneumococcal adhesin protein A (PsaA), a C5a peptidase from *Streptococcus, Haemophilus influenzae* protein D, ovalbumin, keyhole limpet haemocyanin (KLH), bovine serum albumin (BSA), purified protein derivative of tuberculin (PPD), and a *Pseudomonas* exotoxin, or its derivatives.

C160. The composition of clause C159, wherein the carrier protein is $CRM_{197}$.

C161. An isolated polysaccharide comprising a repeating unit of -6-β-D-Fruf-2, wherein Fru is a fructose moiety, wherein the polysaccharide is an *Enterococcus faecium* TX0016 (DO; E1794) polysaccharide.

C162. An isolated polysaccharide comprising a repeating unit of -6-β-D-Fruf-2, wherein Fru is a fructose moiety, wherein the polysaccharide is an *Enterococcus faecium* E0155 polysaccharide.

C163. The polysaccharide of clause C161 or C162, wherein the repeating unit comprises [-6-β-D-Fruf-2]n, wherein Fru is a fructose moiety, and wherein n is an integer from 1000 to 100,000.

C164. The polysaccharide of clause C163, wherein n is between about 35,000 to about 45,000.

C165. The polysaccharide of clause C161 or C162, wherein the molecular weight of the polysaccharide is between about 10,000 kDa and 20,000 kDa.

C166. The polysaccharide of clause C161 or C162, wherein the polysaccharide has an NMR spectrum as shown in FIG. 1.

C167. The polysaccharide of clause C161 or C162, wherein the polysaccharide is a cell surface polysaccharide.

C168. The polysaccharide of clause C161 or C162, wherein the polysaccharide is a capsular polysaccharide.

C169. The polysaccharide of clause C161 or C162, wherein the polysaccharide is immunogenic.

C170. The polysaccharide of clause C169, wherein the polysaccharide is capable of inducing an immune response with opsonic activity.

C171. The polysaccharide of clause C169, wherein the polysaccharide is capable of inducing a bactericidal immune response.

C172. A polysaccharide comprising a repeating unit of -6-β-D-Fruf-2, wherein Fru is a fructose moiety, wherein the polysaccharide is an *Enterococcus faecium* TX0016 (DO; E1794) polysaccharide.

C173. A polysaccharide comprising a repeating unit of -6-β-D-Fruf-2, wherein Fru is a fructose moiety, wherein the polysaccharide is an *Enterococcus faecium* E0155 polysaccharide.

C174. The polysaccharide of clause C172 or C173, wherein the repeating unit comprises [-6-β-D-Fruf-2]n, wherein Fru is a fructose moiety, and wherein n is an integer from 1000 to 100,000.

C175. The polysaccharide of clause C174, wherein n is between about 35,000 to about 45,000.

C176. The polysaccharide of clause C172 or C173, wherein the molecular weight of the polysaccharide is between about 10,000 kDa and 20,000 kDa.

C177. The polysaccharide of clause C172 or C173, wherein the polysaccharide has an NMR spectrum as shown in FIG. 1.

C178. The polysaccharide of clause C172 or C173, wherein the polysaccharide is a cell surface polysaccharide.

C179. The polysaccharide of clause C172 or C173, wherein the polysaccharide is a capsular polysaccharide.

C180. The polysaccharide of clause C172 or C173, wherein the polysaccharide is immunogenic.

C181. The polysaccharide of clause C180, wherein the polysaccharide is capable of inducing an immune response with opsonic activity.

C182. The polysaccharide of clause C180, wherein the polysaccharide is capable of inducing a bactericidal immune response.

C183. The polysaccharide of clause C172 or C173, wherein the polysaccharide has been chemically synthesized.

C184. An immunogenic composition comprising an effective amount of a polysaccharide and a pharmaceutically acceptable diluent, wherein the polysaccharide comprises a repeating unit of -6-β-D-Fruf-2, wherein Fru is a fructose moiety, and wherein the polysaccharide is an *Enterococcus faecium* TX0016 (DO; E1794) polysaccharide.

C185. An immunogenic composition comprising an effective amount of a polysaccharide and a pharmaceutically acceptable diluent, wherein the polysaccharide comprises a repeating unit of -6-β-D-Fruf-2, wherein Fru is a fructose moiety, and wherein the polysaccharide is an *Enterococcus faecium* E0155 polysaccharide.

C186. The composition of clause C184 or C185, wherein the repeating unit comprises [-6-β-D-Fruf-2]n, wherein Fru is a fructose moiety, and wherein n is an integer from 1000 to 100,000.

C187. The composition of clause C186, wherein n is between about 35,000 to about 45,000.

C188. The composition of clause C184 or C185, wherein the molecular weight of the polysaccharide is between about 10,000 kDa and 20,000 kDa.

C189. The composition of clause C184 or C185, wherein the polysaccharide has an NMR spectrum as shown in FIG. 1.

C190. The composition of clause C184 or C185, wherein the polysaccharide is a cell surface polysaccharide.

C191. The composition of clause C184 or C185, wherein the polysaccharide is a capsular polysaccharide.

C192. The composition of clause C184 or C185, wherein the polysaccharide has been chemically synthesized.

C193. The composition of clause C184 or C185, wherein the polysaccharide is conjugated to a carrier protein.

C194. The composition of clause C193, wherein the carrier protein is a protein selected from the group consisting of a diphtheria toxoid, CRM197, a tetanus toxoid, a cholera toxoid, a pertussis toxoid, an *E. coli* heat labile toxoid (LT), a pneumolysin toxoid, pneumococcal surface protein A (PspA), pneumococcal adhesin protein A (PsaA), a C5a peptidase from *Streptococcus*, *Haemophilus influenzae* protein D, ovalbumin, keyhole limpet haemocyanin (KLH), bovine serum albumin (BSA), purified protein derivative of tuberculin (PPD), and a *Pseudomonas* exotoxin, or its derivatives.

C195. The composition of clause C194, wherein the carrier protein is $CRM_{197}$.

C196. A composition comprising at least two polysaccharides as in any one of clauses C1-040, C62-C99, C120-C146, or C161-C183.

C197. The composition according to clause C196, wherein the composition comprises at least three isolated polysaccharides as in any of clauses C1-C40, C62-C99, C120-C146, or C161-C183.

C198. The composition according to clause C196, wherein the composition comprises at least one polysaccharide as any one of clauses C1-C40, at least one polysaccharide as in any one of clauses C62-C99, at least one polysaccharide as in any one of clauses C120-C146, and at least one polysaccharide as in any one of clauses C161-C183.

C199. The composition according to clause C196, wherein each polysaccharide is conjugated to a carrier molecule.

C200. The composition according to clause C199, wherein the carrier molecule is a carrier protein.

C201. The composition according to clause C200, wherein the carrier protein is a protein selected from the group consisting of a diphtheria toxoid, $CRM_{197}$, a tetanus toxoid, a cholera toxoid, a pertussis toxoid, an *E. coli* heat labile toxoid (LT), a pneumolysin toxoid, pneumococcal surface protein A (PspA), pneumococcal adhesin protein A (PsaA), a C5a peptidase from *Streptococcus, Haemophilus influenzae* protein D, ovalbumin, keyhole limpet haemocyanin (KLH), bovine serum albumin (BSA), purified protein derivative of tuberculin (PPD), and a *Pseudomonas* exotoxin, or its derivatives.

C202. The composition according to clause C201, wherein the carrier protein is $CRM_{197}$.

C203. The composition according to clause C196, further comprising a pharmaceutically acceptable diluent.

C204. A method of inducing an immune response in a mammal comprising administering an effective amount of a polysaccharide as in any of clauses C1-C40, C62-C99, C120-C146, or C161-C183.

C205. The method of clause C204, wherein the immune response is against a Gram-positive coccus.

C206. The method of clause C205, wherein the immune response is against *Enterococcus*.

C207. A method of inducing an immune response in a mammal comprising administering an effective amount of a composition, which comprises a polysaccharide as in any of clauses C1-C40, C62-C99, C120-C146, or C161-C183.

C208. The method of clause C207, wherein the composition comprises a composition as in any of clauses C41-C61, C100-C119, C147-C160, or C184-C195

C209. The method of clause C207, wherein the immune response is against a Gram-positive coccus.

C210. The method of clause C209, wherein the immune response is against *Enterococcus*.

C211. A method for producing an isolated polysaccharide as in any of clauses C1-C40, C62-C99, C120-C146, or C161-C183, comprising culturing a Gram positive coccus bacterium having an ability to produce the polysaccharide; and collecting the polysaccharide produced by the bacterium.

C212. The method of clause C211, wherein the Gram-positive coccus is *Enterococcus*.

C213. The method of clause C212, wherein the Gram-positive coccus is *Enterococcus faecium*.

C214. The method of clause C213, wherein the Gram-positive coccus is *Enterococcus faecium* TX0016 (DO; E1794).

C215. The method of clause C213, wherein the Gram-positive coccus is *Enterococcus faecium* E0155.

C216. A method of detecting a Gram-positive coccus in a sample comprising contacting a polysaccharide as in any of clauses C1-C40, C62-C99, C120-C146, or C161-C183; detecting an antibody-antigen conjugate complex, wherein the presence of the antibody-antigen complex indicates the presence of a Gram-positive coccus in the sample.

C217. An isolated antibody or fragment thereof that specifically binds to a polysaccharide as in any of clauses C1-C40, C62-C99, C120-C146, or C161-C183.

C218. A composition comprising an isolated antibody or fragment thereof as in clause C217.

C219. A method of detecting a Gram-positive coccus in a sample comprising contacting an antibody as in clause C217; detecting an antibody-antigen conjugate complex, wherein the presence of the antibody-antigen complex indicates the presence of a Gram-positive coccus in the sample.

C220. A method of producing an isolated antibody or antibody fragment thereof comprising administering an effective amount of a polysaccharide as in any of clauses C1-C40, C62-C99, C120-C146, or C161-C183 to a mammal; and isolating the antibody or fragment thereof produced by the mammal.

The invention claimed is:

1. A non-naturally occurring polysaccharide comprising a legionaminic acid moiety, a N-acetylgalactosamine moiety, a galactose moiety, and a glucose moiety, wherein the polysaccharide comprises a repeating unit of a structure represented by:

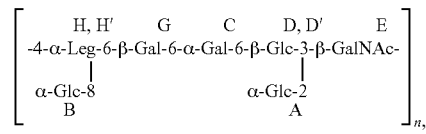

wherein Leg is a legionaminic acid moiety, Gal is a galactose moiety, Glc is a glucose moiety, and GalNAc is a N-acetylgalactosamine moiety, and wherein n is an integer from 40 to 60, and wherein the polysaccharide is conjugated to a carrier protein.

2. The polysaccharide of claim 1, wherein the polysaccharide is a Gram-positive coccal polysaccharide.

3. The polysaccharide of claim 1, wherein the polysaccharide is an *Enterococcus* polysaccharide.

4. The polysaccharide of claim 1, wherein the polysaccharide is an *Enterococcus faecium* polysaccharide.

5. The polysaccharide of claim 1, wherein the polysaccharide is an *Enterococcus faecium* TX0016 (DO; E1794) polysaccharide.

6. The polysaccharide of claim 1, wherein the polysaccharide is a cell surface polysaccharide.

7. The polysaccharide of claim 1, wherein the polysaccharide is a capsular polysaccharide.

8. The polysaccharide of claim 1, wherein the polysaccharide is immunogenic.

9. The polysaccharide of claim 1, wherein the polysaccharide is capable of inducing an immune response with opsonic activity.

10. The polysaccharide of claim 1, wherein the polysaccharide is capable of inducing a bactericidal immune response.

11. The polysaccharide of claim 1, wherein the polysaccharide is isolated.

12. The polysaccharide of claim 1, wherein the polysaccharide is synthetic.

13. The polysaccharide of claim 1, wherein the carrier protein is a protein selected from the group consisting of a diphtheria toxoid, CRM197, a tetanus toxoid, a cholera toxoid, a pertussis toxoid, an *E. coli* heat labile toxoid (LT), a pneumolysin toxoid, pneumococcal surface protein A (PspA), pneumococcal adhesin protein A (PsaA), a C5a peptidase from *Streptococcus, Haemophilus influenzae* protein D, ovalbumin, keyhole limpet haemocyanin (KLH), bovine serum albumin (BSA), purified protein derivative of tuberculin (PPD), and a *Pseudomonas* exotoxin, or its derivatives.

14. The polysaccharide of claim 1, wherein the carrier protein is $CRM_{197}$.

* * * * *